US011548949B2

(12) United States Patent
Brondyk et al.

(10) Patent No.: US 11,548,949 B2
(45) Date of Patent: *Jan. 10, 2023

(54) COMPOSITIONS FOR INCREASING HALF-LIFE OF A THERAPEUTIC AGENT IN CANINES AND METHODS OF USE

(71) Applicant: Invetx, Inc., Boston, MA (US)

(72) Inventors: William Brondyk, Mansfield, MA (US); Brett Chevalier, Melrose, MA (US); Juergen Horn, Marblehead, MA (US); Madhusudan Natarajan, Waban, MA (US)

(73) Assignee: Invetx, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/861,077

(22) Filed: Apr. 28, 2020

(65) Prior Publication Data
US 2020/0362035 A1 Nov. 19, 2020

Related U.S. Application Data

(63) Continuation of application No. 16/733,105, filed on Jan. 2, 2020.

(60) Provisional application No. 62/788,035, filed on Jan. 3, 2019.

(51) Int. Cl.
| | | |
|---|---|---|
| C07K 16/00 | (2006.01) | |
| C12P 21/08 | (2006.01) | |
| A61K 39/395 | (2006.01) | |
| C07K 16/28 | (2006.01) | |
| C07K 1/00 | (2006.01) | |
| A61K 38/00 | (2006.01) | |

(52) U.S. Cl.
CPC .......... C07K 16/283 (2013.01); A61K 38/00 (2013.01); C07K 2317/524 (2013.01); C07K 2317/526 (2013.01); C07K 2317/569 (2013.01); C07K 2317/622 (2013.01); C07K 2319/00 (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | DeCant et al. | |
| 4,447,233 A | 5/1984 | Mayfield | |
| 4,487,603 A | 12/1984 | Harris | |
| 4,634,665 A | 1/1987 | Axel et al. | |
| 5,179,017 A | 1/1993 | Axel et al. | |
| 5,292,658 A | 3/1994 | Cormier et al. | |
| 5,418,155 A | 5/1995 | Cormier et al. | |
| 5,683,888 A | 11/1997 | Campbell | |
| 5,741,668 A | 4/1998 | Ward et al. | |
| 5,777,079 A | 7/1998 | Tsien et al. | |
| 5,804,387 A | 9/1998 | Cormack et al. | |
| 5,874,304 A | 2/1999 | Zolotukhin et al. | |
| 5,876,995 A | 3/1999 | Bryan | |
| 5,925,558 A | 7/1999 | Tsien et al. | |
| 8,790,651 B2 | 7/2014 | Bammert et al. | |
| 2006/0067930 A1 | 3/2006 | Adams et al. | |
| 2007/0148164 A1* | 6/2007 | Farrington | A61P 43/00 435/328 |
| 2008/0181887 A1* | 7/2008 | Dall-Acqua | C07K 16/1027 424/133.1 |
| 2013/0129727 A1 | 5/2013 | Zhang et al. | |
| 2018/0009869 A1† | 1/2018 | Yuefeng | |
| 2020/0216536 A1 | 7/2020 | Brondyk et al. | |
| 2021/0347854 A1 | 11/2021 | Brondyk et al. | |
| 2022/0009994 A1 | 1/2022 | Brondyk et al. | |

FOREIGN PATENT DOCUMENTS

| | | |
|---|---|---|
| EP | 3892632 | 10/2021 |
| WO | WO 92/15673 | 9/1992 |
| WO | WO 95/07463 | 3/1995 |
| WO | WO 98/14605 | 4/1998 |
| WO | WO 98/26277 | 6/1998 |
| WO | WO 99/49019 | 9/1999 |
| WO | WO 2010/110838 | 9/2010 |
| WO | WO 2010/117448 | 10/2010 |
| WO | WO 2017/186928 | 11/2017 |
| WO | WO 2018/073185 | 4/2018 |
| WO | WO 2019/035010 | 2/2019 |
| WO | WO 2020/056393 | 3/2020 |
| WO | WO 2020/082048 | 4/2020 |
| WO | WO 2020/116560 | 6/2020 |
| WO | WO 2020/142625 | 7/2020 |
| WO | WO 2021/212081 | 10/2021 |
| WO | WO 2021/212084 | 10/2021 |

OTHER PUBLICATIONS

Tang et al. Veterinary Immunology and Immunopathology 2001, 80:259-270. (Year: 2001).*
Beniaminovitz et al., "Prevention of rejection in cardiac transplantation by blockade of the interleukin-2 receptor with a monoclonal antibody," New Engl. J. Med., 2000, 342(9):613-619.
Bergeron et al., "Comparative functional characterization of canine IgG subclasses." Veterinary Immunology and Immunopathology, 2014, 157(1-2):31-41.
Better et al., "*Escherichia coli* secretion of an active chimeric antibody fragment." Science, 1998, 240(4855):1041-1043.
Booth et al., "Extending human IgG half-life using structure-guided design," MAbs, 2018, 10(7):1098-1110.
Borrok et al., "pH-dependent binding engineering reveals an FcRn affinity threshold that governs IgG recycling," J. Biol. Chem., 2015, 290(7)4282-4290.
Chalfie et al., "Green fluorescent protein as a marker for gene expression." Science, 1994, 263(5148):802-805.

(Continued)

*Primary Examiner* — Chun W Dahle
(74) *Attorney, Agent, or Firm* — Clark & Elbing LLP

(57) ABSTRACT

Provided are compositions for increasing the half-life of a polypeptide or polypeptides in a canine and methods of their use. The compositions involve variant canine IgG Fc regions.

7 Claims, 28 Drawing Sheets
Specification includes a Sequence Listing.

(56) References Cited

OTHER PUBLICATIONS

Dall'Acqua et al., "Increasing the affinity of a human IgG1 for the neonatal Fc receptor: biological consequences," J. Immunol., 2002, 169(9):5171-5180.
Deng et al., "Pharmacokinetics of humanized monoclonal anti-tumor necrosis factor-{alpha} antibody and its neonatal Fc receptor variants in mice and cynomolgus monkeys," Drug Metab. Dispos., 2010, 38(4):600-605.
Ghosh et al., "Natalizumab for active Crohn's disease," New Engl. J. Med., 2003, 348(1):24-32.
Heim et al., "Engineering green fluorescent protein for improved brightness, longer wavelengths and fluorescence resonance energy transfer," Curr. Biol., 1996, 6(2):178-182.
Hinton et al., "Engineered human IgG antibodies with longer serum half-lives in primates." J. Biol. Chem., 2004, 279(8):6213-6216.
Hogrefe et al., "Creating randomized amino acid libraries with the QuikChange Multi Site-Directed Mutagenesis Kit," Biotechniques., 2002, 33(5):1158-1165.
Ichiki et al., "Regulation of the expression of human C epsilon germline transcript. Identification of a novel IL-4 responsive element," J. Immunol., 1993, 150(12):5408-5417.
Kaufman et al. "Amplification and expression of sequences cotransfected with a modular dihydrofolate reductase complementary dna gene," Mol. Biol. 159(4):601 621.
Lei et al., "Characterization of the Erwinia carotovora pelB gene and its product pectate lyase," J. Bacteriol., 1987, 169(9)4379-83.
Lipsky' et al. "Infliximab and methotrexate in the treaunent of rheumatoid arthritis. Anti-Tumor Necrosis Factor Trial in Rheuma-toid Arthritis with Concomitant Therapv Study Group," New Engl. J. Med., 2000, 343(22):1594-1602.
Milgrom et al., "Treatment of allergic asthma with monoclonal anti-IgE antibody. rhuMAb-E25 Study Group," New Engl. J. Med., 1999, 341(26):1966-1973.
Mizushima et al., "pEF-BOS, a powerfill mammalian expression vector," Nucleic Acids Res., 18(17):5322.
Monnet et al., "Combined glvco- and protein-Fc engineering simul-taneously enhance cytotoxicity and half-life of a therapeutic anti-body," MABS., 2014, 6(2)422-436.
Morrison et al., "Combinatorial alanine-scanning," Curr. Opin. Chem. Biol., 2001, 5(3):302-307.
Mulligan et al., "Synthesis of rabbit beta-globin in cultured monkey kidney cells following infection with a SV40 beta-globin recombi-nant genome," Nature, 1979, 277(5692):108-14.
Nolan et al., "Fluorescence-activated cell analysis and sorting of viable mammalian cells based on beta-D-galactosidase activity after transduction of *Escherichia coli* lacZ," Proc. Natl. Acad. Sci. U.S.A., 1988, 85(8):2603-2607.
Petkova et al., "Enhanced half-life of geneticallv engineered human IgG1 antibodies in a humanized FcRn mouse model: potential application in humorally mediated autoimmune disease," Int. Immunol. 18(12):1759-1769.
Powers et al., "Expression of single-chain Fv-Fc fusions in Pichiapastoris," J Immunol Methods., 2001, 251(1-2):123-35.
Robbie et al., "A novel investigational Fc-modified humanized monoclonal antibody, motavizumab-YTE, has an extended half-life in healthy adults," Antimicrob. Agents Ch., 2013, 57(12):6147-6153.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 2001, 276(9):6591-6604.
Slamon et al., "Use of chemotherapy plus a monoclonal antibody against HERZ for metastatic breast cancer that overexpresses HER2," New Engl. J. Med., 2001, 344(11):783-792.
Stauber et al., "Development and applications of enhanced green fluorescent protein mutants," Biotechniques. 1998, 24(2)462-471.
Tang et al., "Cloning and characterization of cDNAs encoding four different canine immunoglobulin gamma chains," Vet. Immunol. Immunopathol., 2001, 80(3-4):259-270.

Urlaub et al., "Isolation of Chinese hamster cell mutants deficient in dihydrofolate reductase activity," Proc. Natl. Acad. Sci. USA, 1980, 77(7)4216-4220.
Ward et al., "Binding activities of a repertoire of single immuno-globulin variable domains secreted from *Escherichia coli*," Nature, 1989, 341(6242):544-546.
Yeung et al., "Engineering human IgG1 affinity to human neonatal Fc receptor: impact of affmitv improvement on pharmacokinetics in primates," J. Immunol., 2009, 182(12):7663-7671.
Zalevsky et al., "Enhanced antibody half-life improves in vivo activity," Nat. Biotechnol., 2010, 28(2):157-159.
PCT International Search Report and Written Opinion in Interna-tional Appln. No. PCT/US2020/012081, dated Aug. 31, 2020, 22 pages.
PCT Invitation to Pay Additional Fees in International Appln. No. PCT/US2020/012081, dated Jul. 6, 2020, 15 pages.
PCT International Preliminary Report on Patentability in Interna-tional Appln. No. PCT/US2020/012081, dated Apr. 15, 2021, 10 pages.
Abdiche et al., "The neonatal Fc receptor (FcRn) binds indepen-dently to both sites of the IgG homodimer with identical affinity," mAbs, Mar. 2015, 7(2):331-343, 14 pages.
Gearing et al., "A fully caninised anti-NGF monoclonal antibody for pain relief in dogs," BMC Veterinary Research, Nov. 2013, 9:226, 12 pages.
GenBank Accession No. AAL35301.1, "immunoglobulin gamma heavy chain A [Canis lupus familiaris]," Nov. 26, 2001, 2 pages.
GenBank Accession No. AAL35302.1, "immunoglobulin gamma heavy chain B [Canis lupus familiaris]," dated Nov. 26, 2001, 2 pages.
GenBank Accession No. AAL35303.1, "immunoglobulin gamma heavy chainC [Canis lupus familiaris]," Nov. 26, 2001, 2 pages.
GenBank Accession No. AAL35304.1, "immunoglobulin gamma heavy chain D [Canis lupus familiaris]," Nov. 26, 2001, 2 pages.
GenBank Accession No. ABY55569.1, "immunoglobulin lambda light chain variable region, partial [Canis lupus familiaris]," Jul. 26, 2016, 2 pages.
GenBank Accession No. ABY57289.1, "immunoglobulin kappa light chain variable region, partial [Canis lupus familiaris]," Jul. 26, 2016, 1 page.
GenBank Accession No. U55762, "Cloning vector pEGFP-N1, complete sequence, enhanced green fluorescent protein (egfp) and neomycin phosphotransferase genes, complete cds," Aug. 22, 2003, 3 pages.
PCT International Preliminary Report on Patentability in Interna-tional Appln. No. PCT/US2020/012081, dated May 11, 2021, 10 pages.
Zhang et al., "PKSolver: An add-in program for pharmacokinetic and pharmacodynamic data analysis in Microsoft Excel," Comput. Methods Programs Biomed., Sep. 2010, 99(3):306-314.
PCT Written Opinion in International Appln. No. PCT/US2020/012081, dated Jan. 21, 2021, 9 pages.
US Third-Party Submission in United States U.S. Appl. No. 16/733,105, mailed May 28, 2021, 19 pages.
US Third-Party Submission in United States U.S. Appl. No. 16/861,077, mailed May 25, 2021, 19 pages.
Dong et al., "Quantitative Prediction of Human Pharmacokinetics for Monoclonal Antibodies," Clin Pharmacokinet, Feb. 2011, 50(2):131-142.
Gearing et al., "In Vitro and In Vivo Characterization of a Fully Felinized Therapeutic Anti-Nerve Growth Factor Monoclonal Anti-body for the Treatment of Pain in Cats," J Vet Intern Med, Jun. 2016, 30(4):1129-1137.
GenBank Accession No. AF198257.1, "Felis catus immunoglobulin kappa light chain mRNA, complete cds," Nov. 21, 1999, 2 pages.
GenBank Accession No. AY829266.1, "Fells catus beta-2 microglobulin mRNA, complete cds," Dec. 13, 2004, 1 page.
GenBank Accession No. BAA32229.1, "IgG1 heavy chain, partial [Felis catus]," Jul. 25, 2016, 2 pages.
GenBank Accession No. BAA32230.1, "IgG1 heavv chain, partial [Felis catus]," Jul. 25, 2016, 2 pages.

(56) References Cited

OTHER PUBLICATIONS

GenBank Accession No. E07339.1, "DNA sequence of C lambda gene in the constant region of feline antibody gene," Nov. 4, 2005, 1 page.

GenBank Accession No. KF773786.1, "Felis catus FcRn mRNA, partial cds," Mar. 28, 2014, 2 pages.

GenBank Accession No. KF811175.1, "Felis catus immunoglobulin G2 heavy chain consant region mRNA, partial cds," Mar. 28. 2014.

Kanai et al., "Identification of two allelic IgGl Ch coding regions (Cγl) of cat," Vet. Immunol. Immunopathol., Jan. 2000, 73(1):53-62.

Strietzel et al.. "In Vitro functional characterization of feline IgGs," Vet. Immunol, Immunopathol., Apr. 2014, 158(3-4):214-223.

US Third-Party Submission in U.S. Appl. No. 16/733,105, mailed Jul. 22, 2021, 14 pages.

imgt.org [online], "IMGT Scientific chart," 2016, retrieved from URL <http://www.imgt.org/IMGTScientificChart/Numbering/Hu_IGHGnber.html>, 7 pages.

Borrok et al., pH dependent Binding Engineering Reveals an FcRn Affinity Threshold That Governs IgG Recycling. J. Biol. Chem., vol. 290, No. 7, 9 pages, Feb. 13, 2015.†

Robbie et al., A Novel Investigational Fc-Modified Humanized Monoclonal Antibody, Motavizumab-YTE, Has an Extended Half-Life in Healthy Adults, Antimicrob. Agents Chemother., vol. 57, No. 12, 7 pages.†

* cited by examiner
† cited by third party

FIG. 1

```
         ▼— V_H                         *
CaIgG-A  MESVPCWVFL VVILKGVQGE VQLVESGGDL VKPGGSLRLS VASGFTFSS    50
CaIgG-B  ----LF---- -T-------- -R------T- ----K-- ---------RR    50
CaIgG-C  ----LY---- -A-------D ---------- ---- ------------      50
CaIgG-D  ----L----- -S-------- ---------- ---- --------------D   50

CaIgG-A  YYMHIRQAP KGLQRVAHI RGDGRTTHYA DAMKGFTIS RDNAKNTLY      100
CaIgG-B  -S-D-V--- -S--N--G- N---TG-S-S QTV------ ---------      100
CaIgG-C  CA-S-V--S --P-W--T- -Y--SDIY-- -----S--- ---------V-    100
CaIgG-D  -G-S-V--S ----W--AV SNR- D-Y-- ---------F---- ---------  100

*                    ▼— C_H1
CaIgG-A  QMNSLTVEDT AIYYCVKDI   YYGVG D YWGQGTLVTV SSASTTAPSV    150
CaIgG-B  -I----RA-S V--A-S W  SRNG  DL- ---------- ----------    150
CaIgG-C  ------RA-- V--A-A P PYDS-HY-M- ----P--SLF- ----------   150
CaIgG-D  --S--KA--- IH-VTGVW PRH---M   H--N--SLF- ----------     150
                     *
CaIgG-A  FPLAPSCGST SGSTVALACL VSGYFPEPVT VSWNSGSLTS GVHTFPSVLQ  200
CaIgG-B  ---------- ---------- ---------- ---------- ----------  200
CaIgG-C  --------Q- ---------- -----I---- -----V---- ----------  200
CaIgG-D  ---------- ---------- ---------- ---------- ----------  200

*                  ▼— hinge
CaIgG-A  SSGLHSLSSM VTVPSSRWPS ETFTCNVVHP ASNTKVDKPV FNECRCTDT   250
CaIgG-B  ----Y----- ---------- ------A--- P-K------- PKRENGRVPR  250
CaIgG-C  ----Y----- ---------- ------A--- -T-------- AK--E-KC N  250
CaIgG-D  ----Y----T ---------- ---------- ---------- PK-ST-KCI   250

▼— C_H2                           *
CaIgG-A    PPCPVP EPLGGPSVLI FPPKPKDILR ITRTPEVTCV VLDLGREDPE   300
CaIgG-B  PPDC-K--A- -M------F- ------TLL -A------- -V--DP----   300
CaIgG-C  CNNC- --GC GL------F- ---------V TA---T--- -V--DP-N--   300
CaIgG-D    SP---- ES------F- ---------- ------I--- ----------   300

*
CaIgG-A  VQISWFVDGK EVHTAKTQSR EQQFNGTVRV VSVLPIEHQD WLTGKEFKCR  350
CaIgG-B  ---------- QMQ-----P- -E-|---|-- ------G--- --K--Q-T-K  350
CaIgG-C  --------S- Q-Q--N--P- -E-S|---|- ------G--- --S--Q---K  350
CaIgG-D  ---------- --------P- ---|-S-|-- ---------- ----------  350

▼— C_H3                        *
CaIgG-A  VNHIDLPSPI ERTISKARGR AHKPSVYVLP PSPKELSSSD TVSITCLIKD  400
CaIgG-B  --NKA----- --------Q- -Q-------- --RE---K N ---L------  400
CaIgG-C  --NKA----- -EI---TP-Q -Q-N------ --RD-M-K N --TL---V--  400
CaIgG-D  ----G----- --------Q- -Q-------- ---------- --TL------  400

CaIgG-A  FYPPDIDVEW QSNGQQEPER KHEMTPPQLD EDGSYFLYSK LSVDKSRWQQ  450
CaIgG-B  -F-------- ---------S -Y-T------ ---------- ---------R  450
CaIgG-C  -F--E----- ---------S -Y-M------ ---------- ---------R  450
CaIgG-D  -F--E----- -----P---S -YHT-A---- ---------- ----------  450

*
CaIgG-A  GDFFTCAVMH ETLQNHYTDL SLSHSPGK                          500
CaIgG-B  --T-I----- -A-H----QE ---------                          500
CaIgG-C  --T-I----- -A-H----QI ---------                          500
CaIgG-D  --T------- -A-------- ---------                          500
```

FIG. 2

```
Canine.IgG.A  GPSVLIFPPKPKDILRITRTPEVTCVVLDLGREDPEVQISWFVDGKEVHT
Canine.IgG.D  GPSVFIFPPKPKDILRITRTPEITCVVLDLGREDPEVQISWFVDGKEVHT
Canine.IgG.B  GPSVFIFPPKPKDTLLIARTPEVTCVVVDLDPEDPEVQISWFVDGKQMQT
canine.IgG.C  GPSVFIFPPKPKDILVTARTPFVTCVVVDLDPENPEVQISWFVDSKQVQT
              ****:********** * :**** :********.*:******.*.:;:*

Canine.IgG.A  AKTQSREQQFNGTYRVVSVLPIEHQDWLTGKEFKCRVNHIDLPSPIERTISKAR
Canine.IgG.D  AKTQPREQQFNSTYRVVSVLPIEHQDWLTGKEFKCRVNHIGLPSPIERTISKAR
Canine.IgG.B  AKTQPREEQFNGTYRVVSVLPIGHQDWLKGKQFTCKVNNKALPSPIERTISKAR
Canine.IgG.C  ANTQPREEQSNGTYRVVSVLPIGHQDWLSGKQFKCKVKVNNKALPSPIEEIISKTP
              *.**.**:.*:**************.****.**:*.*:*:.:**;  ****.  ****.;
```

FIG. 3

```
Canine.IgG.A    KPSVYVLPPSPKELSSSDTVSITCLIKDFYPPDIDVEWQSNGQQEPERKHRMTPPQLDED
Canine.IgG.D    QPSVYVLPPSPKELSSSDTVTLTCLIKDFFPPEIDVEWQSNGQQEPESKYHTTAPQLDED
Canine.IgG.B    QPSVYVLPPSREEL-SKNTVSLTCLIKDFFPPEIDVEWQSNGQQEPESKYRTTPPQLDED
Canine.IgG.C    QPNVYVLPPSRDEM-SKNTVTLTCLVKDFFPPEIDVEWQSNGQQEPESKYRMTPPQLDED
                 * ******* ::  *:**.* **:**** **:*********:* *  **  *****

Canine.IgG.A    GSYFLYSKLSVDKSRWQQGDPFTCAVMHETLQNHYTDLSLSHSPGK
Canine.IgG.D    GSYFLYSKLSVDKSRWQQGDTFTCAVMHEALQNHYTDLSLSHSPGK
Canine.IgG.B    GSYFLYSKLSVDKSRWQRGDTFICAVMHEALHNHYTQESLSHSPGK
Canine.IgG.C    GSYFLYSKLSVDKSRWQRGDTFICAVMHEALHNHYTQISLSHSPGK
                ***************::**.*:******:*:****: *******
```

FIG. 4

```
Canine.IgG.A   VPEPLGGPSVLIFPPKPKDILRITRTPEVTCVVLDLGREDPEVQISWFVDGKEVHT
Canine.IgG.D   VPESLGGPSVFIFPPKPKDILRITRTPEITCVVLDLGREDPEVQISWFVDGKEVHT
Canine.IgG.B   APEMLGGPSVFIFPPKPKDTLLIARTPEVTCVVVDLDPEDPEVQISWFVDGKQMQT
Canine.IgG.C   GCGLLGGPSVFIFPPKPKDILVTARTPTVTCVVVDLDPENPEVQISWFVDSKQVQT
               *  :*:* ********* ** ***   ::: *:***.*** *.**:* :**** .  .*.*.*.***.:***.*.*:* ..

Canine.IgG.A   AKTQSREQQFNGTYRVVSVLPIEHQDWLTGKEFKCRVNHIDLPSPIERTISKARGRAHKP
Canine.IgG.D   AKTQPREQQFNSTYRVVSVLPIEHQDWLTGKEFKCRVNHIGLPSPIERTISKARGQAHQP
Canine.IgG.B   AKTQPREEQFNGTYRVVSVLPIGHQDWLKGKQFTCKVNNKALPSPIERTISKARGQAHQP
Canine.IgG.C   ANTQPREEQSNGTYRVVSVLPIGHQDWLSGKQFKCKVNNKALPSPIEEIISKTPGQAHQP
               *:**.**:*.*.***********.*****.**:*.*:**:  ***:**:*.**:..****

Canine.IgG.A   SVYYVLPPSPKELSSSDTVSITCLIKDFYPPDIDVEWQSNGQQEPERKHRMTPPQLDEDGS
Canine.IgG.D   SVVYVLPPSPKELSSSDTVTLTCLIKDFFPPEIDVEWQSNGQQEPESKYHTTAPQLDEDGS
Canine.IgG.B   SVYVLPSREEL-SKNTVSLTCLIKDFFPPDIDVEWQSNGQQEPESKYRTTPPQLDEDGS
Canine.IgG.C   NVYVLPPSRDEM-SKNTVTLTCLVKDFFPPEIDVEWQSNGQQEPESKYRMTPPQLDEDGS
               .* ***.*.: *:**..***:***::.**:***********:*  :. *.**:*

Canine.IgG.A   YFLYSKLSVDKSRWQQGDPFTCAVMHETLQNHYTDLSLSHSPGK
Canine.IgG.D   YFLYSKLSVDKSRWQQGDTFTCAVMHEALQNHYTDLSLSHSPGK
Canine.IgG.B   YFLYSKLSVDKSRWQRGDTFICAVMHEALHNHYTQESLSHSPGK
Canine.IgG.C   YFLYSKLSVDKSRWQRGDTFICAVMHEALHNHYTQISLSHSPGK
               *************:.**.*.*******:*:****: :*******
```

FIG. 5A

| | CH2 DOMAIN | | | | | | |
|---|---|---|---|---|---|---|---|
| | EU | hIgG1 | cIgG.A | cIgG.B | cIgG.C | cIgG.D | SM |
| A-strand | 237 | G | G | G | G | G | |
| | 238 | P | P | P | P | P | |
| | 239 | S | S | S | S | S | |
| | 240 | V | V | V | V | V | |
| | 241 | F | L | F | F | F | |
| | 242 | L | I | I | I | I | |
| | 243 | F | F | F | F | F | |
| | 244 | P | P | P | P | P | |
| | 245 | P | P | P | P | P | |
| | 246 | K | K | K | K | K | |
| | 247 | P | P | P | P | P | |
| | 248 | K | K | K | K | K | |
| | 249 | D | D | D | D | D | |
| | 250 | T | I | T | I | I | E or Q |
| | 251 | L | L | L | L | L | D or E |
| AB-turn | 252 | M | R | L | V | R | Y |
| | 253 | I | I | I | T | I | |
| B-strand | 254 | S | T | A | A | T | T |
| | 255 | R | R | R | R | R | |
| | 256 | T | T | T | T | T | D, E, or F |
| | 257 | P | P | P | P | P | |
| | 258 | E | E | E | T | E | |
| | 259 | V | V | V | V | I | |
| | 260 | T | T | T | T | T | |
| | 261 | C | C | C | C | C | |
| | 262 | V | V | V | V | V | |
| | 263 | V | V | V | V | V | |
| | 264 | V | L | V | V | L | |
| BC-loop | 265 | D | D | D | D | D | |
| | 266 | V | L | L | L | L | |
| | 267 | S | G | D | D | G | |
| | 268 | H | R | P | P | R | |
| | 269 | E | E | E | E | E | |
| | 270 | D | D | D | N | D | |
| | 271 | P | P | P | P | P | |
| | 272 | E | E | E | E | E | |
| | 273 | V | V | V | V | V | |

FIG. 5B

| | | | | | | | |
|---|---|---|---|---|---|---|---|
| | 274 | K | Q | Q | Q | Q | |
| C-strand | 275 | F | I | I | I | I | |
| | 276 | N | S | S | S | S | |
| | 277 | W | W | W | W | W | |
| | 278 | Y | F | F | F | F | |
| | 279 | V | V | V | V | V | |
| | 280 | D | D | D | D | D | |
| | 281 | G | G | G | S | G | |
| CD-loop | 282 | V | K | K | K | K | |
| | 283 | E | E | Q | Q | E | |
| | 284 | V | V | M | V | V | |
| | 285 | H | H | Q | Q | H | N,D |
| | - | - | - | - | - | - | |
| | - | - | - | - | - | - | |
| D-strand | 286 | N | T | T | T | T | D |
| | 287 | A | A | A | A | A | |
| | 288 | K | K | K | N | K | |
| | 289 | T | T | T | T | T | |
| | 290 | K | Q | Q | Q | Q | |
| | 291 | P | S | P | P | P | |
| | 292 | R | R | R | R | R | |
| | 293 | E | E | E | E | E | |
| DE-turn | 294 | E | Q | E | E | Q | |
| | 295 | Q | Q | Q | Q | Q | |
| | 296 | Y | F | F | S | F | |
| | 297 | N | N | N | N | N | |
| | 298 | S | G | G | G | S | |
| | 299 | T | T | T | T | T | |
| | 300 | Y | Y | Y | Y | Y | |
| | 301 | R | R | R | R | R | |
| E-strand | 302 | V | V | V | V | V | |
| | 303 | V | V | V | V | V | |
| | 304 | S | S | S | S | S | |
| | 305 | V | V | V | V | V | |
| | 306 | L | L | L | L | L | |
| | 307 | T | P | P | P | P | R,Q,A |
| | 308 | V | I | I | I | I | P |
| | 309 | L | E | G | G | E | P |
| | 310 | H | H | H | H | H | |
| | 311 | Q | Q | Q | Q | Q | V |

FIG. 5C

|  | | hIgG1 | cIgGA | cIgGB | cIgGC | cIgGD | SM |
|---|---|---|---|---|---|---|---|
|  | 312 | D | D | D | D | D | |
|  | 313 | W | W | W | W | W | |
| EF-turn | - | - | - | - | - | - | |
|  | - | - | - | - | - | - | |
| F-strand | 314 | L | L | L | L | L | |
|  | 315 | N | T | K | S | T | D |
|  | 316 | G | G | G | G | G | |
|  | 317 | K | K | K | K | K | |
|  | 318 | E | E | Q | Q | E | |
|  | 319 | Y | F | F | F | F | |
|  | 320 | K | K | T | K | K | |
|  | 321 | C | C | C | C | C | |
| FG-loop | 322 | K | R | K | K | R | |
|  | 323 | V | V | V | V | V | |
|  | 324 | S | N | N | N | N | |
|  | 325 | N | H | N | N | H | |
|  | 326 | K | I | K | K | I | |
|  | 327 | A | D | A | A | G | |
|  | - | - | - | - | - | - | |
|  | 328 | L | L | L | L | L | |
|  | 329 | P | P | P | P | P | |
|  | 330 | A | S | S | S | S | |
|  | 331 | P | P | P | P | P | |
|  | 332 | I | I | I | I | I | |
| G-strand | 333 | E | E | E | E | E | |
|  | 334 | K | R | R | E | R | |
|  | 335 | T | T | T | I | T | |
|  | 336 | I | I | I | I | I | |
|  | 337 | S | S | S | S | S | |
|  | 338 | K | K | K | K | K | |
|  | 339 | A | A | A | T | A | |
|  | 340 | K | R | R | P | R | | hIgG1 = human IgG1; cIgGA = canine IgG.A; cIgGB = canine IgG.B; cIgGC = canine IgG.C; cIgGD = canine IgG.D; SM= mutations that can extent antibody half-life

FIG. 6A

| | | CH3 DOMAIN | | | | | |
|---|---|---|---|---|---|---|---|
| | EU | hIgG1 | cIgG.A | cIgG.B | cIgG.C | cIgG.D | SM |
| A-strand | 345 | E | K | Q | Q | Q | |
| | 346 | P | P | P | P | P | |
| | 347 | Q | S | S | N | S | |
| | 348 | V | V | V | V | V | |
| | 349 | Y | Y | Y | Y | Y | |
| | 350 | T | V | V | V | V | |
| | 351 | L | L | L | L | L | |
| | 352 | P | P | P | P | P | |
| | 353 | P | P | P | P | P | |
| | 354 | S | S | S | S | S | |
| | 355 | R | P | R | R | P | |
| | 356 | D | K | E | D | K | |
| | 357 | E | E | E | E | E | |
| | 358 | L | L | L | M | L | |
| | 359 | T | S | S | S | S | |
| AB-turn | - | - | - | - | - | - | |
| | - | - | S | - | - | S | |
| B-strand | 360 | K | S | K | K | S | |
| | 361 | N | D | N | N | D | |
| | 362 | Q | T | T | T | T | |
| | 363 | V | V | V | V | V | |
| | 364 | S | S | S | T | T | |
| | 365 | L | I | L | L | L | |
| | 366 | T | T | T | T | T | |
| | 367 | C | C | C | C | C | |
| | 368 | L | L | L | L | L | |
| | 369 | V | I | I | V | I | |
| | 370 | K | K | K | K | K | |
| BC-loop | 371 | G | D | D | D | D | |
| | 372 | F | F | F | F | F | |
| | 373 | Y | Y | F | F | F | |
| | 374 | P | P | P | P | P | |
| | - | - | - | - | - | - | |
| | - | - | - | - | - | - | |
| | 375 | S | P | P | P | P | |
| | 376 | D | D | D | E | E | |
| | 377 | I | I | I | I | I | |

FIG. 6B

| Region | Pos | 1 | 2 | 3 | 4 | 5 | 6 |
|---|---|---|---|---|---|---|---|
| | 378 | A | D | D | D | D | V |
| C-strand | 379 | V | V | V | V | V | |
| | 380 | E | E | E | E | E | A |
| | 381 | W | W | W | W | W | |
| | 382 | E | Q | Q | Q | Q | |
| | 383 | S | S | S | S | S | |
| | 384 | N | N | N | N | N | |
| | 385 | G | G | G | G | G | |
| CD-loop | 386 | Q | Q | Q | Q | Q | |
| | 387 | P | Q | Q | Q | P | |
| | 388 | E | E | E | E | E | |
| | 389 | N | P | P | P | P | |
| | - | - | - | E | E | E | E |
| | - | - | - | R | S | S | S |
| D-strand | 390 | N | K | K | K | K | |
| | 391 | Y | H | Y | Y | Y | |
| | 392 | K | R | R | R | H | |
| | 393 | T | M | T | M | T | |
| | 394 | T | T | T | T | T | |
| | 395 | P | P | P | P | A | |
| | 396 | P | P | P | P | P | |
| | 397 | V | Q | Q | Q | Q | |
| DE-turn | 398 | L | L | L | L | L | |
| | 399 | D | D | D | D | D | |
| | 400 | S | E | E | E | E | |
| | 401 | D | D | D | D | D | |
| | 402 | G | G | G | G | G | |
| | 403 | S | S | S | S | S | |
| | 404 | F | Y | Y | Y | Y | |
| | 405 | F | F | F | F | F | |
| E-strand | 406 | L | L | L | L | L | |
| | 407 | Y | Y | Y | Y | Y | |
| | 408 | S | S | S | S | S | |
| | 409 | K | K | K | K | K | |
| | 410 | L | L | L | L | L | |
| | 411 | T | S | S | S | S | |
| | 412 | V | V | V | V | V | |
| | 413 | D | D | D | D | D | |
| | 414 | K | K | K | K | K | |
| | 415 | S | S | S | S | S | |

FIG. 6C

| | | hIgG1 | cIgGA | cIgGB | cIgGC | cIgGD | SM |
|---|---|---|---|---|---|---|---|
| | 416 | R | R | R | R | R | |
| | 417 | W | W | W | W | W | |
| EF-turn | | - | - | - | - | - | |
| | | - | - | - | - | - | |
| F-strand | 418 | Q | Q | Q | Q | Q | |
| | 419 | Q | Q | R | R | Q | |
| | 420 | G | G | G | G | G | |
| | 421 | N | D | D | D | D | |
| | 422 | V | P | T | T | T | |
| | 423 | F | F | F | F | F | |
| | 424 | S | T | I | I | T | |
| | 425 | C | C | C | C | C | |
| FG-loop | 426 | S | A | A | A | A | |
| | 427 | V | V | V | V | V | |
| | 428 | M | M | M | M | M | L |
| | 429 | H | H | H | H | H | |
| | 430 | E | E | E | E | E | A, K |
| | 431 | A | T | A | A | A | |
| | 432 | L | L | L | L | L | |
| | 433 | H | Q | H | H | Q | K |
| | 434 | N | N | N | N | N | S, A, F |
| | 435 | H | H | H | H | H | Y |
| | 436 | Y | Y | Y | Y | Y | H |
| | 437 | T | T | T | T | T | |
| G-strand | 438 | Q | D | Q | Q | D | |
| | 439 | K | L | E | I | L | |
| | 440 | S | S | S | S | S | |
| | 441 | L | L | L | L | L | |
| | 442 | S | S | S | S | S | |
| | 443 | L | H | H | H | H | |
| | 444 | S | S | S | S | S | |
| | 445 | P | P | P | P | P | |
| tail | 446 | G | G | G | G | G | |
| | 447 | K | K | K | K | K | | hIgG1 = human IgG1; cIgGA = canine IgG.A; cIgGB = canine IgG.B; cIgGC = canine IgG.C; cIgGD = canine IgG.D; SM= mutations that can extent antibody half-life Time - sec Time - sec Time - sec Time - sec Time - sec Time - sec Time - sec Time - sec Time - sec Time - sec Time - sec Time - sec Time - sec Time - sec

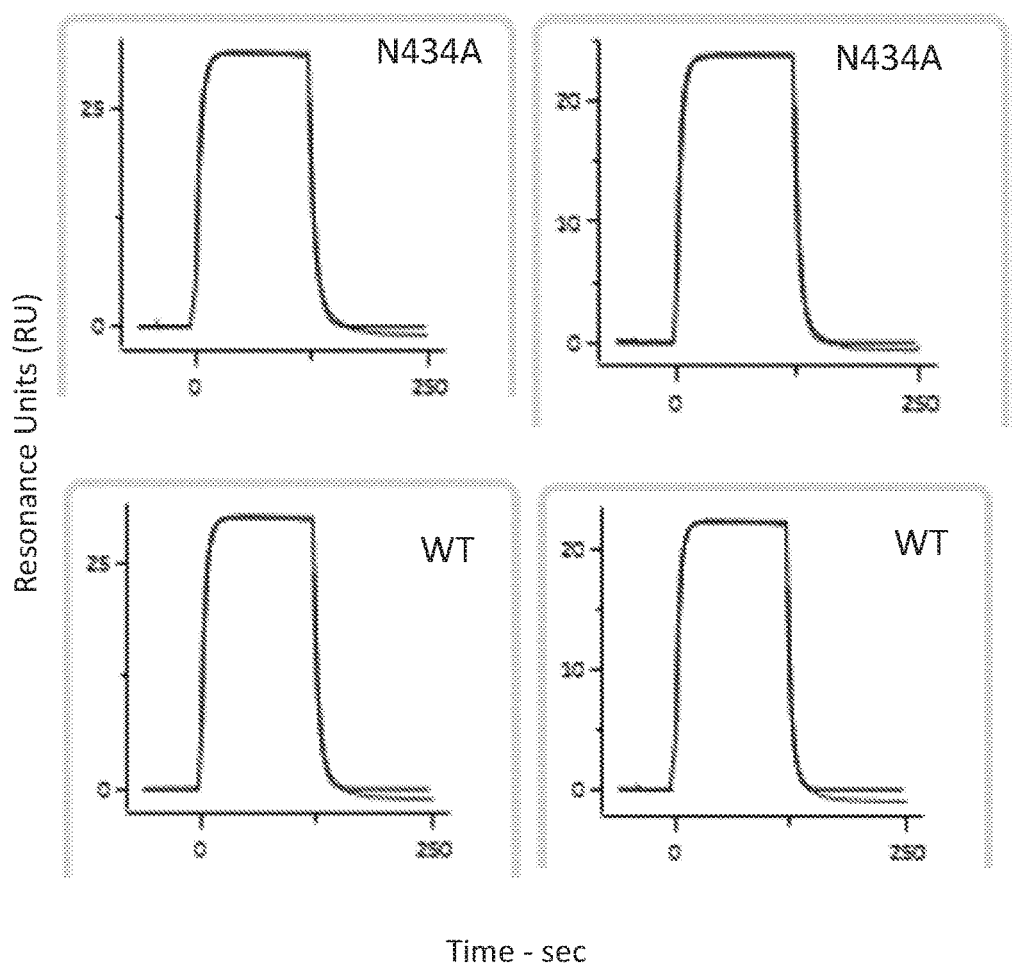

L252Y

N434Y    N434W

N434R    N434H

Wild-type

YTE

Time - sec

SEQUENCE LISTING

<160> NUMBER OF SEQ ID NOS: 29

<210> SEQ ID NO 1
<211> LENGTH: 104

```
<212> TYPE: PRT
<213> ORGANISM: Canine

<400> SEQUENCE: 1

Gly Pro Ser Val Leu Ile Phe Pro Pro Lys Pro Lys Asp Ile Leu Arg
1               5                   10                  15

Ile Thr Arg Thr Pro Glu Val Thr Cys Val Val Leu Asp Leu Gly Arg
            20                  25                  30

Glu Asp Pro Glu Val Gln Ile Ser Trp Phe Val Asp Gly Lys Glu Val
        35                  40                  45

His Thr Ala Lys Thr Gln Ser Arg Glu Gln Gln Phe Asn Gly Thr Tyr
    50                  55                  60

Arg Val Val Ser Val Leu Pro Ile Glu His Gln Asp Trp Leu Thr Gly
65                  70                  75                  80

Lys Glu Phe Lys Cys Arg Val Asn His Ile Asp Leu Pro Ser Pro Ile
                85                  90                  95

Glu Arg Thr Ile Ser Lys Ala Arg
            100

<210> SEQ ID NO 2
<211> LENGTH: 104
<212> TYPE: PRT
<213> ORGANISM: Canine

<400> SEQUENCE: 2

Gly Pro Ser Val Phe Ile Phe Pro Pro Lys Pro Lys Asp Thr Leu Leu
1               5                   10                  15

Ile Ala Arg Thr Pro Glu Val Thr Cys Val Val Val Asp Leu Asp Pro
            20                  25                  30

Glu Asp Pro Glu Val Gln Ile Ser Trp Phe Val Asp Gly Lys Gln Met
        35                  40                  45

Gln Thr Ala Lys Thr Gln Pro Arg Glu Glu Gln Phe Asn Gly Thr Tyr
    50                  55                  60

Arg Val Val Ser Val Leu Pro Ile Gly His Gln Asp Trp Leu Lys Gly
65                  70                  75                  80

Lys Gln Phe Thr Cys Lys Val Asn Asn Lys Ala Leu Pro Ser Pro Ile
                85                  90                  95

Glu Arg Thr Ile Ser Lys Ala Arg
            100

<210> SEQ ID NO 3
<211> LENGTH: 104
<212> TYPE: PRT
<213> ORGANISM: Canine

<400> SEQUENCE: 3

Gly Pro Ser Val Phe Ile Phe Pro Pro Lys Pro Lys Asp Ile Leu Val
1               5                   10                  15

Thr Ala Arg Thr Pro Thr Val Thr Cys Val Val Val Asp Leu Asp Pro
            20                  25                  30

Glu Asn Pro Glu Val Gln Ile Ser Trp Phe Val Asp Ser Lys Gln Val
        35                  40                  45

Gln Thr Ala Asn Thr Gln Pro Arg Glu Glu Gln Ser Asn Gly Thr Tyr
    50                  55                  60

Arg Val Val Ser Val Leu Pro Ile Gly His Gln Asp Trp Leu Ser Gly
65                  70                  75                  80

Lys Gln Phe Lys Cys Lys Val Asn Asn Lys Ala Leu Pro Ser Pro Ile
```

85                  90                  95

Glu Glu Ile Ile Ser Lys Thr Pro
            100

<210> SEQ ID NO 4
<211> LENGTH: 104
<212> TYPE: PRT
<213> ORGANISM: Canine

<400> SEQUENCE: 4

Gly Pro Ser Val Phe Ile Phe Pro Lys Pro Lys Asp Ile Leu Arg
1               5                   10                  15

Ile Thr Arg Thr Pro Glu Ile Thr Cys Val Val Leu Asp Leu Gly Arg
            20                  25                  30

Glu Asp Pro Glu Val Gln Ile Ser Trp Phe Val Asp Gly Lys Glu Val
        35                  40                  45

His Thr Ala Lys Thr Gln Pro Arg Glu Gln Gln Phe Asn Ser Thr Tyr
    50                  55                  60

Arg Val Val Ser Val Leu Pro Ile Glu His Gln Asp Trp Leu Thr Gly
65                  70                  75                  80

Lys Glu Phe Lys Cys Arg Val Asn His Ile Gly Leu Pro Ser Pro Ile
                85                  90                  95

Glu Arg Thr Ile Ser Lys Ala Arg
            100

<210> SEQ ID NO 5
<211> LENGTH: 106
<212> TYPE: PRT
<213> ORGANISM: Canine

<400> SEQUENCE: 5

Lys Pro Ser Val Tyr Val Leu Pro Pro Ser Pro Lys Glu Leu Ser Ser
1               5                   10                  15

Ser Asp Thr Val Ser Ile Thr Cys Leu Ile Lys Asp Phe Tyr Pro Pro
            20                  25                  30

Asp Ile Asp Val Glu Trp Gln Ser Asn Gly Gln Gln Glu Pro Glu Arg
        35                  40                  45

Lys His Arg Met Thr Pro Pro Gln Leu Asp Glu Asp Gly Ser Tyr Phe
    50                  55                  60

Leu Tyr Ser Lys Leu Ser Val Asp Lys Ser Arg Trp Gln Gln Gly Asp
65                  70                  75                  80

Pro Phe Thr Cys Ala Val Met His Glu Thr Leu Gln Asn His Tyr Thr
                85                  90                  95

Asp Leu Ser Leu Ser His Ser Pro Gly Lys
            100                 105

<210> SEQ ID NO 6
<211> LENGTH: 105
<212> TYPE: PRT
<213> ORGANISM: Canine

<400> SEQUENCE: 6

Gln Pro Ser Val Tyr Val Leu Pro Pro Ser Arg Glu Glu Leu Ser Lys
1               5                   10                  15

Asn Thr Val Ser Leu Thr Cys Leu Ile Lys Asp Phe Phe Pro Pro Asp
            20                  25                  30

Ile Asp Val Glu Trp Gln Ser Asn Gly Gln Gln Glu Pro Glu Ser Lys
        35                  40                  45

Tyr Arg Thr Thr Pro Pro Gln Leu Asp Glu Asp Gly Ser Tyr Phe Leu
            50                  55                  60

Tyr Ser Lys Leu Ser Val Asp Lys Ser Arg Trp Gln Arg Gly Asp Thr
 65                  70                  75                  80

Phe Ile Cys Ala Val Met His Glu Ala Leu His Asn His Tyr Thr Gln
                85                  90                  95

Glu Ser Leu Ser His Ser Pro Gly Lys
            100                 105

<210> SEQ ID NO 7
<211> LENGTH: 105
<212> TYPE: PRT
<213> ORGANISM: Canine

<400> SEQUENCE: 7

Gln Pro Asn Val Tyr Val Leu Pro Pro Ser Arg Asp Glu Met Ser Lys
 1               5                  10                  15

Asn Thr Val Thr Leu Thr Cys Leu Val Lys Asp Phe Phe Pro Pro Glu
                20                  25                  30

Ile Asp Val Glu Trp Gln Ser Asn Gly Gln Gln Glu Pro Glu Ser Lys
            35                  40                  45

Tyr Arg Met Thr Pro Pro Gln Leu Asp Glu Asp Gly Ser Tyr Phe Leu
    50                  55                  60

Tyr Ser Lys Leu Ser Val Asp Lys Ser Arg Trp Gln Arg Gly Asp Thr
 65                 70                  75                  80

Phe Ile Cys Ala Val Met His Glu Ala Leu His Asn His Tyr Thr Gln
                85                  90                  95

Ile Ser Leu Ser His Ser Pro Gly Lys
            100                 105

<210> SEQ ID NO 8
<211> LENGTH: 106
<212> TYPE: PRT
<213> ORGANISM: Canine

<400> SEQUENCE: 8

Gln Pro Ser Val Tyr Val Leu Pro Pro Pro Lys Glu Leu Ser Ser
 1               5                  10                  15

Ser Asp Thr Val Thr Leu Thr Cys Leu Ile Lys Asp Phe Phe Pro Pro
                20                  25                  30

Glu Ile Asp Val Glu Trp Gln Ser Asn Gly Gln Pro Glu Pro Glu Ser
            35                  40                  45

Lys Tyr His Thr Thr Ala Pro Gln Leu Asp Glu Asp Gly Ser Tyr Phe
    50                  55                  60

Leu Tyr Ser Lys Leu Ser Val Asp Lys Ser Arg Trp Gln Gln Gly Asp
 65                 70                  75                  80

Thr Phe Thr Cys Ala Val Met His Glu Ala Leu Gln Asn His Tyr Thr
                85                  90                  95

Asp Leu Ser Leu Ser His Ser Pro Gly Lys
            100                 105

<210> SEQ ID NO 9
<211> LENGTH: 220
<212> TYPE: PRT
<213> ORGANISM: Canine

<400> SEQUENCE: 9

-continued

```
Val Pro Glu Pro Leu Gly Gly Pro Ser Val Leu Ile Phe Pro Pro Lys
1               5                   10                  15

Pro Lys Asp Ile Leu Arg Ile Thr Arg Thr Pro Glu Val Thr Cys Val
            20                  25                  30

Val Leu Asp Leu Gly Arg Glu Asp Pro Glu Val Gln Ile Ser Trp Phe
        35                  40                  45

Val Asp Gly Lys Glu Val His Thr Ala Lys Thr Gln Ser Arg Glu Gln
    50                  55                  60

Gln Phe Asn Gly Thr Tyr Arg Val Val Ser Val Leu Pro Ile Glu His
65                  70                  75                  80

Gln Asp Trp Leu Thr Gly Lys Glu Phe Lys Cys Arg Val Asn His Ile
                85                  90                  95

Asp Leu Pro Ser Pro Ile Glu Arg Thr Ile Ser Lys Ala Arg Gly Arg
            100                 105                 110

Ala His Lys Pro Ser Val Tyr Val Leu Pro Pro Ser Pro Lys Glu Leu
        115                 120                 125

Ser Ser Ser Asp Thr Val Ser Ile Thr Cys Leu Ile Lys Asp Phe Tyr
    130                 135                 140

Pro Pro Asp Ile Asp Val Glu Trp Gln Ser Asn Gly Gln Gln Glu Pro
145                 150                 155                 160

Glu Arg Lys His Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Gln
            180                 185                 190

Gly Asp Pro Phe Thr Cys Ala Val Met His Glu Thr Leu Gln Asn His
        195                 200                 205

Tyr Thr Asp Leu Ser Leu Ser His Ser Pro Gly Lys
    210                 215                 220

<210> SEQ ID NO 10
<211> LENGTH: 219
<212> TYPE: PRT
<213> ORGANISM: Canine

<400> SEQUENCE: 10

Ala Pro Glu Met Leu Gly Gly Pro Ser Val Phe Ile Phe Pro Pro Lys
1               5                   10                  15

Pro Lys Asp Thr Leu Leu Ile Ala Arg Thr Pro Glu Val Thr Cys Val
            20                  25                  30

Val Val Asp Leu Asp Pro Glu Asp Pro Glu Val Gln Ile Ser Trp Phe
        35                  40                  45

Val Asp Gly Lys Gln Met Gln Thr Ala Lys Thr Gln Pro Arg Glu Glu
    50                  55                  60

Gln Phe Asn Gly Thr Tyr Arg Val Val Ser Val Leu Pro Ile Gly His
65                  70                  75                  80

Gln Asp Trp Leu Lys Gly Lys Gln Phe Thr Cys Lys Val Asn Asn Lys
                85                  90                  95

Ala Leu Pro Ser Pro Ile Glu Arg Thr Ile Ser Lys Ala Arg Gly Gln
            100                 105                 110

Ala His Gln Pro Ser Val Tyr Val Leu Pro Pro Ser Arg Glu Glu Leu
        115                 120                 125

Ser Lys Asn Thr Val Ser Leu Thr Cys Leu Ile Lys Asp Phe Phe Pro
    130                 135                 140

Pro Asp Ile Asp Val Glu Trp Gln Ser Asn Gly Gln Gln Glu Pro Glu
145                 150                 155                 160
```

-continued

Ser Lys Tyr Arg Thr Thr Pro Pro Gln Leu Asp Glu Asp Gly Ser Tyr
            165                 170                 175

Phe Leu Tyr Ser Lys Leu Ser Val Asp Lys Ser Arg Trp Gln Arg Gly
            180                 185                 190

Asp Thr Phe Ile Cys Ala Val Met His Glu Ala Leu His Asn His Tyr
            195                 200                 205

Thr Gln Glu Ser Leu Ser His Ser Pro Gly Lys
    210                 215

<210> SEQ ID NO 11
<211> LENGTH: 219
<212> TYPE: PRT
<213> ORGANISM: Canine

<400> SEQUENCE: 11

Gly Cys Gly Leu Leu Gly Gly Pro Ser Val Phe Ile Phe Pro Pro Lys
1               5                   10                  15

Pro Lys Asp Ile Leu Val Thr Ala Arg Thr Pro Thr Val Thr Cys Val
            20                  25                  30

Val Val Asp Leu Asp Pro Glu Asn Pro Glu Val Gln Ile Ser Trp Phe
        35                  40                  45

Val Asp Ser Lys Gln Val Gln Thr Ala Asn Thr Gln Pro Arg Glu Glu
    50                  55                  60

Gln Ser Asn Gly Thr Tyr Arg Val Val Ser Val Leu Pro Ile Gly His
65                  70                  75                  80

Gln Asp Trp Leu Ser Gly Lys Gln Phe Lys Cys Lys Val Asn Asn Lys
                85                  90                  95

Ala Leu Pro Ser Pro Ile Glu Glu Ile Ile Ser Lys Thr Pro Gly Gln
            100                 105                 110

Ala His Gln Pro Asn Val Tyr Val Leu Pro Pro Ser Arg Asp Glu Met
        115                 120                 125

Ser Lys Asn Thr Val Thr Leu Thr Cys Leu Val Lys Asp Phe Phe Pro
    130                 135                 140

Pro Glu Ile Asp Val Glu Trp Gln Ser Asn Gly Gln Gln Glu Pro Glu
145                 150                 155                 160

Ser Lys Tyr Arg Met Thr Pro Pro Gln Leu Asp Glu Asp Gly Ser Tyr
            165                 170                 175

Phe Leu Tyr Ser Lys Leu Ser Val Asp Lys Ser Arg Trp Gln Arg Gly
            180                 185                 190

Asp Thr Phe Ile Cys Ala Val Met His Glu Ala Leu His Asn His Tyr
            195                 200                 205

Thr Gln Ile Ser Leu Ser His Ser Pro Gly Lys
    210                 215

<210> SEQ ID NO 12
<211> LENGTH: 220
<212> TYPE: PRT
<213> ORGANISM: Canine

<400> SEQUENCE: 12

Val Pro Glu Ser Leu Gly Gly Pro Ser Val Phe Ile Phe Pro Pro Lys
1               5                   10                  15

Pro Lys Asp Ile Leu Arg Ile Thr Arg Thr Pro Glu Ile Thr Cys Val
            20                  25                  30

Val Leu Asp Leu Gly Arg Glu Asp Pro Glu Val Gln Ile Ser Trp Phe
        35                  40                  45

Val Asp Gly Lys Glu Val His Thr Ala Lys Thr Gln Pro Arg Glu Gln
            50                  55                  60

Gln Phe Asn Ser Thr Tyr Arg Val Val Ser Val Leu Pro Ile Glu His
 65                  70                  75                  80

Gln Asp Trp Leu Thr Gly Lys Glu Phe Lys Cys Arg Val Asn His Ile
                 85                  90                  95

Gly Leu Pro Ser Pro Ile Glu Arg Thr Ile Ser Lys Ala Arg Gly Gln
            100                 105                 110

Ala His Gln Pro Ser Val Tyr Val Leu Pro Pro Ser Pro Lys Glu Leu
        115                 120                 125

Ser Ser Ser Asp Thr Val Thr Leu Thr Cys Leu Ile Lys Asp Phe Phe
130                 135                 140

Pro Pro Glu Ile Asp Val Glu Trp Gln Ser Asn Gly Gln Pro Glu Pro
145                 150                 155                 160

Glu Ser Lys Tyr His Thr Thr Ala Pro Gln Leu Asp Glu Asp Gly Ser
                165                 170                 175

Tyr Phe Leu Tyr Ser Lys Leu Ser Val Asp Lys Ser Arg Trp Gln Gln
            180                 185                 190

Gly Asp Thr Phe Thr Cys Ala Val Met His Glu Ala Leu Gln Asn His
        195                 200                 205

Tyr Thr Asp Leu Ser Leu Ser His Ser Pro Gly Lys
    210                 215                 220

<210> SEQ ID NO 13
<211> LENGTH: 468
<212> TYPE: PRT
<213> ORGANISM: Canine

<400> SEQUENCE: 13

Met Glu Ser Val Phe Cys Trp Val Phe Leu Val Val Ile Leu Lys Gly
 1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Ser Tyr Tyr Met His Trp Ile Arg Gln Ala Pro Gly Lys Gly Leu
 50                  55                  60

Gln Arg Val Ala His Ile Arg Gly Asp Gly Arg Thr Thr His Tyr Ala
 65                  70                  75                  80

Asp Ala Met Lys Gly Arg Phe Thr Ile Ser Arg Asp Asn Ala Lys Asn
                 85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
        115                 120                 125

Gln Gly Thr Leu Val Thr Val Ser Ser Ala Ser Thr Thr Ala Pro Ser
130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

Ser Trp Asn Ser Gly Ser Leu Thr Ser Gly Val His Thr Phe Pro Ser
            180                 185                 190

Val Leu Gln Ser Ser Gly Leu His Ser Leu Ser Ser Met Val Thr Val

```
              195                 200                 205
    Pro Ser Ser Arg Trp Pro Ser Glu Thr Phe Thr Cys Asn Val Val His
        210                 215                 220

Pro Ala Ser Asn Thr Lys Val Asp Lys Pro Val Phe Asn Glu Cys Arg
    225                 230                 235                 240

Cys Thr Asp Thr Pro Pro Cys Pro Val Pro Glu Pro Leu Gly Gly Pro
                    245                 250                 255

Ser Val Leu Ile Phe Pro Pro Lys Pro Lys Asp Ile Leu Arg Ile Thr
                260                 265                 270

Arg Thr Pro Glu Val Thr Cys Val Val Leu Asp Leu Gly Arg Glu Asp
            275                 280                 285

Pro Glu Val Gln Ile Ser Trp Phe Val Asp Gly Lys Glu Val His Thr
        290                 295                 300

Ala Lys Thr Gln Ser Arg Glu Gln Gln Phe Asn Gly Thr Tyr Arg Val
    305                 310                 315                 320

Val Ser Val Leu Pro Ile Glu His Gln Asp Trp Leu Thr Gly Lys Glu
                    325                 330                 335

Phe Lys Cys Arg Val Asn His Ile Asp Leu Pro Ser Pro Ile Glu Arg
                340                 345                 350

Thr Ile Ser Lys Ala Arg Gly Arg Ala His Lys Pro Ser Val Tyr Val
            355                 360                 365

Leu Pro Pro Ser Pro Lys Glu Leu Ser Ser Ser Asp Thr Val Ser Ile
        370                 375                 380

Thr Cys Leu Ile Lys Asp Phe Tyr Pro Pro Asp Ile Asp Val Glu Trp
    385                 390                 395                 400

Gln Ser Asn Gly Gln Gln Glu Pro Glu Arg Lys His Arg Met Thr Pro
                    405                 410                 415

Pro Gln Leu Asp Glu Asp Gly Ser Tyr Phe Leu Tyr Ser Lys Leu Ser
                420                 425                 430

Val Asp Lys Ser Arg Trp Gln Gln Gly Asp Pro Phe Thr Cys Ala Val
            435                 440                 445

Met His Glu Thr Leu Gln Asn His Tyr Thr Asp Leu Ser Leu Ser His
        450                 455                 460

Ser Pro Gly Lys
    465

<210> SEQ ID NO 14
<211> LENGTH: 96
<212> TYPE: PRT
<213> ORGANISM: Canine

<400> SEQUENCE: 14

Leu Phe Thr Arg Thr Lys Arg Arg Ser Asp Val Ser Trp Gly Asn Thr
    1               5                   10                  15

Gly Ser Ser Gln Thr Val Ile Arg Ala Ser Val Ala Ser Trp Ser Arg
                    20                  25                  30

Asn Gly Asp Leu Tyr Ala Pro Lys Pro Lys Arg Glu Asn Gly Arg Val
                35                  40                  45

Pro Arg Pro Pro Asp Cys Lys Ala Met Phe Thr Leu Leu Ala Val Asp
        50                  55                  60

Pro Gln Met Gln Pro Glu Gly Lys Gln Thr Lys Asn Lys Ala Gln Gln
    65                  70                  75                  80

Arg Glu Lys Asn Leu Phe Ser Tyr Thr Arg Thr Ile Ala His Gln Glu
                    85                  90                  95
```

<210> SEQ ID NO 15
<211> LENGTH: 105
<212> TYPE: PRT
<213> ORGANISM: Canine

<400> SEQUENCE: 15

Leu Tyr Ala Asp Cys Ala Ser Val Ser Pro Trp Thr Tyr Ser Asp Ile
1               5                   10                  15

Tyr Ser Val Arg Ala Val Ala Ala Pro Tyr Asp Ser His Tyr Met Pro
            20                  25                  30

Ser Leu Phe Gln Ile Val Tyr Ala Thr Ala Lys Glu Lys Cys Asn Cys
        35                  40                  45

Asn Asn Cys Gly Cys Gly Leu Phe Val Thr Ala Thr Val Asp Pro Asn
    50                  55                  60

Ser Gln Gln Asn Pro Glu Ser Gly Ser Gln Lys Asn Lys Ala Glu Ile
65                  70                  75                  80

Thr Pro Gln Gln Asn Arg Asp Met Lys Asn Thr Leu Val Phe Glu Ser
                85                  90                  95

Tyr Met Arg Thr Ile Ala His Gln Ile
            100                 105

<210> SEQ ID NO 16
<211> LENGTH: 66
<212> TYPE: PRT
<213> ORGANISM: Canine

<400> SEQUENCE: 16

Leu Ser Asp Gly Ser Val Ser Trp Ala Val Ser Asn Arg Asp Tyr Ser
1               5                   10                  15

Lys Ala Ile His Val Thr Gly Val Trp Pro Arg His Met His Asn Ser
            20                  25                  30

Leu Phe Tyr Thr Pro Lys Ser Thr Lys Cys Ile Ser Pro Glu Ser Phe
        35                  40                  45

Ile Pro Ser Gly Gln Gln Thr Leu Phe Glu Pro Ser Tyr His Thr Ala
    50                  55                  60

Thr Ala
65

<210> SEQ ID NO 17
<211> LENGTH: 17
<212> TYPE: PRT
<213> ORGANISM: Canine

<400> SEQUENCE: 17

Phe Asn Glu Cys Arg Cys Thr Asp Thr Pro Pro Cys Pro Val Pro Glu
1               5                   10                  15

Pro

<210> SEQ ID NO 18
<211> LENGTH: 22
<212> TYPE: PRT
<213> ORGANISM: Canine

<400> SEQUENCE: 18

Pro Lys Arg Glu Asn Gly Arg Val Pro Arg Pro Asp Cys Pro Lys
1               5                   10                  15

Cys Pro Ala Pro Glu Met
            20

<210> SEQ ID NO 19
<211> LENGTH: 20
<212> TYPE: PRT
<213> ORGANISM: Canine

<400> SEQUENCE: 19

Ala Lys Glu Cys Glu Cys Lys Cys Asn Cys Asn Asn Cys Pro Cys Pro
1               5                   10                  15

Gly Cys Gly Leu
            20

<210> SEQ ID NO 20
<211> LENGTH: 17
<212> TYPE: PRT
<213> ORGANISM: Canine

<400> SEQUENCE: 20

Pro Lys Glu Ser Thr Cys Lys Cys Ile Ser Pro Cys Pro Val Pro Glu
1               5                   10                  15

Ser

<210> SEQ ID NO 21
<211> LENGTH: 17
<212> TYPE: PRT
<213> ORGANISM: Canine

<400> SEQUENCE: 21

Pro Lys Glu Ser Thr Cys Lys Cys Ile Pro Pro Cys Pro Val Pro Glu
1               5                   10                  15

Ser

<210> SEQ ID NO 22
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 22

Gly Gly Gly Ser
1

<210> SEQ ID NO 23
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 23

Ser Gly Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 24

Gly Gly Gly Gly Ser
1               5

```
<210> SEQ ID NO 25
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 25

Ser Gly Gly Gly Gly
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 26

Gly Gly Gly Gly Gly Ser
1               5

<210> SEQ ID NO 27
<211> LENGTH: 6
<212> TYPE: PRT
<213> ORGANISM: Artificial  Sequence
<220> FEATURE:
<223> OTHER INFORMATION: synthetic polypeptide

<400> SEQUENCE: 27

Ser Gly Gly Gly Gly Gly
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 28

Gly Gly Gly Gly Gly Gly Ser
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 29

Ser Gly Gly Gly Gly Gly Gly
1               5
```

COMPOSITIONS FOR INCREASING HALF-LIFE OF A THERAPEUTIC AGENT IN CANINES AND METHODS OF USE

CROSS-REFERENCE TO RELATED APPLICATIONS

This application is a continuation of U.S. patent application Ser. No. 16/733,105, filed Jan. 2, 2020, which claims the benefit of priority of U.S. Provisional Appl. No. 62/788,035, filed Jan. 3, 2019, the contents of which are incorporated by reference herein in its entirety.

FIELD

This disclosure relates generally to polypeptides (e.g., fusion polypeptides such as polypeptide-Fc region fusions; or binding molecules such as antibodies or ligand-binding portions of receptor-Fc fusions) that have increased half-life in canines compared to their wild type counterparts.

BACKGROUND

The Fc region of antibodies plays a number of functional roles, including, but not limited to, protecting the antibody from degradation through the lysosomal pathway and mediating antibody effector functions. With the increasing use of canine antibodies as therapeutic agents, there has been an enhanced focus on not just selecting an optimal Fab, but also combining it with an appropriate Fc for desired half-life and effector functions.

There is little guidance in the art relating to increasing half-life of polypeptide therapeutics (e.g., antibodies) for use in dogs. This disclosure remedies that failing by providing Fc region variants that improve the serum persistence of polypeptides (e.g., antibodies) in canines.

SUMMARY

Provided herein is a platform technology relating to canine CH2, CH3 and Fc sequences that are useful in therapeutic polypeptides. This disclosure features polypeptides that have increased binding to canine FcRn than control polypeptides (e.g., the wild type counterpart IgG canine Fc regions). In some instances, these polypeptides have increased binding to canine FcRn than control polypeptides at any pH (e.g., at any pH between about 5.0 to about 8.0). In some instances, these polypeptides have increased binding to canine FcRn than control polypeptides at pH 5.5 and/or pH 6.5. In some instances, these polypeptides can, e.g., bind to canine FcRn at a higher level at acidic pH (e.g., pH 5.5 or pH6.5) than at a neutral pH (e.g., pH 7.0, 7.1, 7.2, 7.3, 7.4, or 7.5). In some instances, these polypeptides bind to canine FcRn at a higher level at pH 5.5 than at pH 7.4. This disclosure relates, in part, to polypeptides that have increased half-life in canines than their wild type counterparts. For example, provided are binding molecules (e.g., antibodies or ligand-binding portions of receptors) with increased half-life relative to versions of these binding molecules not attached to the Fc regions (e.g., CH2, CH3, or CH2+CH3 regions) disclosed herein. Also provided are enzyme-Fc region fusions, ligand-Fc region fusions, and peptide-Fc region fusions, wherein the fusions have increased half-life compared with their wild type counterparts. The Fc regions, in addition to having a substitution or substitutions (relative to the wild type canine Fc region) that increase half-life may also include other substitutions that, e.g., increase effector function, decrease effector function, and/or decrease heterogeneity of the polypeptide (e.g., by removing one or more post-translational modifications in the Fc region). The canine CH2, CH3, and Fc region sequences can be from any canine antibody. In some instances, the canine CH2, CH3, and Fc region sequences are from a canine IgG (e.g., IgG.A, IgG.B, IgG.C, or IgG.D).

The disclosure features a recombinant protein comprising (1) a binding domain, or a fragment thereof, that specifically binds to a ligand, or an epitope of a protein, wherein the binding domain is attached to (2) a domain comprising a CH2 region, a CH3 region, or an Fc region (CH2+CH3 region) disclosed herein. In some instances, the binding domain comprises (i) the six complementarity determining regions (CDRs) of a canine or human/humanized antibody; (ii) the VH and/or VL of a canine, caninized, humanized, or human antibody; (iii) a nanobody; (iv) a scFv; (v) an Fab; or (vi) a soluble receptor-binding domain that binds a ligand, or a ligand-binding fragment thereof.

The disclosure also provides a composition comprising: (1) a first polypeptide comprising a first Fc region (e.g., a CH2 region, a CH3 region, a CH2+CH3 region) comprising a canine IgG Fc region variant described herein; and (2) a second polypeptide comprising a second Fc region comprising a canine IgG Fc region variant described herein. The first and second polypeptide can be associated through the first and second Fc regions. In some instances, the amino acid sequences of the first and second Fc regions are the same. In other instances, the amino acid sequences of the first and second Fc regions are different (e.g., by 1, 2, 3, 4, 5, 6, 7, 8, 9, 10, 11, 12, 13, 14, 15, 16, 17, 18, 19, 20, 21, 22, 23, 24, or 25 amino acids). In some instances, the Fc region variant is a variant of a canine IgG.B antibody Fc region. In some instances, the Fc region variant is a variant of a canine IgG.A antibody Fc region. In some instances, the Fc region variant is a variant of a canine IgG.C antibody Fc region. In some instances, the Fc region variant is a variant of a canine IgG.D antibody Fc region.

Also disclosed is a fusion molecule comprising a canine IgG Fc region variant disclosed herein and a polypeptide. In some embodiments, the canine IgG Fc region variant is covalently attached to the polypeptide (e.g., through a hinge region or a linker). In some instances, the polypeptide is a ligand binding domain of a canine receptor protein, an extracellular domain of a canine receptor protein, or an antigen-binding domain. In some instances, the polypeptide is selected from the ligand binding domain or extracellular domain of canine IL-13Rα1, or IL-13Rα2, canine EPO, canine CTLA4, canine LFA3, canine VEGFR1/VEGFR3, canine IL-1R, canine GLP-1 receptor agonist, and canine Thrombopoietin binding peptide. In some instances, the polypeptide is a scFv, a nanobody, or single domain antibody. In some instances, the IgG Fc region variant is a variant of a canine IgG.B antibody Fc region. In some instances, the IgG Fc region variant is a variant of a canine IgG.A antibody Fc region. In some instances, the IgG Fc region variant is a variant of a canine IgG.C antibody Fc region. In some instances, the IgG Fc region variant is a variant of a canine IgG.D antibody Fc region.

In one aspect, the disclosure provides a polypeptide or polypeptides comprising a canine IgG Fc CH2 region variant, the CH2 region variant comprising an amino acid sequence that is at least 75% identical to the sequence set forth in SEQ ID NO:1, and comprises at least one of the following:
an amino acid other than Ile at amino acid position 250,
an amino acid other than Leu at amino acid position 251, an amino acid other than Arg at amino acid position 252,
an amino acid other than Thr at amino acid position 254,
an amino acid other than Thr at amino acid position 256,
an amino acid other than His at amino acid position 285,
an amino acid other than Thr at amino acid position 286,
an amino acid other than Pro at amino acid position 307,
an amino acid other than Ile at amino acid position 308,
an amino acid other than Glu at amino acid position 309,
an amino acid other than Gln at amino acid position 311, or
an amino acid other than Thr at amino acid position 315.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH2 region in place of the IgG Fc CH2 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:1.

In one aspect, the disclosure provides a polypeptide or polypeptides comprising a canine IgG Fc CH2 region variant, the CH2 region variant comprising an amino acid sequence that is at least 75% identical to the sequence set forth in SEQ ID NO:2, and comprises at least one of the following:
an amino acid other than Thr at amino acid position 250,
an amino acid other than Leu at amino acid position 251,
an amino acid other than Leu at amino acid position 252,
an amino acid other than Ala at amino acid position 254,
an amino acid other than Thr at amino acid position 256,
an amino acid other than Gln at amino acid position 285,
an amino acid other than Thr at amino acid position 286,
an amino acid other than Pro at amino acid position 307,
an amino acid other than Ile at amino acid position 308,
an amino acid other than Gly at amino acid position 309,
an amino acid other than Gln at amino acid position 311, or
an amino acid other than Lys at amino acid position 315.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH2 region in place of the IgG Fc CH2 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:2.

In one aspect, the disclosure further provides a polypeptide or polypeptides comprising a canine IgG Fc CH2 region variant, the CH2 region variant comprising an amino acid sequence that is at least 75% identical to the sequence set forth in SEQ ID NO:3, and comprises at least one of the following:
an amino acid other than Ile at amino acid position 250,
an amino acid other than Leu at amino acid position 251,
an amino acid other than Val at amino acid position 252,
an amino acid other than Ala at amino acid position 254,
an amino acid other than Thr at amino acid position 256,
an amino acid other than Gln at amino acid position 285,
an amino acid other than Thr at amino acid position 286,
an amino acid other than Pro at amino acid position 307,
an amino acid other than Ile at amino acid position 308,
an amino acid other than Gly at amino acid position 309,
an amino acid other than Gln at amino acid position 311, or
an amino acid other than Ser at amino acid position 315, In some embodiments, the polypeptide or polypeptides has/have: increased half-life in a dog than a control polypeptide or control polypeptides, wherein the control polypeptide or control polypeptides are identical to the polypeptide or polypeptides except for having the corresponding wild type canine IgG Fc CH2 region in place of the IgG Fc CH2 region variant.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:3.

In one aspect, the disclosure is related to a polypeptide or polypeptides comprising a canine IgG Fc CH2 region variant, the CH2 region variant comprising an amino acid sequence that is at least 75% identical to the sequence set forth in SEQ ID NO:4, and comprises at least one of the following:
an amino acid other than Ile at amino acid position 250,
an amino acid other than Leu at amino acid position 251,
an amino acid other than Arg at amino acid position 252,
an amino acid other than Thr at amino acid position 254,
an amino acid other than Thr at amino acid position 256,
an amino acid other than His at amino acid position 285,
an amino acid other than Thr at amino acid position 286,
an amino acid other than Pro at amino acid position 307,
an amino acid other than Ile at amino acid position 308,
an amino acid other than Glu at amino acid position 309,
an amino acid other than Gln at amino acid position 311, or
an amino acid other than Thr at amino acid position 315.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH2 region in place of the IgG Fc CH2 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:4.

In some embodiments, the polypeptide or polypeptides comprise(s) at least one of the following:
Glu or Gln at amino acid position 250,
Asp or Glu at amino acid position 251,
Tyr at amino acid position 252,
Thr at amino acid position 254,
Asp, Glu, or Phe at amino acid position 256,
Asn or Asp at amino acid position 285,
Asp at amino acid position 286,
Arg, Gln, or Ala at amino acid position 307,
Pro at amino acid position 308,
Pro at amino acid position 309,
Val at amino acid position 311, o
Asp at amino acid position 315. r In some embodiments, the polypeptide or polypeptides comprise(s) at least one of the following:
  Tyr or Met at amino acid position 252,
  Thr at amino acid position 254, or
  Glu at amino acid position 256.

In some embodiments, the canine IgG Fc CH2 region variant comprises at least one of the following:
  (i) Tyr at amino acid position 252, Thr at amino acid position 254, and Glu at amino acid position 256;
  (ii) Leu at amino acid position 428 and Ser at amino acid position 434;
  (iii) Asp at amino acid position 256, Arg at amino acid position 307, and Val at amino acid position 311;
  (iv) Asp at amino acid position 256, Asp at amino acid position 315, and Val at amino acid position 378;
  (v) Asp at amino acid position 256, Asp at amino acid position 286, Arg at amino acid position 307, and Val at amino acid position 311;
  (vi) Asn at amino acid position 285, Gln at amino acid position 307, and Asp at amino acid position 315; or
  (vii) Asp at amino acid position 251, and Pro at amino acid position 309.

In one aspect, the disclosure provides a polypeptide or polypeptides comprising a canine IgG Fc CH3 region variant comprising an amino acid sequence that is at least 75% identical to the sequence set forth in SEQ ID NO:5, and comprises at least one of the following:
  an amino acid other than Asp at amino acid position 378,
  an amino acid other than Glu at amino acid position 380,
  an amino acid other than Met at amino acid position 428,
  an amino acid other than Glu at amino acid position 430,
  an amino acid other than Gln at amino acid position 433,
  an amino acid other than Asn at amino acid position 434,
  an amino acid other than His at amino acid position 435, or
  an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH3 region in place of the IgG Fc CH3 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:5.

In one aspect, the disclosure provides a polypeptide or polypeptides comprising a canine IgG Fc CH3 region variant comprising an amino acid sequence that is at least 75% identical to the sequence set forth in SEQ ID NO:6, and comprises at least one of the following:
  an amino acid other than Asp at amino acid position 378,
  an amino acid other than Glu at amino acid position 380,
  an amino acid other than Met at amino acid position 428,
  an amino acid other than Glu at amino acid position 430,
  an amino acid other than His at amino acid position 433,
  an amino acid other than Asn at amino acid position 434,
  an amino acid other than His at amino acid position 435, or
  an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH3 region in place of the IgG Fc CH3 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:6.

In one aspect, the disclosure provides a polypeptide or polypeptides comprising a canine IgG Fc CH3 region variant comprising an amino acid sequence that is at least 75% identical to the sequence set forth in SEQ ID NO:7, and comprises at least one of the following:
  an amino acid other than Asp at amino acid position 378,
  an amino acid other than Glu at amino acid position 380,
  an amino acid other than Met at amino acid position 428,
  an amino acid other than Glu at amino acid position 430,
  an amino acid other than His at amino acid position 433,
  an amino acid other than Asn at amino acid position 434,
  an amino acid other than His at amino acid position 435, or
  an amino acid other than Tyr at amino acid position 436.

In some embodiments, the polypeptide or polypeptides has/have: increased half-life in a dog than a control polypeptide or control polypeptides, wherein the control polypeptide or control polypeptides are identical to the polypeptide or polypeptides except for having the corresponding wild type canine IgG Fc CH3 region in place of the IgG Fc CH3 region variant.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:7.

In one aspect, the disclosure provides a polypeptide or polypeptides comprising a canine IgG Fc CH3 region variant comprising an amino acid sequence that is at least 75% identical to the sequence set forth in SEQ ID NO:8, and comprises at least one of the following:
  an amino acid other than Asp at amino acid position 378,
  an amino acid other than Glu at amino acid position 380,
  an amino acid other than Met at amino acid position 428,
  an amino acid other than Glu at amino acid position 430,
  an amino acid other than Gln at amino acid position 433,
  an amino acid other than Asn at amino acid position 434,
  an amino acid other than His at amino acid position 435,
    or an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc CH3 region in place of the IgG Fc CH3 region variant; and/or (2) increased binding to canine FcRn than the control polypeptide or polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:8.

In some embodiments, the polypeptide or polypeptides comprise(s) at least one of the following:

Val at amino acid position 378,
Ala at amino acid position 380,
Leu at amino acid position 428,
Ala or Lys at amino acid position 430,
Lys at amino acid position 433,
Ser, Ala, or Phe at amino acid position 434,
Try at amino acid position 435,
His at amino acid position 436.

In some embodiments, the canine IgG Fc CH3 region variant comprises:
(i) Leu at amino acid position 428, and Ser at amino acid position 434;
(ii) Leu at amino acid position 428, and Ala at amino acid position 434;
(iii) Lys at amino acid position 430, and Lys at amino acid position 433; or
(iv) Tyr at amino acid position 435, and His at amino acid position 436.

In some embodiments, the polypeptide or polypeptides comprise(s) Tyr, Trp, Arg, or His at amino acid position 434.

In one aspect, the disclosure provides a polypeptide or polypeptides comprising a canine IgG Fc region variant comprising an amino acid sequence that is at least 75% identical to the sequence set forth in SEQ ID NO:9, and that comprises at least one of the following:
an amino acid other than Ile at amino acid position 250,
an amino acid other than Leu at amino acid position 251,
an amino acid other than Arg at amino acid position 252,
an amino acid other than Thr at amino acid position 254,
an amino acid other than Thr at amino acid position 256,
an amino acid other than His at amino acid position 285,
an amino acid other than Thr at amino acid position 286,
an amino acid other than Pro at amino acid position 307,
an amino acid other than Ile at amino acid position 308,
an amino acid other than Glu at amino acid position 309,
an amino acid other than Gln at amino acid position 311,
an amino acid other than Thr at amino acid position 315,
an amino acid other than Asp at amino acid position 378,
an amino acid other than Glu at amino acid position 380,
an amino acid other than Met at amino acid position 428,
an amino acid other than Glu at amino acid position 430,
an amino acid other than Gln at amino acid position 433,
an amino acid other than Asn at amino acid position 434,
an amino acid other than His at amino acid position 435, or
an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant; and/or (2) increased binding to canine FcRn than the control polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:9.

In one aspect, the disclosure also provides a polypeptide or polypeptides comprising a canine IgG Fc region variant comprising an amino acid sequence that is at least 75% identical to the sequence set forth in SEQ ID NO:10, and that comprises at least one of the following:
an amino acid other than Thr at amino acid position 250,
an amino acid other than Leu at amino acid position 251,
an amino acid other than Leu at amino acid position 252,
an amino acid other than Ala at amino acid position 254,
an amino acid other than Thr at amino acid position 256,
an amino acid other than Gln at amino acid position 285,
an amino acid other than Thr at amino acid position 286,
an amino acid other than Pro at amino acid position 307,
an amino acid other than Ile at amino acid position 308,
an amino acid other than Gly at amino acid position 309,
an amino acid other than Gln at amino acid position 311,
an amino acid other than Lys at amino acid position 315,
an amino acid other than Asp at amino acid position 378,
an amino acid other than Glu at amino acid position 380,
an amino acid other than Met at amino acid position 428,
an amino acid other than Glu at amino acid position 430,
an amino acid other than His at amino acid position 433,
an amino acid other than Asn at amino acid position 434,
an amino acid other than His at amino acid position 435, or
an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant; and/or (2) increased binding to canine FcRn than the control polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:10.

In one aspect, the disclosure provides a polypeptide or polypeptides comprising a canine IgG Fc region variant comprising an amino acid sequence that is at least 75% identical to the sequence set forth in SEQ ID NO:11, and that comprises at least one of the following:
an amino acid other than Ile at amino acid position 250,
an amino acid other than Leu at amino acid position 251,
an amino acid other than Val at amino acid position 252,
an amino acid other than Ala at amino acid position 254,
an amino acid other than Thr at amino acid position 256,
an amino acid other than Gln at amino acid position 285,
an amino acid other than Thr at amino acid position 286,
an amino acid other than Pro at amino acid position 307,
an amino acid other than Ile at amino acid position 308,
an amino acid other than Gly at amino acid position 309,
an amino acid other than Gln at amino acid position 311,
an amino acid other than Ser at amino acid position 315,
an amino acid other than Asp at amino acid position 378,
an amino acid other than Glu at amino acid position 380,
an amino acid other than Met at amino acid position 428,
an amino acid other than Glu at amino acid position 430,
an amino acid other than His at amino acid position 433,
an amino acid other than Asn at amino acid position 434,
an amino acid other than His at amino acid position 435,
or an amino acid other than Tyr at amino acid position 436.

In some embodiments, the polypeptide or polypeptides has/have: increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:11.

In one aspect, the disclosure provides a polypeptide or polypeptides comprising a canine IgG Fc region variant comprising an amino acid sequence that is at least 75% identical to the sequence set forth in SEQ ID NO:12, and that comprises at least one of the following:

an amino acid other than Ile at amino acid position 250,
an amino acid other than Leu at amino acid position 251,
an amino acid other than Arg at amino acid position 252,
an amino acid other than Thr at amino acid position 254,
an amino acid other than Thr at amino acid position 256,
an amino acid other than His at amino acid position 285,
an amino acid other than Thr at amino acid position 286,
an amino acid other than Pro at amino acid position 307,
an amino acid other than Ile at amino acid position 308,
an amino acid other than Glu at amino acid position 309,
an amino acid other than Gln at amino acid position 311,
an amino acid other than Thr at amino acid position 315,
an amino acid other than Asp at amino acid position 378,
an amino acid other than Glu at amino acid position 380,
an amino acid other than Met at amino acid position 428,
an amino acid other than Glu at amino acid position 430,
an amino acid other than Gln at amino acid position 433,
an amino acid other than Asn at amino acid position 434,
an amino acid other than His at amino acid position 435, or
an amino acid other than Tyr at amino acid position 436.

In some embodiments, the polypeptide or polypeptides has/have: (1) increased half-life in a dog than a control polypeptide or control polypeptides, wherein the control polypeptide or control polypeptides are identical to the polypeptide or polypeptides except for having the corresponding wild type canine IgG Fc region in place of the IgG Fc region variant; and/or (2) increased binding to canine FcRn than the control polypeptides; and wherein the amino acid positions are based on EU numbering.

In some embodiments, the amino acid sequence is at least 80%, at least 85%, at least 90%, at least 95%, at least 96%, at least 97%, at least 98%, at least 99%, or 100% identical to the sequence set forth in SEQ ID NO:12.

In some embodiments, the polypeptide or polypeptides comprise at least one of the following:

Glu or Gln at amino acid position 250,
Asp or Glu at amino acid position 251,
Tyr at amino acid position 252,
Thr at amino acid position 254,
Asp, Glu, or Phe at amino acid position 256,
Asn or Asp at amino acid position 285,
Asp at amino acid position 286,
Arg, Gln, or Ala at amino acid position 307,
Pro at amino acid position 308,
Pro at amino acid position 309,
Val at amino acid position 311,
Asp at amino acid position 315,
Val at amino acid position 378,
Ala at amino acid position 380,
Leu at amino acid position 428,
Ala or Lys at amino acid position 430,
Lys at amino acid position 433,
Ser, Ala, or Phe at amino acid position 434,
Try at amino acid position 435, or
His at amino acid position 436.

In some embodiments, the polypeptide or polypeptides comprise(s) at least one of the following:

Tyr or Met at amino acid position 252,
Thr at amino acid position 254,
Glu at amino acid position 256, or
Tyr, Trp, Arg, or His at amino acid position 434.

In some embodiments, the canine IgG Fc region variant comprises at least one of the following:

(i) Tyr at amino acid position 252, Thr at amino acid position 254, and Glu at amino acid position 256;
(ii) Leu at amino acid position 428 and Ser at amino acid position 434;
(iii) Asp at amino acid position 256, Arg at amino acid position 307, and Val at amino acid position 311;
(iv) Asp at amino acid position 256, Asp at amino acid position 315, and Val at amino acid position 378;
(v) Asp at amino acid position 256, Asp at amino acid position 286, Arg at amino acid position 307, and Val at amino acid position 311;
(vi) Asn at amino acid position 285, Gln at amino acid position 307, and Asp at amino acid position 315;
(vii) Asp at amino acid position 256, Arg at amino acid position 307, Val at amino acid position 311, and Val at amino acid position 378;
(viii) Asp at amino acid position 285, Val at amino acid position 311, and Val at amino acid position 378;
(ix) Asp at amino acid position 256, Asp at amino acid position 285, and Val at amino acid position 378;
(x) Asp at amino acid position 256, Val at amino acid position 311, and Val at amino acid position 378;
(xi) Asp at amino acid position 256, Asp at amino acid position 285, Asp at amino acid position 286, Arg at amino acid position 307, and Val at amino acid position 378;
(xii) Asp at amino acid position 256, Asp at amino acid position 286, Arg at amino acid position 307, Val at amino acid position 311, and Val at position 378;
(xiii) Gln at amino acid position 307, Val at amino acid position 311, and Val at amino acid position 378;
(xiv) Asp at amino acid position 285, Gln at amino acid position 307, and Val at amino acid position 378;
(xv) Asp at amino acid position 256, Asp at amino acid position 285, Arg at amino acid position 307, Val at amino acid position 311, and Val at amino acid position 378;
(xvi) Gln at amino acid position 307, Ala at amino acid position 380, Ser or Ala at amino acid position 434;
(xvii) Leu at amino acid position 428, and Ser or Ala at amino acid position 434; or
(xviii) Gln at amino acid position 250 and Leu at amino acid position 428.

In some embodiments, the polypeptide or polypeptides is/are an antigen binding domain(s).

In some embodiments, the antigen binding domain(s) bind to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, TNF-alpha, IgE, PD-1, PD-1 ligand, CD3, CD20, CD47, CD52, OX40, OX40 ligand, CTLA4, VEGF, EGFR, NAV 1.7, and complement system complex (e.g., C1 complex, C2 complex, C3 complex, C4 complex, C5 complex, C6 complex, C7 complex, C8 complex, C9 complex).

In some embodiments, the antigen binding domain(s) is/are a scFv, scFab, or nanobody.

In some embodiments, the polypeptide or polypeptides described herein further comprise a protein. In some embodiments, the protein is selected from the group consisting of EPO, CTLA4, LFA3, VEGFR1/VEGFR3, IL-1R, IL-4R, GLP-1 receptor agonist, and Thrombopoietin binding peptide.

In one aspect, the disclosure provides a pharmaceutical composition comprising (i) the polypeptide or polypeptides described herein, and (ii) a pharmaceutically acceptable excipient.

In one aspect, the disclosure provides a nucleic acid or nucleic acids encoding the polypeptide or polypeptides described herein.

In one aspect, the disclosure provides an expression vector or expression vectors comprising the nucleic acid or nucleic acids described herein.

In one aspect, the disclosure provides a host cell comprising the nucleic acid or nucleic acids described herein or the expression vector or expression vectors described herein.

In one aspect, the disclosure provides a method of making a polypeptide or polypeptides, the method comprising
  (a) providing a nucleic acid or nucleic acids described herein;
  (b) expressing the nucleic acid or nucleic acids in a host cell culture, thereby producing the polypeptide or polypeptides; and
  (c) collecting the polypeptide or polypeptides produced in (b) from the host cell culture.

In some embodiments, the method further comprises formulating the polypeptide or polypeptides as a pharmaceutical formulation.

In one aspect, the disclosure provides a method of treating a canine disease or disorder in a dog in need thereof, the method comprising administering an effective amount of a composition comprising the pharmaceutical composition described herein to the dog.

In one aspect, the disclosure provides a method of preventing a canine disease or disorder in a dog in need thereof, the method comprising administering an effective amount of a composition comprising the pharmaceutical composition described herein to the dog.

In some embodiments, the disease or disorder is an allergic disease, a chronic pain, an acute pain, an inflammatory disease, an autoimmune disease, an endocrine disease, a gastrointestinal disease, a cardiovascular disease, a renal disease, a fertility related disorder, an infectious disease or a cancer.

In some embodiments, the disease or disorder is atopic dermatitis, allergic dermatitis, osteoarthritic pain, arthritis, anemia, or obesity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF DRAWINGS

FIG. 1 is an amino acid sequence alignment of canine IgGγ chains. These chains contain $V_H$, CH1, CH2, and CH3 domains and the hinge region between CH1 and CH2. An N-glycosylation site is shown in bold and marked in a block. These sequences are assigned SEQ ID NOs.: 13, 14, 15, and 16, respectively.

FIG. 2 is an amino acid sequence alignment of the CH2 region of canine IgG γ chains. These sequences are assigned SEQ ID NOs.: 1, 2, 3, and 4, respectively. Residues that are substituted to increase half-life are identified by underlines.

FIG. 3 is an amino acid sequence alignment of the CH3 region of canine IgG γ chains. These sequences are assigned SEQ ID NOs.: 5, 6, 7, and 8, respectively. Residues that are substituted to increase half-life are identified by underlines.

FIG. 4 is an amino acid sequence alignment of the Fc region of canine IgG γ chains. These sequences are assigned SEQ ID NOs.: 9, 10, 11, and 12, respectively. Residues that are substituted to increase half-life are identified by underlines.

FIGS. 5A-5C is a table provided EU numbering for the CH2 region of canine IgG.

FIGS. 6A-6C is a table provided EU numbering for the CH3 region of canine IgG.

FIGS. 15A-15F depict Biacore sensorgrams for wild type and the different variants from the NNK libraries at position 434. The lighter line represents the measured data and the darker line represents the fitted curve using a 1:1 interaction model.

DETAILED DESCRIPTION

Figure 7A:
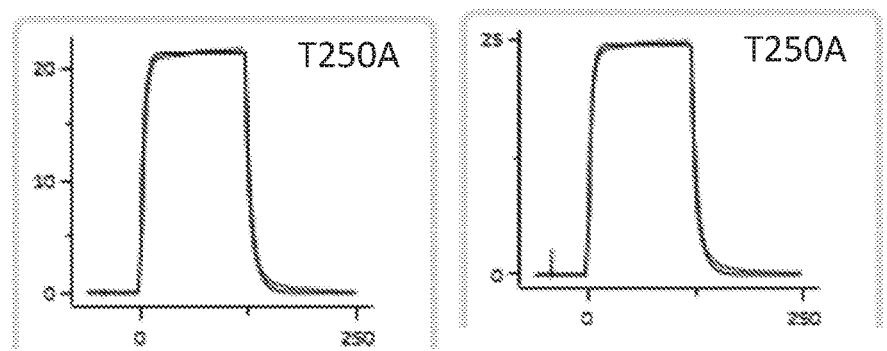
FIGS. 7A-7U depict Biacore sensorgrams from the alanine scanning mutagenesis experiment. The lighter line on each figure represents the measured data and the darker line represents the fitted curve using a 1:1 interaction model.
Figure 7B:
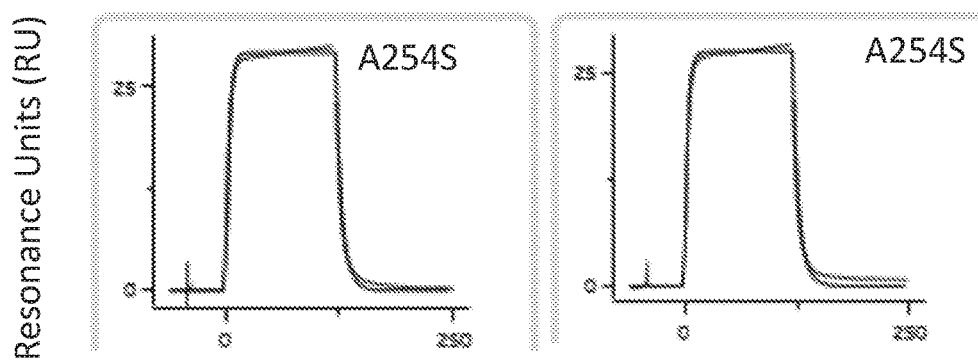
Figure 7C:
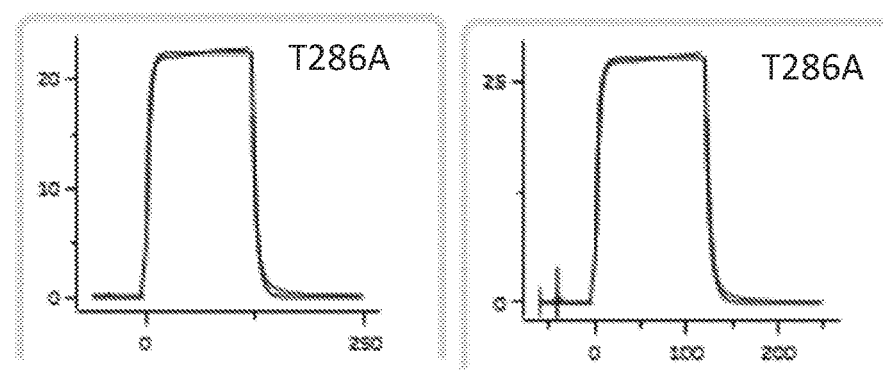
Figure 7D:
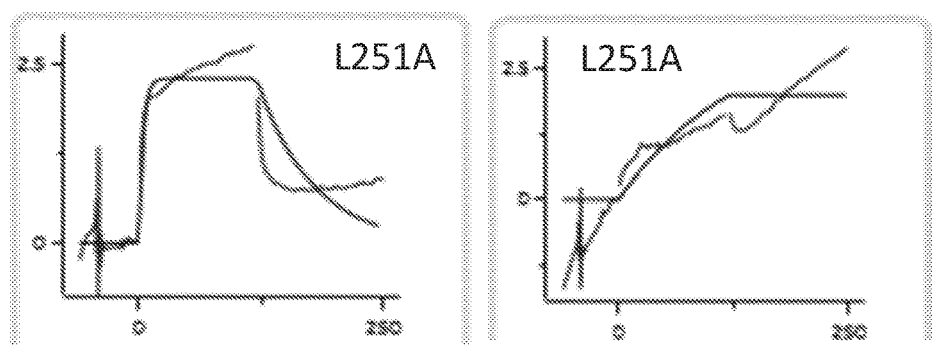
Figure 7E:
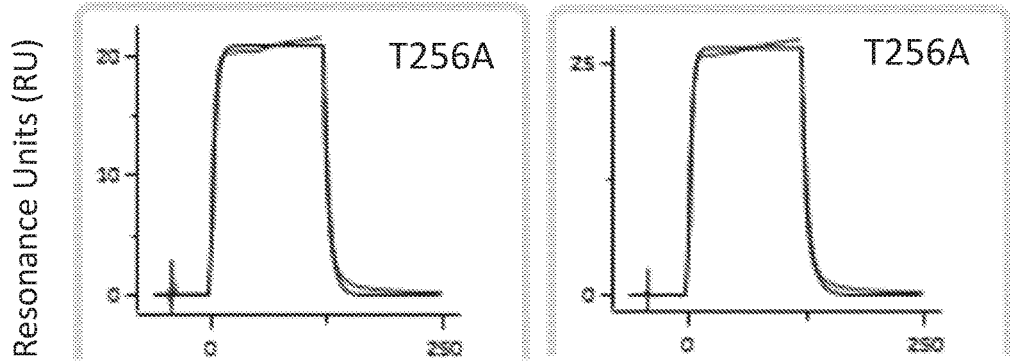
Figure 7F:
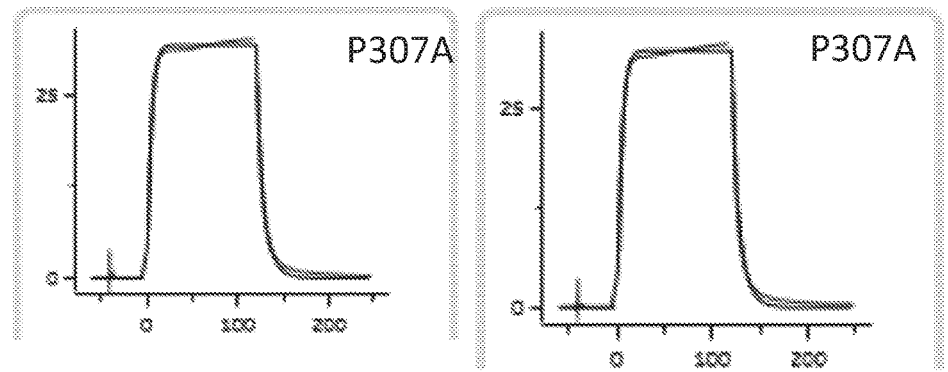
Figure 7G:
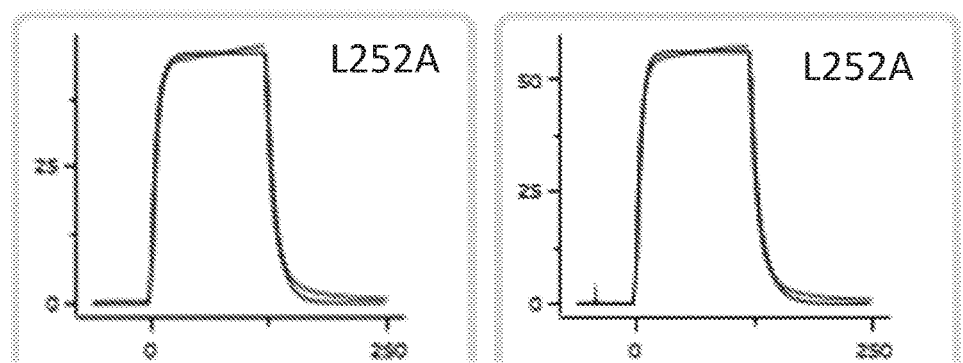
Figure 7H:
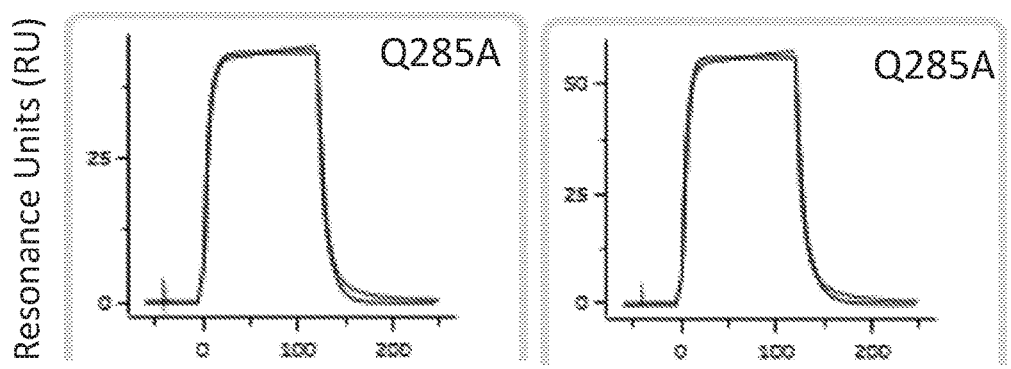
Figure 7I:
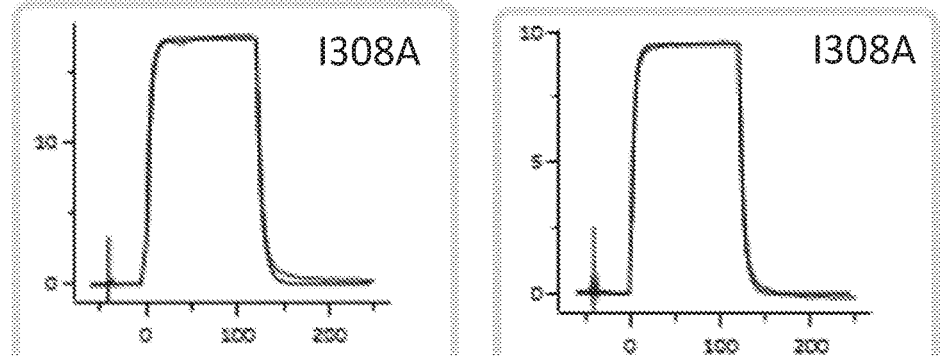
Figure 7J:
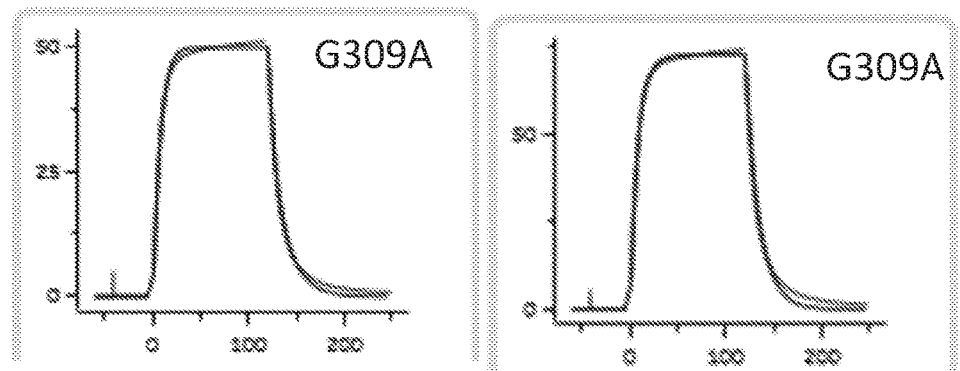
Figure 7K:
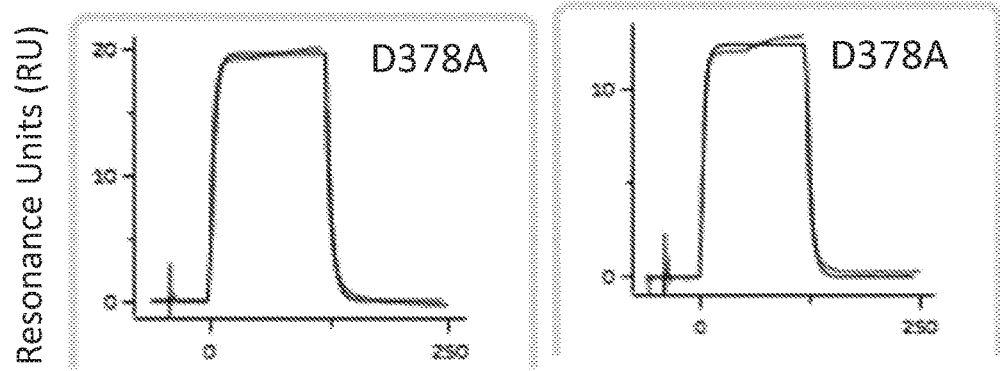
Figure 7L:
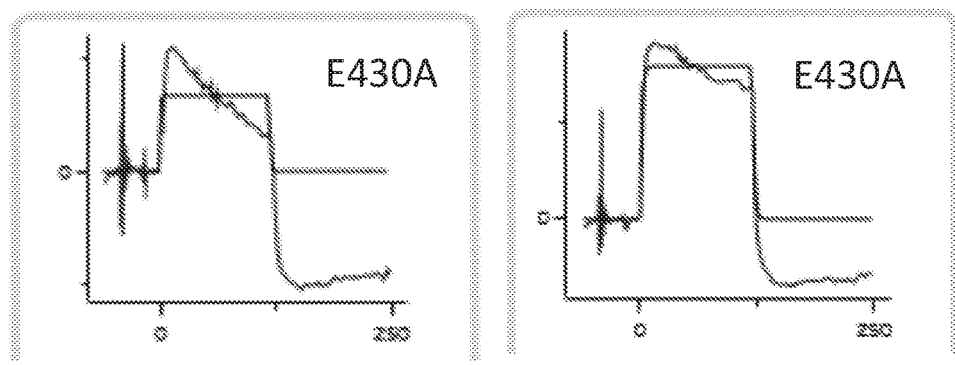
Figure 7M:
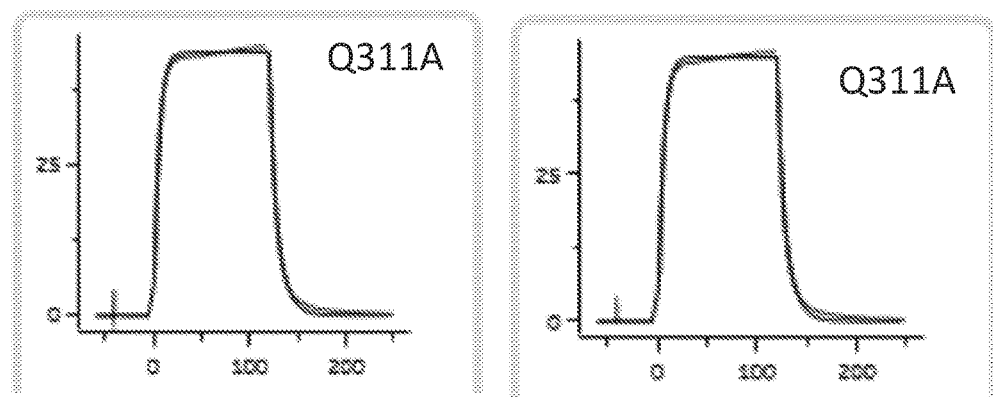
Figure 7N:
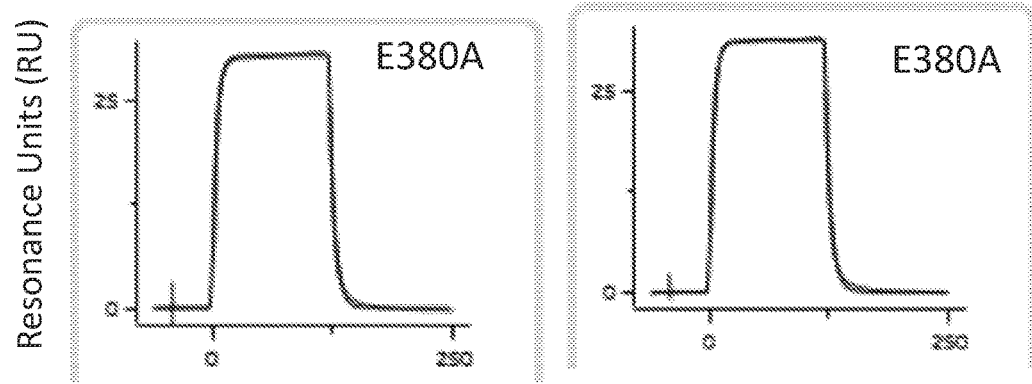
Figure 7O:
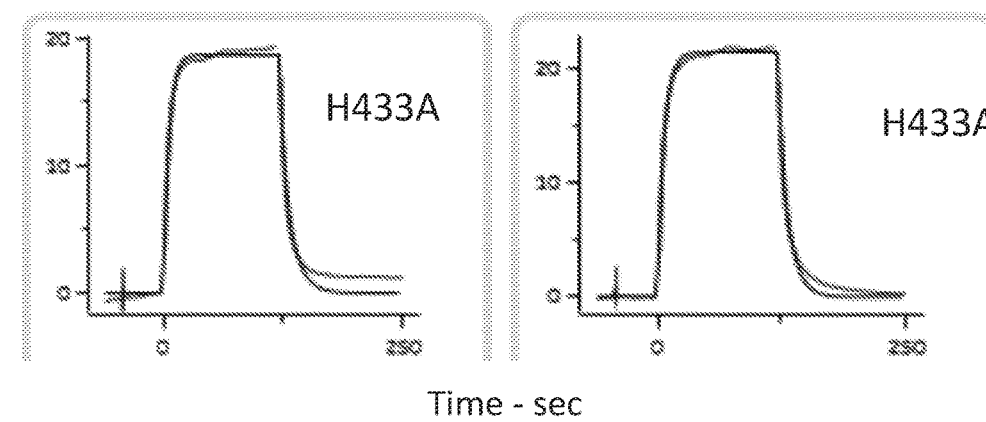
Figure 7P:
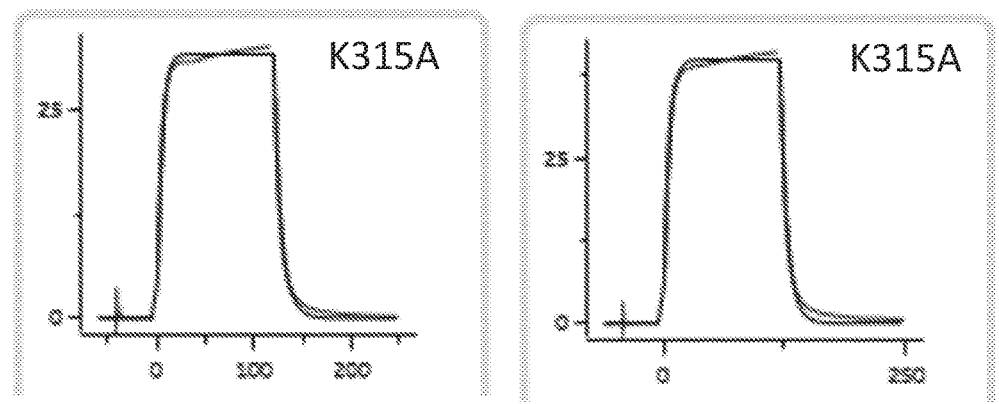
Figure 7Q:
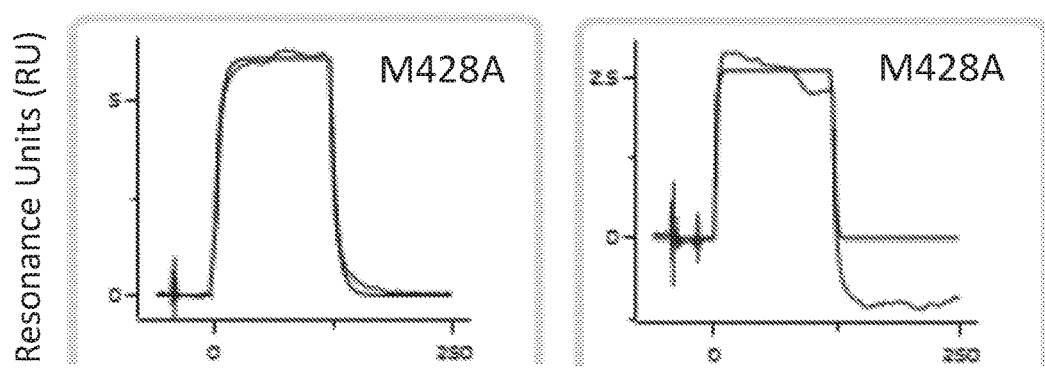
Figure 7R:
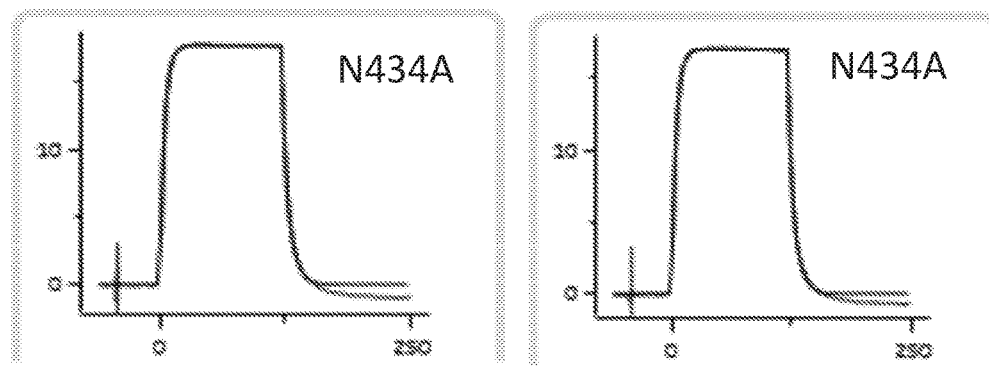
Figure 7S:
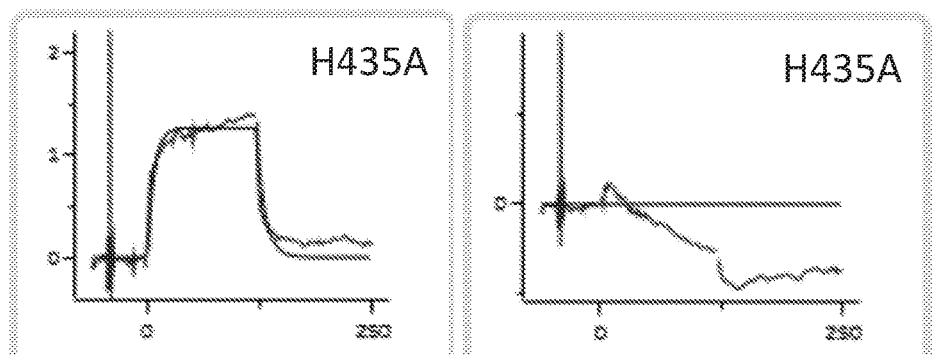
Figure 7T:
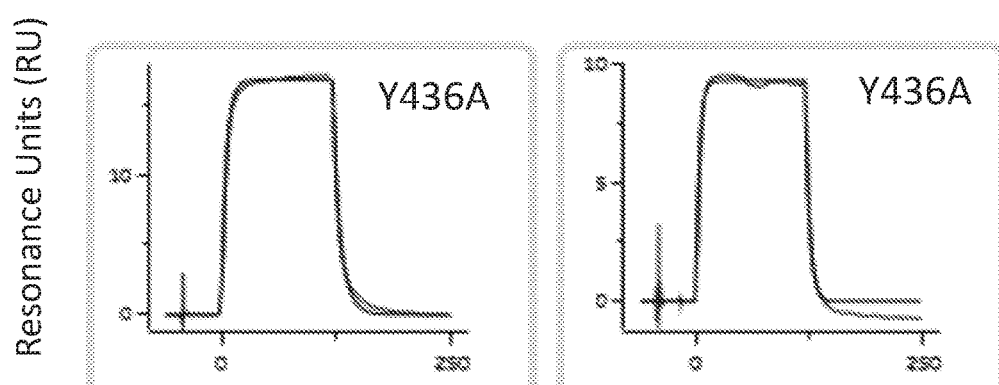

With the increasing use of polypeptide (e.g., antibodies, ligand-binding domains of receptors, enzymes, ligands, peptides) as therapeutics for the prevention and treatment of a wide variety of canine diseases, it is important to develop polypeptides with extended half-life, especially in the context of the prevention or treatment of chronic diseases in which a polypeptide must be administered repetitively.

Accordingly, this disclosure features canine immunoglobulin CH2, CH3, and Fc regions comprising mutations that enhance the half-life of a polypeptide or polypeptides comprising these sequences. Also disclosed are polypeptides comprising these domains and methods of their use. These peptides can be used for various therapeutic and diagnostic purposes.

Canine Antibodies

Dogs have four IgG heavy chains referred to as A, B, C, and D. These heavy chains represent four different subclasses of dog IgG, which are referred to as IgG.A, IgG.B, IgG.C and IgG.D. The amino acid and DNA sequences for these heavy chains are available from Tang et al., Vet. Immunol. Immunopathol., 80: 259-270 (2001) and the GENBANK database. For example, the amino acid sequence of IgG.A heavy chain has GENBANK accession number AAL35301.1, IgG.B has GENBANK accession number AAL35302.1, IgG.C has GENBANK accession number AAL35303.1, and IgG.D has GENBANK accession number AAL35304.1. Canine antibodies also include two types of light chains: kappa and lambda. The DNA and amino acid sequence of these light chains can also be obtained from GENBANK database. For example, the dog kappa light chain amino acid sequence has accession number ABY 57289.1 and the dog lambda light chain has accession number ABY 55569.1.

CH2 Region of a Canine Fc region:

The CH2 region of a canine antibody comprises or consists of amino acids 237 to 340 (according to EU numbering) of a canine IgG antibody. It is to be understood that the CH2 region may include one to six (e.g., 1, 2, 3, 4, 5, 6) additional amino acids or deletions at their N and/or C-terminus.

The amino acid sequence of the CH2 region of canine IgG.A is provided below:

```
                                           (SEQ ID NO: 1)
GPSVLI FPPKPKDILR ITRTPEVTCV VLDLGREDPE

VQISWFVDGK EVHTAKTQSR EQQFNGTYRV VSVLPIEHQD

WLTGKEFKCR VNHIDLPSPI ERTISKAR
```

The amino acid sequence of the CH2 domain of canine IgG.B is provided below:

```
                                           (SEQ ID NO: 2)
GPSVFIFPPK PKDTLLIART PEVTCVVVDL DPEDPEVQIS

WFVDGKQMQT AKTQPREEQF NGTYRVVSVL PIGHQDWLKG

KQFTCKVNNK ALPSPIERTI SKAR
```

The amino acid sequence of the CH2 domain of canine IgG.C is provided below:

```
                                           (SEQ ID NO: 3)
GPSVFIFPP KPKDILVTAR TPTVTCVVVD LDPENPEVQI

SWFVDSKQVQ TANTQPREEQ SNGTYRVVSV LPIGHQDWLS

GKQFKCKVNN KALPSPIEEI ISKTP
```

The amino acid sequence of the CH2 domain of canine IgG.D is provided below:

```
                                           (SEQ ID NO: 4)
GPSV FIFPPKPKDI LRITRTPEIT CVVLDLGRED

PEVQISWFVD GKEVHTAKTQ PREQQFNSTY RVVSVLPIEH

QDWLTGKEFK CRVNHIGLPS PIERTISKAR
```

CH3 Region of a Canine Fc region:

The CH3 region of a canine antibody comprises or consists of amino acids 345 to 447 (according to EU numbering) of a canine IgG antibody. It is to be understood that the CH3 region may include one to six (e.g., 1, 2, 3, 4, 5, 6) additional amino acids or deletions at their N and/or C-terminus.

The amino acid sequence of the CH3 domain of canine IgG.A is provided below:

```
                                           (SEQ ID NO: 5)
KPSVYVLP PSPKELSSSD TVSITCLIKD FYPPDIDVEW

QSNGQQEPER KHRMTPPQLD EDGSYFLYSK LSVDKSRWQQ

GDPFTCAVMH ETLQNHYTDL SLSHSPGK
```

The amino acid sequence of the CH3 domain of canine IgG.B is provided below:

```
                                           (SEQ ID NO: 6)
QP SVYVLPPSRE ELSKNTVSLT CLIKDFFPPD

IDVEWQSNGQ QEPESKYRTT PPQLDEDGSY

FLYSKLSVDK SRWQRGDTFI CAVMHEALHN

HYTQESLSHS PGK
```

The amino acid sequence of the CH3 domain of canine IgG.C is provided below:

```
                                           (SEQ ID NO: 7)
Q PNVYVLPPSR DEMSKNTVTL TCLVKDFFPP

EIDVEWQSNG QQEPESKYRM TPPQLDEDGS

YFLYSKLSVD KSRWQRGDTF ICAVMHEALH

NHYTQISLSH SPGK
```

The amino acid sequence of the CH3 domain of canine IgG.D is provided below:

```
                                           (SEQ ID NO: 8)
QPSVYV LPPSPKELSS SDTVTLTCLI KDFFPPEIDV

EWQSNGQPEP ESKYHTTAPQ LDEDGSYFLY

SKLSVDKSRW QQGDTFTCAV MHEALQNHYT DLSLSHSPGK
```

Fc Region of a Canine Fc Region

The Fc region of a canine IgG antibody comprises or consists of amino acids 231 to 447 (according to EU numbering) of the canine IgG antibody.

The amino acid sequence of the Fc domain of canine IgG.A is provided below:

```
                                              (SEQ ID NO: 9)
VPEPLGGPSVLI FPPKPKDILR ITRTPEVTCV VLDLGREDPE

VQISWFVDGK EVHTAKTQSR EQQFNGTYRV VSVLPIEHQD

WLTGKEFKCR VNHIDLPSPI ERTISKARGR AHKPSVYVLP

PSPKELSSSD TVSITCLIKD FYPPDIDVEW QSNGQQEPER

KHRMTPPQLD EDGSYFLYSK LSVDKSRWQQ GDPFTCAVMH

ETLQNHYTDL SLSHSPGK
```

The amino acid sequence of the Fc domain of canine IgG.B is provided below:

```
                                              (SEQ ID NO: 10)
APEMLGGPSVFIFPPK PKDTLLIART PEVTCVVVDL

DPEDPEVQIS WFVDGKQMQT AKTQPREEQF NGTYRVVSVL

PIGHQDWLKG KQFTCKVNNK ALPSPIERTI SKARGQAHQP

SVYVLPPSRE ELSKNTVSLT CLIKDFFPPD IDVEWQSNGQ

QEPESKYRTT PPQLDEDGSY FLYSKLSVDK SRWQRGDTFI

CAVMHEALHN HYTQESLSHS PGK
```

The amino acid sequence of the Fc domain of canine IgG.C is provided below:

```
                                              (SEQ ID NO: 11)
GCGLLGGPSVFIFPP KPKDILVTAR TPTVTCVVVD

LDPENPEVQI SWFVDSKQVQ TANTQPREEQ

SNGTYRVVSV LPIGHQDWLS GKQFKCKVNN KALPSPIEEI

ISKTPGQAHQ PNVYVLPPSR DEMSKNTVTL TCLVKDFFPP

EIDVEWQSNG QQEPESKYRM TPPQLDEDGS YFLYSKLSVD

KSRWQRGDTF ICAVMHEALH NHYTQISLSH SPGK
```

The amino acid sequence of the Fc domain of canine IgG.D is provided below:

```
                                              (SEQ ID NO: 12)
VPESLGGPSV FIFPPKPKDI LRITRTPEIT CVVLDLGRED

PEVQISWFVD GKEVHTAKTQ PREQQFNSTY RVVSVLPIEH

QDWLTGKEFK CRVNHIGLPS PIERTISKAR GQAHQPSVYV

LPPSPKELSS SDTVTLTCLI KDFFPPEIDV EWQSNGQPEP

ESKYHTTAPQ LDEDGSYFLY SKLSVDKSRW QQGDTFTCAV

MHEALQNHYT DLSLSHSPGK
```

Substitutions in Canine IgG Fc that Improve Half-Life

Increased serum persistence is a beneficial property for therapeutic polypeptides. This disclosure features substitutions in wild type canine IgG.A, IgG.B, IgG.C, and IgG.D Fc regions that enhance the half-life of a polypeptide or polypeptides comprising these Fc regions in a dog relative to a control polypeptide or control polypeptides, wherein the control polypeptide or control polypeptides are identical to the polypeptide or polypeptides except for having the corresponding wild type canine IgG Fc region in place of the IgG Fc region variant. The substitutions to increase half-life may be made in a canine CH2 region, a canine CH3 region, or in the context of a canine Fc (i.e., a CH2+CH3) region.

In some instances, this disclosure provides a canine IgG CH2 region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:1 to 4. Also provided are canine IgG CH2 region variants comprising an amino acid sequence that varies from any one of SEQ ID NOs.:1 to 4 by 1 to 15 amino acids.

In other instances, this disclosure features a canine IgG CH3 region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:5 to 8. Also featured are canine IgG CH3 region variants comprising an amino acid sequence that varies from any one of SEQ ID NOs.:5 to 8 by 1 to 15 amino acids.

In certain instances, this disclosure features a canine IgG Fc region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:9 to 12. Also disclosed are canine IgG Fc region variants comprising an amino acid sequence that varies from any one of SEQ ID NOs.:9 to 12 by 1 to 20 amino acids.

In some instances, at least one (e.g. 1, 2, or 3) of the following regions in the canine IgG Fc CH2 region variant are identical to the corresponding regions in a wild type canine IgG Fc CH2 region:
  amino acid positions 250-256;
  amino acid positions 285-288; and
  amino acid positions 307-315, wherein the amino acid positions are based on EU numbering. In some instances, all of the above regions in the canine IgG Fc CH2 region variant are identical to the corresponding regions in a wild type canine IgG Fc CH2 region.

In some instances, at least one (e.g. 1 or 2) of the following regions in the canine IgG Fc CH3 region variant are identical to the corresponding regions in a wild type canine IgG Fc CH3 region:
  Amino acid positions 376-380; and
  Amino acid positions 428-436, wherein the amino acid positions are based on EU numbering. In some instances, all of the above regions in the canine IgG Fc CH3 region variant are identical to the corresponding regions in a wild type canine IgG Fc CH3 region.

In some instances, at least one (e.g., 1, 2, 3, 4, or 5) of the following regions in the canine IgG Fc variant are identical to the corresponding regions in a wild type canine IgG Fc:
  amino acid positions 250-256;
  amino acid positions 285-288;
  amino acid positions 307-315;
  amino acid positions 376-380; and amino acid positions 428-436, wherein the amino acid positions are based on EU numbering. In some instances, all of the following regions in the canine IgG Fc variant are identical to the corresponding regions in a wild type canine IgG Fc.

In yet other embodiments, provided are a polypeptide or polypeptides comprising a canine IgG Fc CH2 region variant, the CH2 region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:1 to 4.

In some embodiments, featured are a polypeptide or polypeptides comprising a canine IgG Fc CH3 region variant, the CH3 region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:5 to 8.

In some embodiments, featured are a polypeptide or polypeptides comprising a canine IgG Fc region variant, the Fc region variant comprising an amino acid sequence that is at least 75%, at least 80%, at least 85%, at least 90%, at least 95%, at least 96%, at least 97%, at least 98%, at least 99%, or 100% identical to the amino acid sequence set forth in any one of SEQ ID NOs.:9 to 12.

In some instances, the above-described polypeptide or polypeptides comprise(s) a canine IgG CH2 region including one or more (e.g., 1, 2, 3, 4, 5, 6, 7, 8, 9, 10, 11, or 12) of:
- an amino acid other than the wild type amino acid occurring at amino acid position 250,
- an amino acid other than the wild type amino acid occurring at amino acid position 251,
- an amino acid other than the wild type amino acid occurring at amino acid position 252,
- an amino acid other than the wild type amino acid occurring at amino acid position 254,
- an amino acid other than the wild type amino acid occurring at amino acid position 256,
- an amino acid other than the wild type amino acid occurring at amino acid position 285,
- an amino acid other than the wild type amino acid occurring at amino acid position 286,
- an amino acid other than the wild type amino acid occurring at amino acid position 307,
- an amino acid other than the wild type amino acid occurring at amino acid position 308,
- an amino acid other than the wild type amino acid occurring at amino acid position 309,
- an amino acid other than the wild type amino acid occurring at amino acid position 311,
- an amino acid other than the wild type amino acid occurring at amino acid position 315, wherein the amino acid positions are based on EU numbering of the canine IgG.A, IgG.B, IgG.C, and IgG.D antibodies.

In some embodiments, the above-described polypeptide or polypeptides comprise(s) a canine IgG CH3 region including one or more (e.g., 1, 2, 3, 4, 5, 6, 7, or 8) of:
- an amino acid other than the wild type amino acid occurring at amino acid position 378,
- an amino acid other than the wild type amino acid occurring at amino acid position 380,
- an amino acid other than the wild type amino acid occurring at amino acid position 428,
- an amino acid other than the wild type amino acid occurring at amino acid position 430,
- an amino acid other than the wild type amino acid occurring at amino acid position 433,
- an amino acid other than the wild type amino acid occurring at amino acid position 434,
- an amino acid other than the wild type amino acid occurring at amino acid position 435, or
- an amino acid other than the wild type amino acid occurring at amino acid position 436, wherein the amino acid positions are based on EU numbering of the canine IgG.A, IgG.B, IgG.C, and IgG.D antibodies.

In certain embodiments, the above-described polypeptide or polypeptides comprise a canine IgG Fc region including one or more (e.g., 1, 2, 3, 4, 5, 6, 7, 8, 9, 10, 11, 12, 13, 14, 15, 16, 17, 18, 19, or 20) of:
- an amino acid other than the wild type amino acid occurring at amino acid position 250,
- an amino acid other than the wild type amino acid occurring at amino acid position 251,
- an amino acid other than the wild type amino acid occurring at amino acid position 252,
- an amino acid other than the wild type amino acid occurring at amino acid position 254,
- an amino acid other than the wild type amino acid occurring at amino acid position 256,
- an amino acid other than the wild type amino acid occurring at amino acid position 285,
- an amino acid other than the wild type amino acid occurring at amino acid position 286,
- an amino acid other than the wild type amino acid occurring at amino acid position 307,
- an amino acid other than the wild type amino acid occurring at amino acid position 308,
- an amino acid other than the wild type amino acid occurring at amino acid position 309,
- an amino acid other than the wild type amino acid occurring at amino acid position 311,
- an amino acid other than the wild type amino acid occurring at amino acid position 315,
- an amino acid other than the wild type amino acid occurring at amino acid position 378,
- an amino acid other than the wild type amino acid occurring at amino acid position 380,
- an amino acid other than the wild type amino acid occurring at amino acid position 428,
- an amino acid other than the wild type amino acid occurring at amino acid position 430,
- an amino acid other than the wild type amino acid occurring at amino acid position 433,
- an amino acid other than the wild type amino acid occurring at amino acid position 434,
- an amino acid other than the wild type amino acid occurring at amino acid position 435,
- an amino acid other than the wild type amino acid occurring at amino acid position 436, wherein the amino acid positions are based on EU numbering of the canine IgG.A, IgG.B, IgG.C, and IgG.D antibodies.

The substitutions that are encompassed by the present disclosure include one or more (e.g., 1, 2, 3, 4, 5, 6, 7, 8, 9, 10, 11, 12, 13, 14, 15, 16, 17, 18, 19, or 20) of those disclosed in Table 1.

TABLE 1

| Position (EU Numbering) | hIgG1 | Canine IgG.A | Canine IgG.B | Canine IgG.C | Canine IgG.D | Substitution |
|---|---|---|---|---|---|---|
| CH2 Region | | | | | | |
| 250 | T | I | T | I | I | E or Q |
| 251 | L | L | L | L | L | D or E |
| 252 | M | R | L | V | R | Y |
| 254 | S | T | A | A | T | T |

TABLE 1-continued

| Position (EU Numbering) | hIgG1 | Canine IgG.A | Canine IgG.B | Canine IgG.C | Canine IgG.D | Substitution |
|---|---|---|---|---|---|---|
| 256 | T | T | T | T | T | D, E, or F |
| 285 | H | H | Q | Q | H | N or D |
| 286 | N | T | T | T | T | D |
| 307 | T | P | P | P | P | R, Q, or A |
| 308 | V | I | I | I | I | P |
| 309 | L | E | G | G | E | P |
| 311 | Q | Q | Q | Q | Q | V |
| 315 | N | T | K | S | T | D |
| CH3 Region | | | | | | |
| 378 | A | D | D | D | D | V |
| 380 | E | E | E | E | E | A |
| 428 | M | M | M | M | M | L |
| 430 | E | E | E | E | E | A or K |
| 433 | H | Q | H | H | Q | K |
| 434 | N | N | N | N | N | S, A, or F |
| 435 | H | H | H | H | H | Y |
| 436 | Y | Y | Y | Y | Y | H |

In some instances, the substitutions that are encompassed by the present disclosure include one or more (e.g., 1, 2, 3, or 4) of those disclosed in Table 2.

TABLE 2

| Position (EU Numbering) | hIgG1 | Canine IgG.A | Canine IgG.B | Canine IgG.C | Canine IgG.D | Substitution |
|---|---|---|---|---|---|---|
| CH2 Region | | | | | | |
| 252 | M | R | L | V | R | Y or M |
| 254 | S | T | A | A | T | T |
| 256 | T | T | T | T | T | E |
| CH3 Region | | | | | | |
| 434 | N | N | N | N | N | Y, W, R, or H |

All possible combinations and permutations of the substitutions disclosed above are encompassed by this disclosure. In some instances, the substitutions include one or more of the following substitutions:

(i) Tyr at amino acid position 252, Thr at amino acid position 254, and Glu at amino acid position 256;
(ii) Leu at amino acid position 428 and Ser at amino acid position 434;
(iii) Asp at amino acid position 256, Arg at amino acid position 307, and Val at amino acid position 311;
(iv) Asp at amino acid position 256, Asp at amino acid position 315, and Val at amino acid position 378;
(v) Asp at amino acid position 256, Asp at amino acid position 286, Arg at amino acid position 307, and Val at amino acid position 311;
(vi) Asn at amino acid position 285, Gln at amino acid position 307, and Asp at amino acid position 315;
(vii) Asp at amino acid position 256, Arg at amino acid position 307, Val at amino acid position 311, and Val at amino acid position 378;
(viii) Asp at amino acid position 285, Val at amino acid position 311, and Val at amino acid position 378;
(ix) Asp at amino acid position 256, Asp at amino acid position 285, and Val at amino acid position 378;
(x) Asp at amino acid position 256, Val at amino acid position 311, and Val at amino acid position 378;
(xi) Asp at amino acid position 256, Asp at amino acid position 285, Asp at amino acid position 286, Arg at amino acid position 307, and Val at amino acid position 378;
(xii) Asp at amino acid position 256, Asp at amino acid position 286, Arg at amino acid position 307, Val at amino acid position 311, and Val at position 378;
(xiii) Gln at amino acid position 307, Val at amino acid position 311, and Val at amino acid position 378;
(xiv) Asp at amino acid position 285, Gln at amino acid position 307, and Val at amino acid position 378;
(xv) Asp at amino acid position 256, Asp at amino acid position 285, Arg at amino acid position 307, Val at amino acid position 311, and Val at amino acid position 378;
(xvi) Gln at amino acid position 307, Ala at amino acid position 380, Ser or Ala at amino acid position 434;
(xvii) Leu at amino acid position 428, and Ser or Ala at amino acid position 434;
(xviii) Gln at amino acid position 250 and Leu at amino acid position 428;
(xix) Glu at amino acid position 250 and Glu at amino acid position 251;
(xx) Phe at amino acid position 256 and Phe at amino acid position 309;
(xxi) Ala at amino acid position 430 and Lys at amino acid position 433;
(xxii) Phe at amino acid position 434 and His at amino acid position 436;
(xxiii) Tyr at amino acid position 435 and His at amino acid position 436;

In some instances, the substitutions do not include the combination of Tyr at amino acid position 252, Thr at amino acid position 254, and Glu at amino acid position 256.

The substitutions may be made on one or both chains of a CH2 domain, a CH3 domain, or an Fc domain. In some instances, the substitutions on both chains of a CH2 domain, a CH3 domain, or an Fc domain are identical. In some instances, the substitutions on both chains of a CH2 domain, a CH3 domain, or an Fc domain are not identical. In some instances, the Fc region includes one or more additional substitutions that increase or decrease effector function, improve product heterogeneity.

Other Substitutions that can be Combined with the Half-Life Enhancing Substitutions The development of a therapeutic polypeptide/protein (e.g., a monoclonal antibody) is a complex process that entails coordination of a complex set of activities to generate the desired polypeptide/protein. These include optimization of the specificity, affinity, functional activity, expression level in engineered cell lines, long-term stability, elimination or enhancement of effector functions and development of commercially viable manufacturing and purification methods. This disclosure encompasses any additional substitution that facilitates any one or more of the above goals.

In some embodiments, the substitutions are introduced to reduce effector function of the canine Fc region. Such substitutions may be at one or more (e.g., 1, 2, 3, 4, 5, 6, or 7) of the following positions of the canine IgG (numbering according to EU numbering): 238, 265, 297, 298, 299, 327, and 329. The substitution(s) can be to any of the other 19 amino acids. In some instances, the substitution is conservative. In certain non-limiting instances, the substituted amino acid at position 238 is Ala; the substituted amino acid at position 265 is Ala; the substituted amino acid at position 297 is Ala or Gln; the substituted amino acid at position 298 is Pro; the substituted amino acid at position 299 is Ala; the substituted amino acid at position 327 is Gly; and the substituted amino acid at position 329 is Ala. In some instances, the variant Fc region is from a canine IgG.B or IgG.C antibody.

In some embodiments, substitutions are introduced to a wild type canine IgG Fc region to enhance binding to Protein A so as to facilitate purification by protein A chromatography. Such substitutions may be at one or both (e.g., 1, 2, 3, 4, 5, 6, or 7) of the following positions of the canine IgG (numbering according to EU numbering): 252 and 254. The substitution(s) can be to any of the other 19 amino acids. In some instances, the substitution is conservative. In certain non-limiting instances, the substituted amino acid at position 252 is Met; and the substituted amino acid at position 254 is Ser.

In some embodiments, the substitutions are made to alter binding affinity to FcRn as compared to a parent polypeptide or a wildtype polypeptide (e.g., to increase or reduce binding affinity with FcRn). In some variations, the modification can be one, two, three, or four modifications that are selected from the group consisting of: 308F, 428L, 434M and 434S, where the numbering is according to the EU numbering. In some embodiments, the Fc variant includes one or more modifications selected from the group consisting of: 252Y/ 428L, 428L/434H, 428L/434F, 428L/434Y, 428L/434A, 428L/434M, and 428L/434S, where the numbering is according to the EU numbering. In some embodiments, the Fc variant includes one or more modification selected from the group consisting of: 428L/434S, 308F/428L/434S, where the numbering is according to the EU numbering. In some embodiments, the Fc variant includes one or more modifications selected from the group consisting of: 259I/ 434S, 308F/434S, 308F/428L/434S, 259I/308F/434S, 307Q/308F/434S, 250I/308F/434S, and 308F/319L/434S, where the numbering is according to the EU numbering. A detailed description of these modifications is described in e.g., U.S. Pat. No. 8,883,973B2, which is incorporated herein by reference in its entirety.

In some embodiments, the polypeptide comprises a hinge region of a canine antibody. In some embodiments, modifications can be made to the hinge region of the canine antibody to increase half-life. In some embodiments, the modification is 228P according to EU numbering.

In some embodiments, the binding with FcRn is pH-dependent. H310 and H435 (EU numbering) can be critical for pH-dependent binding. Thus, in some embodiments, the amino acids at position 310 (EU numbering) is histidine. In some embodiments, the amino acids at position 435 (EU numbering) is histidine. In some embodiments, the amino acids at both positions are histidine.

In some embodiments, the Fc region has LALA mutations (L234A and L235A mutations in EU numbering), or LALA-PG mutations (L234A, L235A, P329G mutations in EU numbering). In some embodiments, the amino acid residue at position 234 (EU numbering) is Ala. In some embodiments, the amino acid residue at position 234 (EU numbering) is Ala. In some embodiments, the amino acid residues at positions 234 and 235 (EU numbering) are Ala.

Polypeptides Comprising the Canine IgG Fc Variants

The disclosure encompasses any polypeptide that may benefit from having an increased half-life in a dog. To increase half-life these polypeptides are designed to include an Fc region variant (e.g., a CH2 region, a CH3 region, a CH2+CH3 region) disclosed above.

Exemplary polypeptides include, but are not limited to, whole antibodies, scFvs, nanobodies, ligand-binding portions of a receptor, cytokines, growth factors, enzymes, and peptides. For example a CH3 domain variant disclosed above may be attached to an scFv nanobody, ligand-binding portion of a receptor (e.g., the ligand-binding portion of canine IL-13Rα1 or IL-13Rα2), a cytokine, a growth factor, an enzyme, or a peptide. Alternatively, an Fc region variant disclosed above may be attached to these polypeptides. In another embodiment, a canine or caninized antibody is modified to include an Fc region variant disclosed herein.

In certain embodiments, the polypeptides of this disclosure include an antibody hinge region. The hinge region may be placed between the antigen or ligand-binding domain of the polypeptide and the Fc region variant. In some instances, the hinge region is attached to the C-terminus of a cytokine, a growth factor, an enzyme, or a peptide and the hinge region is attached to the N-terminus of the Fc region variant. Exemplary hinge region sequences are provided below.

```
IgG.A:
                                    (SEQ ID NO: 17)
FNECRCTDTPPCPVPEP;

IgG.B:
                                    (SEQ ID NO: 18)
PKRENGRVPRPPDCPKCPAPEM;

IgG.C:
                                    (SEQ ID NO: 19)
AKECECKCNCNNCPCPGCGL;

IgG.D:
                                    (SEQ ID NO: 20)
PKESTCKCISPCPVPES;
and IgG.Dmut:
                                    (SEQ ID NO: 21)
PKESTCKCIPPCPVPES.
```

The hinge region, if used, in a recombinant protein of this disclosure may include zero to six (i.e., 0, 1, 2, 3, 4, 5, or 6) amino acid substitutions relative to an amino acid sequence set forth in any one of SEQ ID NOs.:17-21. In some instances, the hinge region used in a recombinant protein of this disclosure is at least 80%, at least 85%, at least 90%, at least 95%, at least 96%, at least 97%, at least 98%, at least 99%, or 100% identical to an amino acid sequence set forth in any one of SEQ ID NOs.:17-21.

In certain embodiments, a linker sequence may be used instead of an antibody hinge sequence to connect the polypeptide (e.g., antibodies, ligand-binding domains of receptors, enzymes, ligands, peptides) to the canine Fc region variants disclosed herein. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Examples of peptide linkers include: Gly, Ser; Gly Ser; Gly Gly Ser; Ser Gly Gly; Gly Gly Gly Ser (SEQ ID NO:22); Ser Gly Gly Gly (SEQ ID NO:23); Gly Gly Gly Gly Ser (SEQ ID NO:24); Ser Gly Gly Gly Gly (SEQ ID NO:25); Gly Gly Gly Gly Gly Ser (SEQ ID NO:26); Ser Gly Gly Gly Gly Gly (SEQ ID NO:27); Gly Gly Gly Gly Gly Gly Ser (SEQ ID NO:28); Ser Gly Gly Gly Gly Gly Gly (SEQ ID NO:29); (Gly Gly Gly Gly Ser)$_n$ (SEQ ID NO:24)$_n$, wherein n is an integer of one or more (e.g., 1, 2, 3, 4, 5); and (Ser Gly Gly Gly Gly)$_n$ (SEQ ID NO:25)$_n$, wherein n is an integer of one or more (e.g., 1, 2, 3, 4, 5).

Non-peptide linkers may also be used to link the polypeptide or polypeptides of interest to an Fc region variant disclosed herein. For example, alkyl linkers such as —NH (CH$_2$)$_n$C(O)—, wherein n=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc.

The polypeptide or polypeptides of this disclosure may comprise a binding domain. The binding domain can specifically bind to a protein, subunit, domain, motif, and/or epitope of a selected target described herein. In some embodiments, the polypeptide or polypeptides (e.g., fusion polypeptide) can comprise a protein, wherein the protein is a therapeutic protein described herein. In some embodiments, the target (e.g., for the target of the binding domain) or the therapeutic protein (e.g., for the fusion polypeptide) is selected from the group consisting of: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin MA, Activin MA ALK-2, Activin RIB ALK-4, Activin RITA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, IgE, Angiotensin type 1 (AT1) receptor, Angiotensin type 2 (AT2) receptor, ARC, ART, Artemin, anti-Id, ASPARTIC, Atrial natriuretic factor, av/b3 integrin, Ax1, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD47, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Clostridium botulinum toxin, Clostridium perfringens toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, GLP1, GLP2, Glucagon, Glut 4, glycoprotein IIb/IIIa (GP IIb/IIIa), GM-CSF, gp130, gp72, GRO, GnRH, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, cardiac myosin, cytomegalovirus (CMV), growth hormone (GH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NAV 1.7, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PD1, PDL1, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACT), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p'75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DCTRAIL R2 TNFRH2), TNFRST23 (DCTRAIL R1TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/ VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk (e.g., TrkA), TROP-2, TSG, TSLP, tumor-associated antigen CA 125, tumor-associated antigen expressing Lewis Y related carbohydrate, TWEAK, TXB2, Ung, UPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factor.

In some embodiments, the binding domain specifically binds to one or more therapeutic targets or antigens in canine, such as, but are not limited to, ACE, ACE-2, Activin, Activin A, Activin AB, Activin B, Activin C, Activin MA, Activin MA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (fit-1), VEGF, VEGFR, and VEGFR-3 (flt-4).

In some embodiments, the polypeptide or polypeptides can comprise a protein, wherein the protein is a therapeutic protein, e.g., EPO, CTLA4, LFA3, VEGFR1/VEGFR3, IL-1R, IL-4R, GLP-1 receptor agonist, or Thrombopoietin binding peptide. In some embodiments, the therapeutic protein is ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, ANG, Ang, Angiotensin type 1 (AT1) receptor, Angiotensin type 2 (AT2) receptor, Atrial natriuretic factor, av/b3 integrin, b-ECGF, CD19, CD20, CD30, CD34, CD40, CD40L, CD47, COX, CTLA-4, EGFR (ErbB-1), EPO, Follicle stimulating hormone, GDF-8 (Myostatin), GLP1, GLP2, GnRH, Growth hormone releasing factor, IgE, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-17, IL-18, IL-18R, IL-21, IL-22, IL-23, IL-25, IL-31, IL-33, interleukin receptor (e.g., IL-1R, IL-2R, IL-4R, IL-5R, IL-6R, IL-8R, IL-9R, IL-10R, IL-12R, IL-13R, IL-15R, IL-17R, IL-18R, IL-21R, IL-22R, IL-23R, . IL-25R, IL-31R, IL-33R), LAP (TGF-1), Latent TGF-1, Latent TGF-1 bp1, LFA-1, Neuronal growth factor (NGF), NGFR, NGF-beta, OX40L, OX40R, PD1, PDL1, TGF, TGF-alpha, TGF-beta, TGF-beta Pan Specific, TGF-beta R1 (ALK-5), TGF-beta R11, TGF-beta RIIb, TGF-beta Rill, TGF-beta1, TGF-beta2, TGF-beta3, TGF-beta4, TGF-beta5, TNF, TNF-alpha, TNF-alpha beta, TNF-beta2, TNFc, TNF-RI, TNF-RII, TNFRSF16 (NGFR p75NTR), TNFRSF9 (4-1BB CD137, ILA), VEFGR-1 (fit-1), VEGF, VEGFR, or VEGFR-3 (flt-4).

In some embodiments, the therapeutic protein is any protein described herein. In some embodiments, the polypeptide or polypeptides further comprises a canine IgG CH2 domain, IgG CH3 domain, or IgG Fc region as described herein. The modified canine IgG CH2 domain, IgG CH3 domain, or IgG Fc region can enhance the half-life the therapeutic proteins in vivo.

Pharmaceutical Compositions

To prepare pharmaceutical or sterile compositions of a polypeptide or polypeptides described herein, the polypeptide or polypeptides can be admixed with a pharmaceutically acceptable carrier or excipient. (See, e.g., Remington's Pharmaceutical Sciences and U.S. Pharmacopeia: National Formulary, Mack Publishing Company, Easton, Pa. (1984)).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.). In one embodiment, the polypeptide or polypeptides of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the polypeptide compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, a polypeptide or polypeptides exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the polypeptide or polypeptides can be administered by an invasive route such as by injection. In further embodiments, the polypeptide or polypeptides is administered intravenously, subcutaneously, intramuscularly, intraarterially, intratumorally, or by inhalation, aerosol delivery.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the polypeptide or polypeptides in a local rather than systemic manner, for example, via injection of the antibody directly into an arthritic joint or pathogen-induced lesion characterized by immunopathology, often in a depot or sustained release formulation. Furthermore, one may administer the polypeptide or polypeptides in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including, without limitation, the age, weight, and physical condition of the canine being treated, the serum or tissue turnover rate of the therapeutic antibody, the level of symptoms, the immunogenicity of the therapeutic polypeptide or polypeptides, and the accessibility of the target cells in the biological matrix. Preferably, the administration regimen delivers sufficient therapeutic polypeptide or polypeptides to effect improvement in the target disease state, while simultaneously minimizing undesired side effects. Accordingly, the amount of biologic delivered depends in part on the particular therapeutic polypeptide or polypeptides and the severity of the condition being treated. Guidance in selecting appropriate doses of therapeutic antibodies is available (see, e.g., Wawrzynczak Antibody Therapy, Bios Scientific Pub. Ltd, Oxfordshire, UK (1996); Milgrom et al. New Engl. J. Med. 341:1966-1973 (1999); Slamon et al. New Engl. J. Med. 344:783-792 (2001); Beniaminovitz et al. New Engl. J. Med. 342:613-619 (2000); Ghosh et al. New Engl. J. Med. 348:24-32 (2003); Lipsky et al. New Engl. J. Med. 343: 1594-1602 (2000)).

Determination of the appropriate dose of the polypeptide or polypeptides is made by one skilled in the art, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Nucleic Acids, Vectors, Host Cells, and Methods of Making

The disclosure also encompasses nucleic acid or nucleic acids encoding the polypeptide or polypeptides described herein, a vector or vectors comprising the nucleic acid or nucleic acids, and host cells comprising the nucleic acid or nucleic acids or the vector or vectors.

The polypeptide or polypeptides described herein may be produced in bacterial or eukaryotic cells. Some polypeptides, e.g., Fab's, can be produced in bacterial cells, e.g., *E. coli* cells. Polypeptides can also be produced in eukaryotic cells such as transformed cell lines (e.g., CHO, 293E, COS, 293T, Hela). In addition, polypeptides (e.g., scFv's) can be expressed in a yeast cell such as *Pichia* (see, e.g., Powers et al., J Immunol Methods. 251:123-35 (2001)), *Hanseula*, or *Saccharomyces*. To produce the antibody of interest, a polynucleotide or polynucleotides encoding the polypeptide or polypeptides is/are constructed, introduced into an expression vector or expression vectors, and then expressed in suitable host cells. To improve expression, the nucleotide sequences of the genes can be recoded without changing (or minimally changing—e.g., removal of a C-terminal residue of the heavy or light chain) the amino acid sequence. The areas for potential recoding include those associated with translation initiation, codon usage, and possible unintended mRNA splicing. Polynucleotides encoding an Fc region variant described herein would be readily envisioned by the ordinarily skilled artisan.

Standard molecular biology techniques can be used to prepare the recombinant expression vector(s), transfect the host cells, select for transformants, culture the host cells, and recover the polypeptide (e.g., antibody).

If the polypeptide or polypeptides is to be expressed in bacterial cells (e.g., E. coli), the expression vector should have characteristics that permit amplification of the vector in the bacterial cells. Additionally, when E. coli such as JM109, DH5α, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in E. coli. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of E. coli, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the polypeptide or polypeptides is to be expressed in animal cells such as CHO, COS, and NIH3T3 cells, the expression vector includes a promoter necessary for expression in these cells, for example, an SV40 promoter (Mulligan et al., Nature, 277:108 (1979)) (e.g., early simian virus 40 promoter), MMLV-LTR promoter, EF 1a promoter (Mizushima et al., Nucleic Acids Res., 18:5322 (1990)), or CMV promoter (e.g., human cytomegalovirus immediate early promoter). In addition to the nucleic acid sequence encoding the Fc region variant, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In some embodiments, the polypeptide or polypeptides are produced in mammalian cells. Exemplary mammalian host cells for expressing polypeptide or polypeptides include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of the antibody is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Methods of Treatment

The polypeptide or polypeptides disclosed herein can be used to treat or prevent any disease or disorder in a dog in need thereof. This invention is particularly helpful in the treatment of chronic conditions where repeated dosing is required. Because of the increased half-life of the protein therapeutic, less frequent dosing and/or reduced dose levels may be possible.

In some embodiments, the disease, disorder, condition or symptoms being treated or prevented is an allergic disease, a chronic pain, an acute pain, an inflammatory disease, an autoimmune disease, an endocrine disease, a gastrointestinal disease, a skeletal/musculoskeletal disease, a cardiovascular disease, a neurological disease, a renal disease, a metabolic disease, a immunological disease, a genetic/inherited disease, a fertility related disorder, an infectious disease or a cancer. In certain embodiments, the disease or disorder being treated or prevented is atopic dermatitis, allergic dermatitis, food allergy, osteoarthritic pain, perioperative pain, dental pain, cancer pain, arthritis, anemia, obesity, or diabetes.

Antibodies may not only be used to treat or prevent disease but also modulate normal biological function for example manage fertility or behavior.

Diagnosis

The polypeptide or polypeptides disclosed herein can also be used for various diagnostic purpose, for example, to determine whether a dog has any particular disease or disorder. In some embodiments, the polypeptide or polypeptides may comprise a binding domain. The binding domain can specifically bind to a protein, subunit, domain, motif, and/or epitope as described herein (e.g., a maker for cancer cells). In some embodiments the polypeptide or polypeptides further comprises a labeling group. In general, label groups fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

In some embodiments, the labeling group is a probe, a dye (e.g., a fluorescent dye), or a radioactive isotope (e.g., $^{3}$H, $^{14}$C, $^{22}$Na, $^{36}$Cl, $^{35}$S, $^{33}$P, or $^{125}$I).

Specific labels can also include optical dyes, including, but not limited to, chromophores, phosphors and fluorophores, with the latter being specific in many instances. Fluorophores can be either "small molecule" fluores, or proteinaceous fluores.

The fluorescent label can be any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, which is incorporated by reference in its entirety.

Suitable proteinaceous fluorescent labels also include, but are not limited to, green fluorescent protein, including a Renilla, Ptilosarcus, or Aequorea species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), f3 galactosidase (Nolan et al., 1988, Proc. Natl. Acad. Sci. U.S.A. 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references in this paragraph are expressly incorporated herein by reference in the entirety.

Assays $Fc_\gamma RI$ Binding:

Binding to $Fc_\gamma RI$ is a measure of the ability of an antibody to mediate ADCC. In order to assess this property for an antibody an assay to measure binding of the antibody to $Fc_\gamma RI$ can be conducted using methods known in the art.

C1q Binding:

Binding to the first component of complement, C1q, is a measure of the ability of an antibody to mediate complement-dependent cytotoxicity (CDC). In order to assess this property for an antibody, an assay to measure binding of the antibody to C1q can be conducted using methods known in the art.

Half-Life:

Methods of measuring half-life of an antibody is well known in the art. See, e.g., Booth et al., MAbs, 10(7):1098-1110 (2018). As an example, the half-life of an antibody can be measured by injection of the antibody into an animal model and measuring levels of the antibody in the serum over a certain period of time. Exemplary animal models include non-human primate models and transgenic mouse models. The transgenic mouse models (e.g. Tg32 or Tg276 transgenic mice) can be null for mouse FcRn alpha chain and express the human FcRn alpha transgene (e.g. under the control of a constitutive promoter). The human FcRn alpha chain can pair in vivo with the mouse β2-microglobulin protein forming a functional chimeric FcRn heterodimer.

EXAMPLES

Example 1: Alanine Scanning Mutagenesis of CH2 and CH3 Domains of Canine IgG.B

Alanine scanning mutagenesis (Morrison and Weiss, Curr. Opin. Chem. Biol. 5: 302-307 (2001)) was completed on residues 250, 251, 252, 254, 256, 285, 286, 307, 309, 311, 315 in the CH2 domain and residues 378, 380, 428, 430, 433, 434, 435, and 436 in the CH3 domain. For this experiment, the wild-type (wt) sequence of the CH2 and CH3 domains of canine IgG.B was synthesized and used as template for the mutagenesis. Each specified position with the exception of position 254 was individually changed to alanine by PCR mutagenesis using a primer encoding the change. Position 254 is alanine in the wild-type sequence, and it was modified to serine. The PCR product was subcloned into the GenScript FASEBA plasmid, transformed into *E. coli* and sequence verified for the presence of the variant. Upstream of the CH2 domain is the SASA (single-domain antibody against serum albumin) tag (See, e.g. US 2013/0129727A1) which has pM affinity for albumin. The PelB (pectate lyase B) signal peptide is at the N-terminus to facilitate secretion of the Fc into the medium. The expression of CH2-CH3 protein was regulated by the Lac promoter. The supernatants from conditioned medium were analyzed for binding to canine FcRn (UniProtKB-E2ROL6 [FcRn] and UniProtKB-E2RN10 [canine beta-2-microglobulin]) at pH 5.5 using surface plasmon resonance (SPR).

Figure 7U:
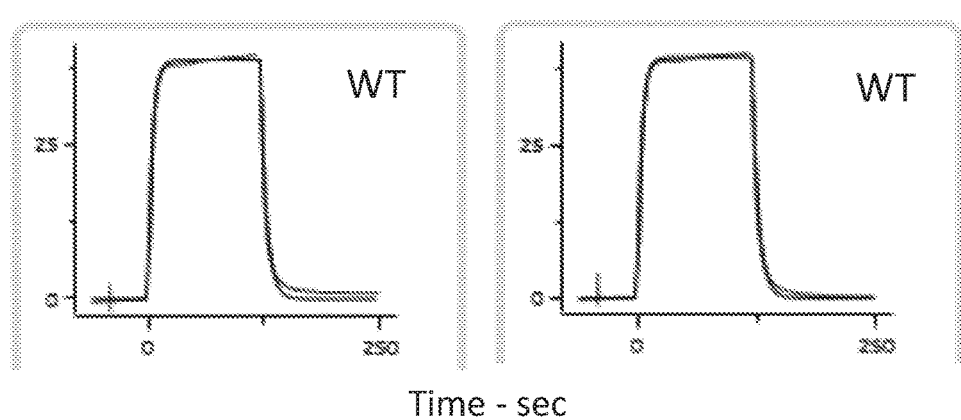
Figure 8A:
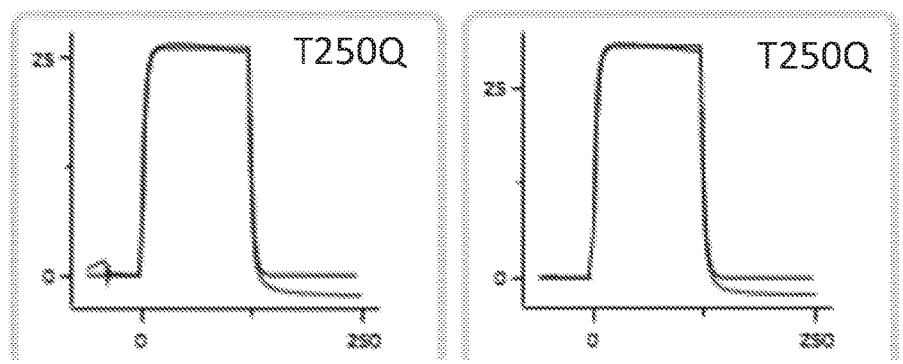
FIGS. 8A-8C depict Biacore sensorgrams for wild type and the different variants from the NNK libraries at position 250. The lighter line on each figure represents the measured data and the darker line is the fitted curve using a 1:1 interaction model.
Figure 8B:
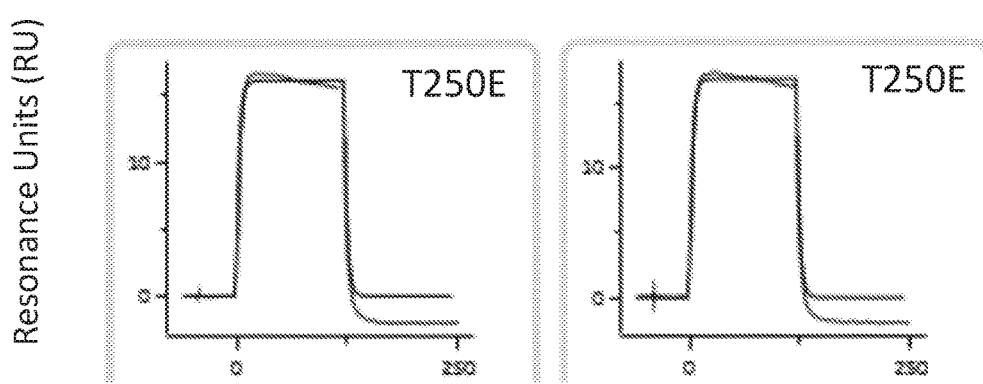
Figure 8C:
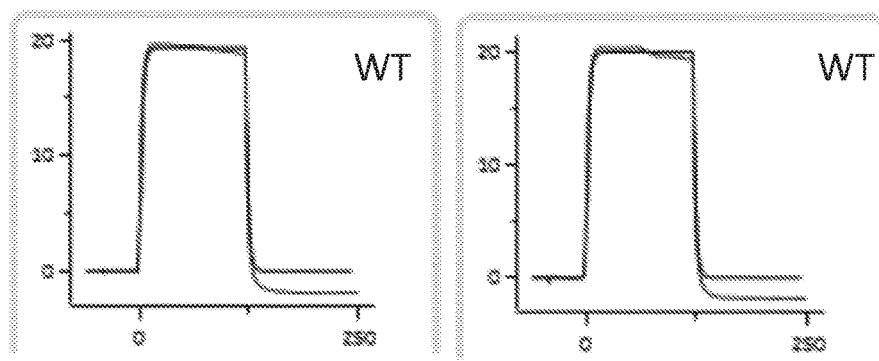
Figure 9A:
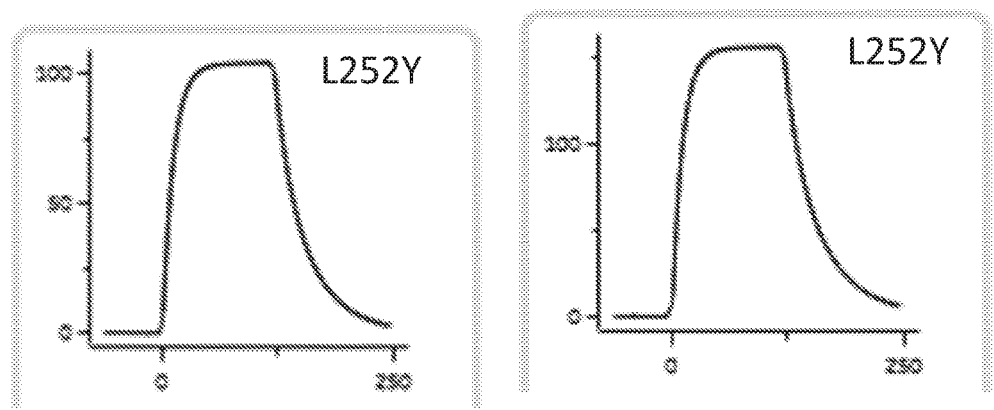
FIGS. 9A-9C depict Biacore sensorgrams for wild type and the different variants from the NNK libraries at position 252. The lighter line on each figure represents the measured data and the darker line is the fitted curve using a 1:1 interaction model.
Figure 9B:
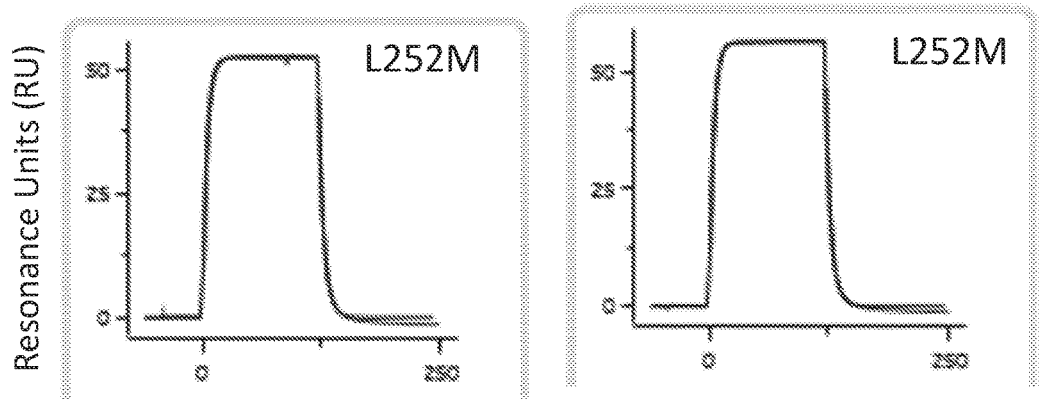
Figure 9C:
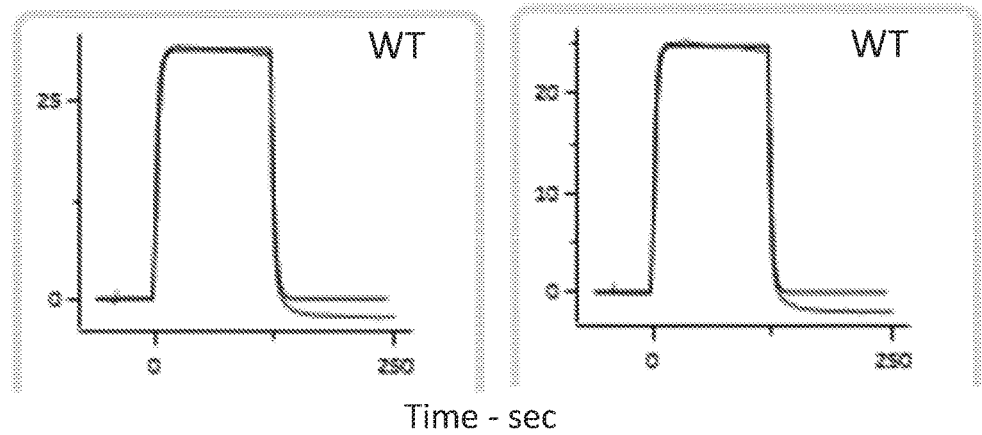
Figure 10A:
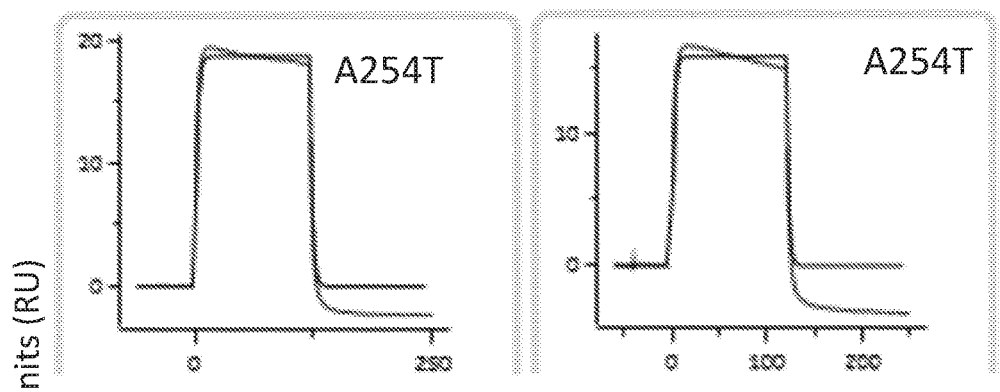
FIGS. 10A and 10B depict Biacore sensorgrams for wild type and the variant A254T. The lighter line represents the measured data and the darker line represents the fitted curve using a 1:1 interaction model.
Figure 10B:
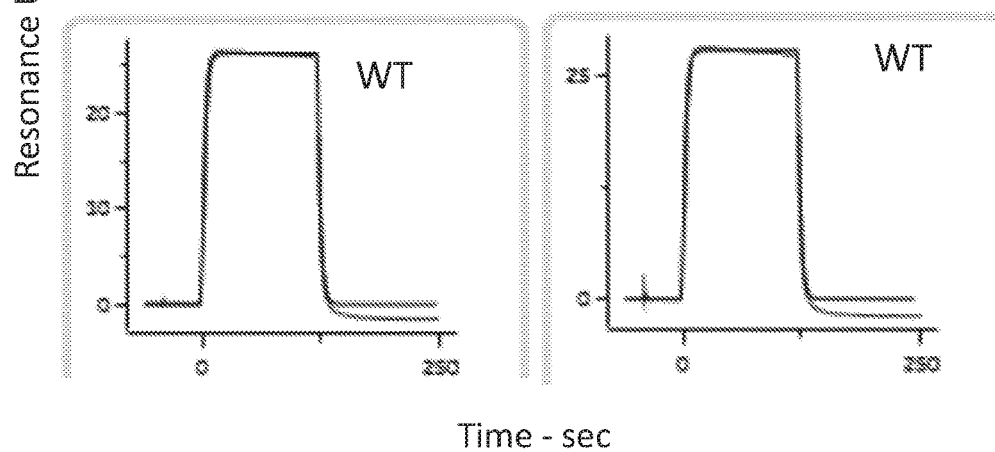
Figure 11A:
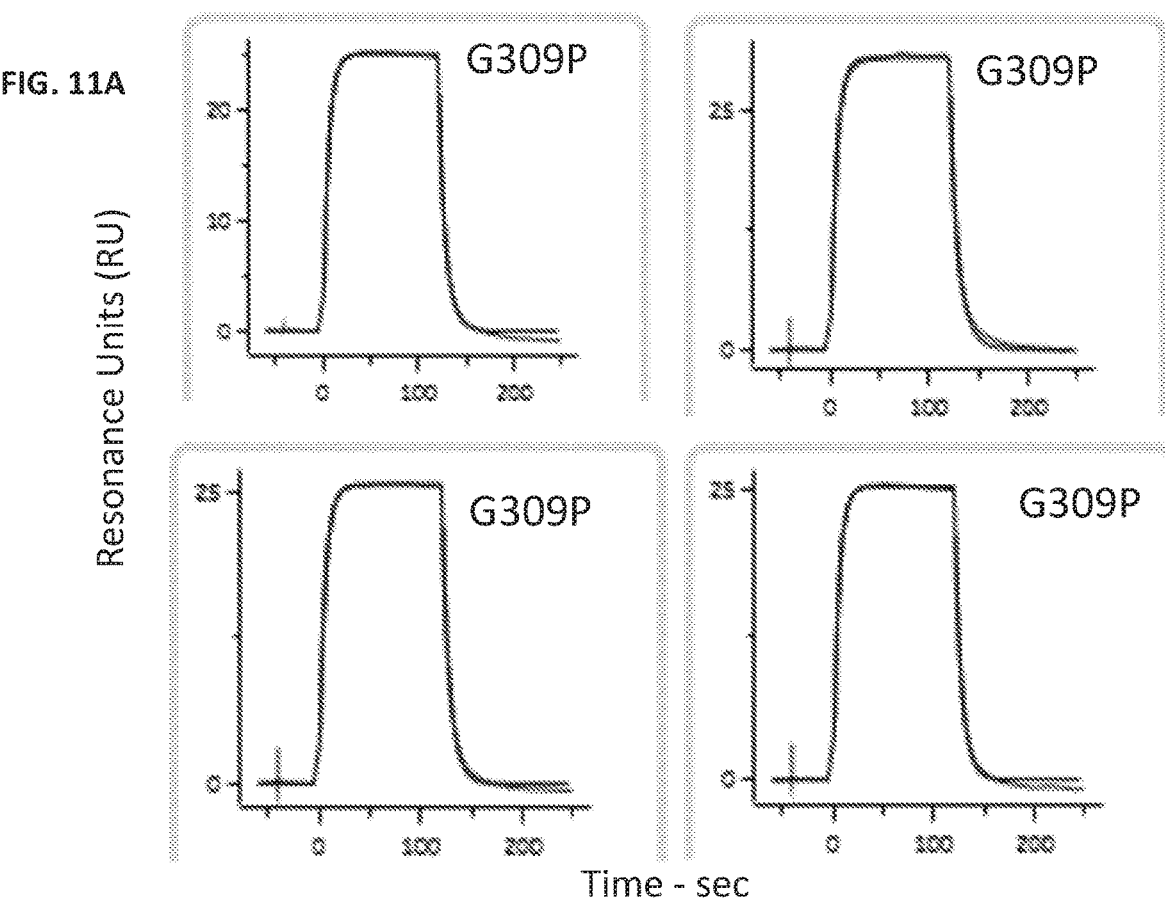
FIGS. 11A and 11B depict Biacore sensorgrams for wild type and the variant G309P. The lighter line represents the measured data and the darker line represents the fitted curve using a 1:1 interaction model.
Figure 11B:
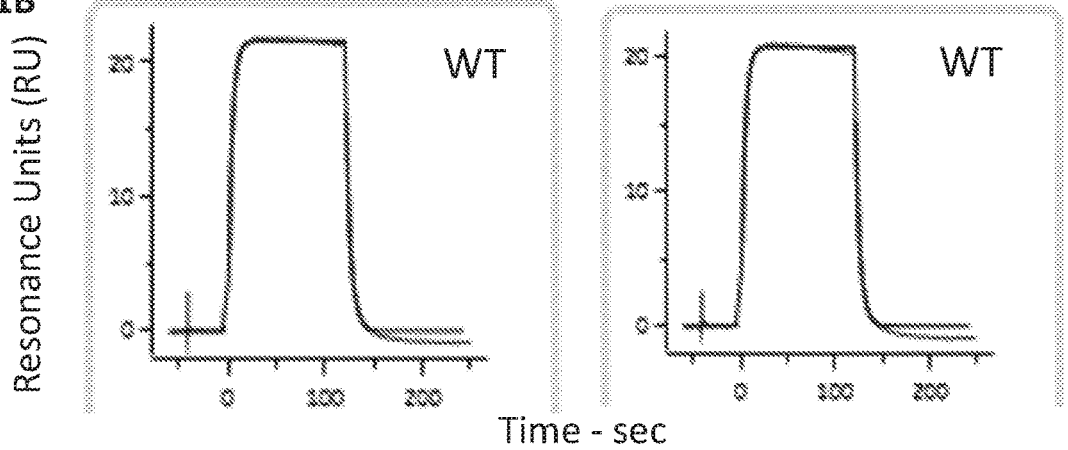
Figure 12A:
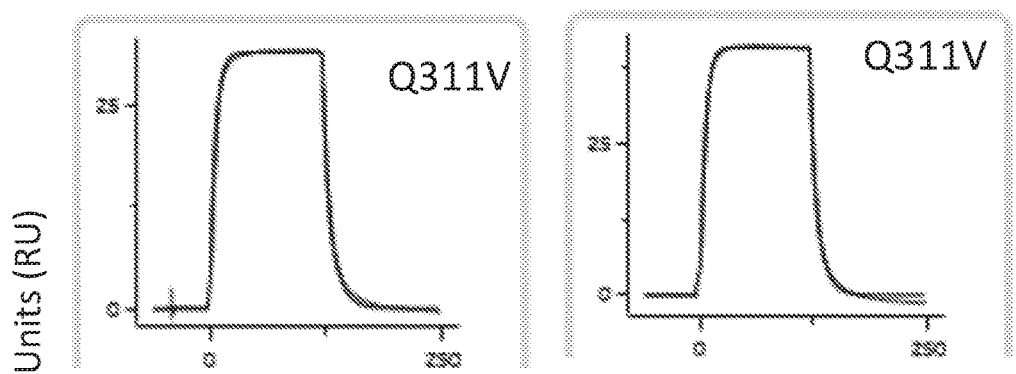
FIGS. 12A and 12B depict Biacore sensorgrams for wild type and the variant Q311V. The lighter line represents the measured data and the darker line represents the fitted curve using a 1:1 interaction model.
Figure 12B:
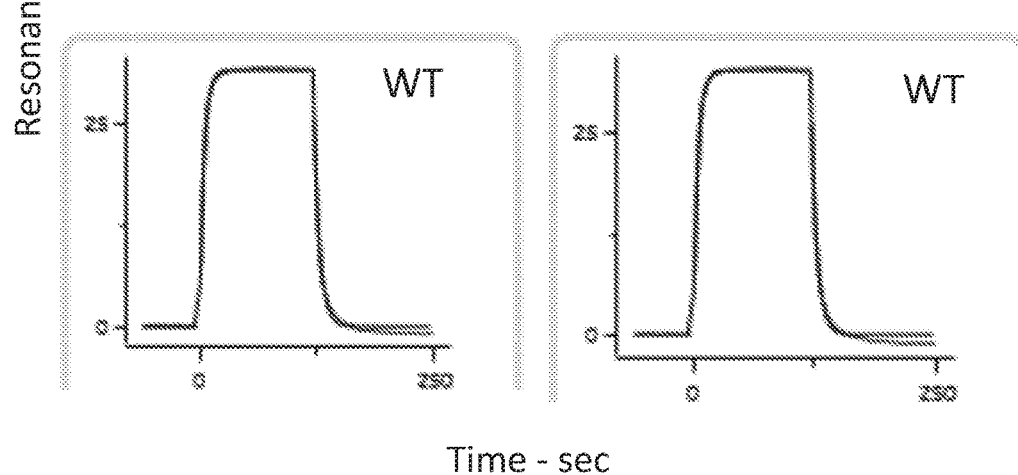
Figure 13A:
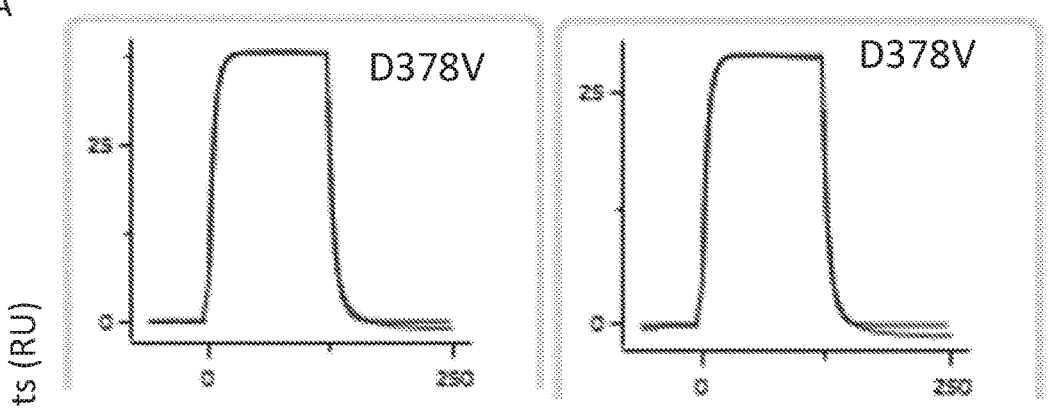
FIGS. 13A and 13B depict Biacore sensorgrams for wild type and the variant D378V. The lighter line represents the measured data and the darker line represents the fitted curve using a 1:1 interaction model.
Figure 13B:
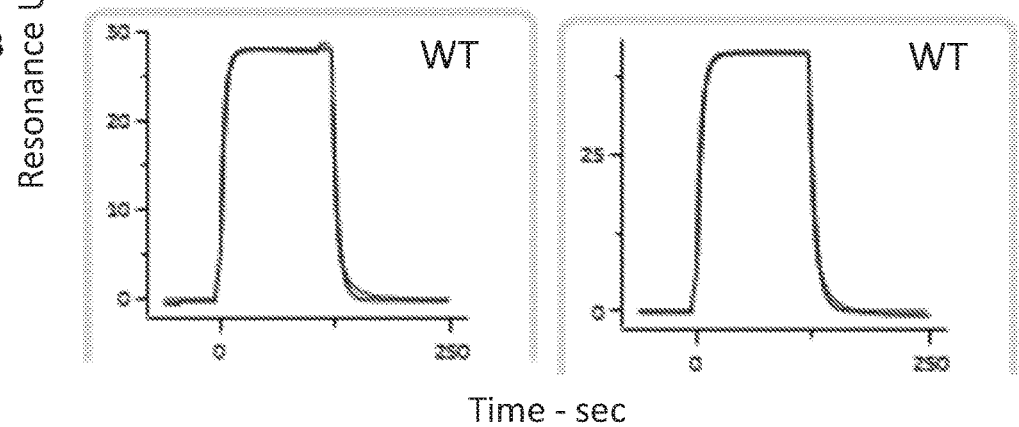
Figure 14A:
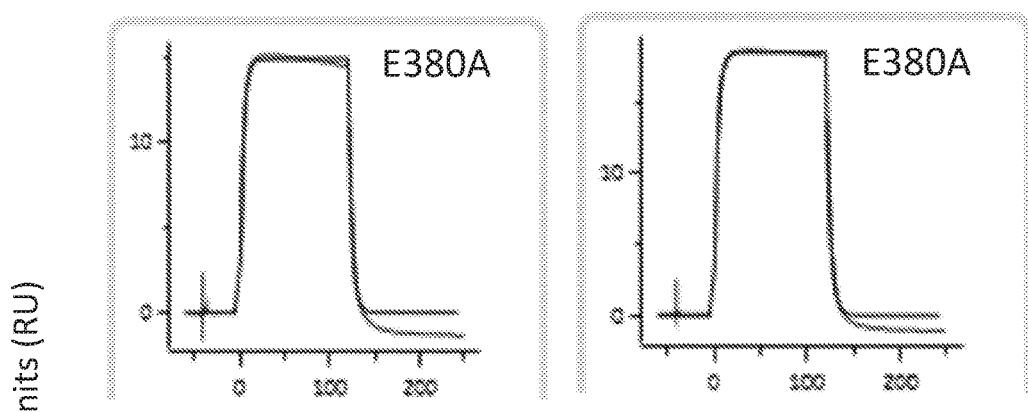
FIGS. 14A and 14B depict Biacore sensorgrams for wild type and the variant E380A. The lighter line represents the measured data and the darker line represents the fitted curve using a 1:1 interaction model.
Figure 14B:
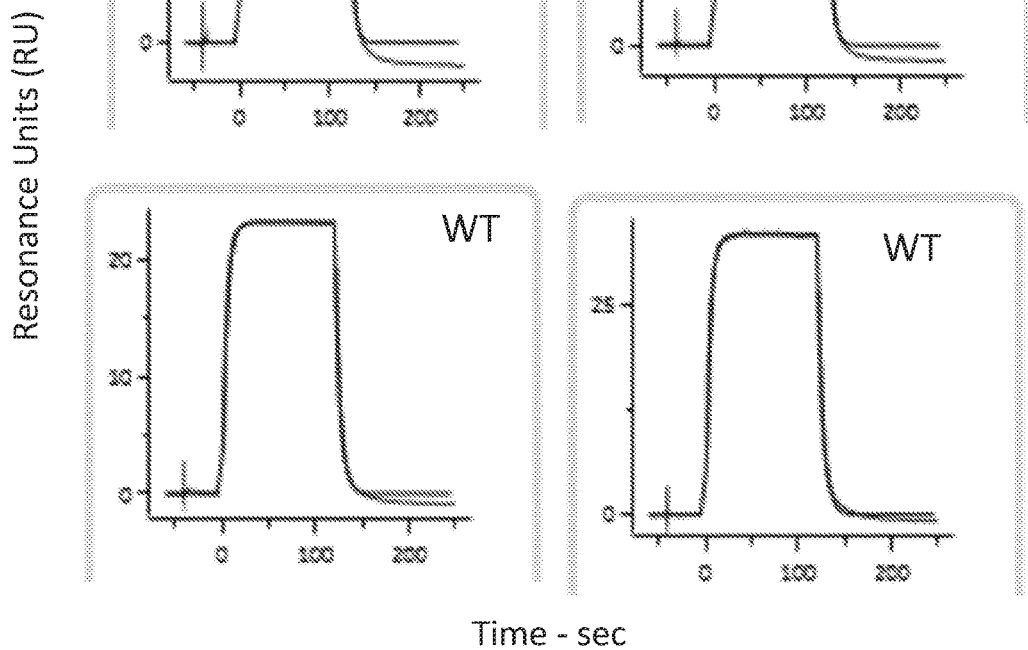
Figure 15A:
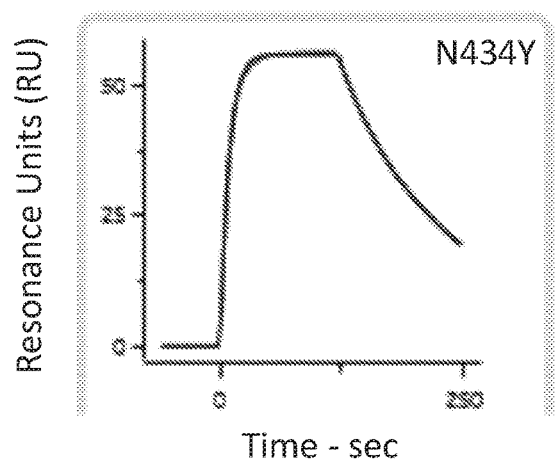
Figure 15B:
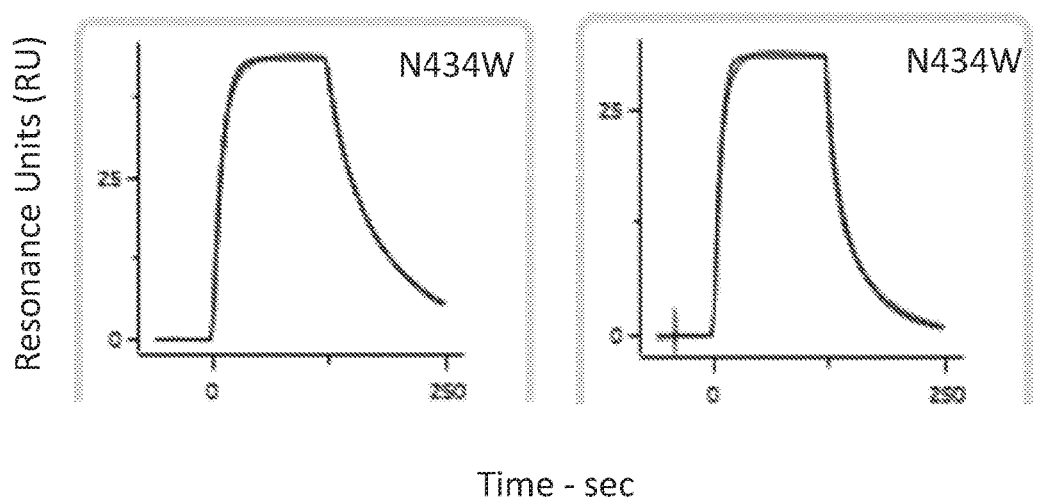
Figure 15C:
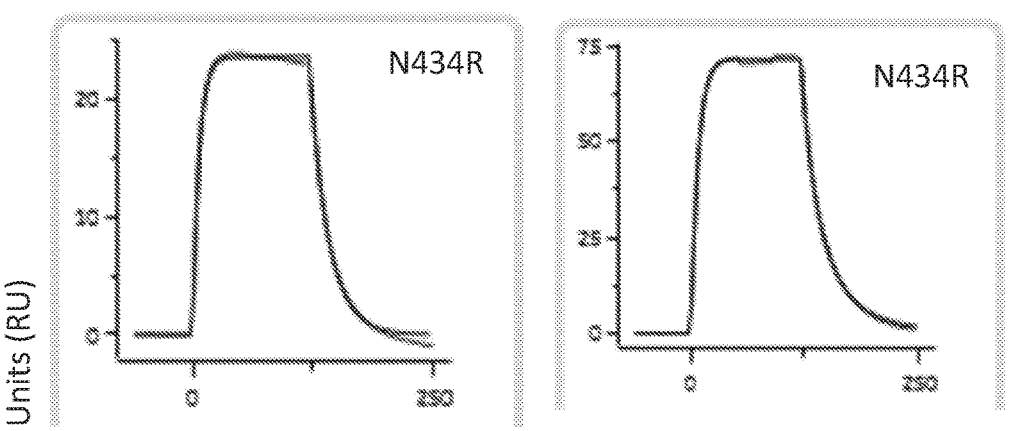
Figure 15D:
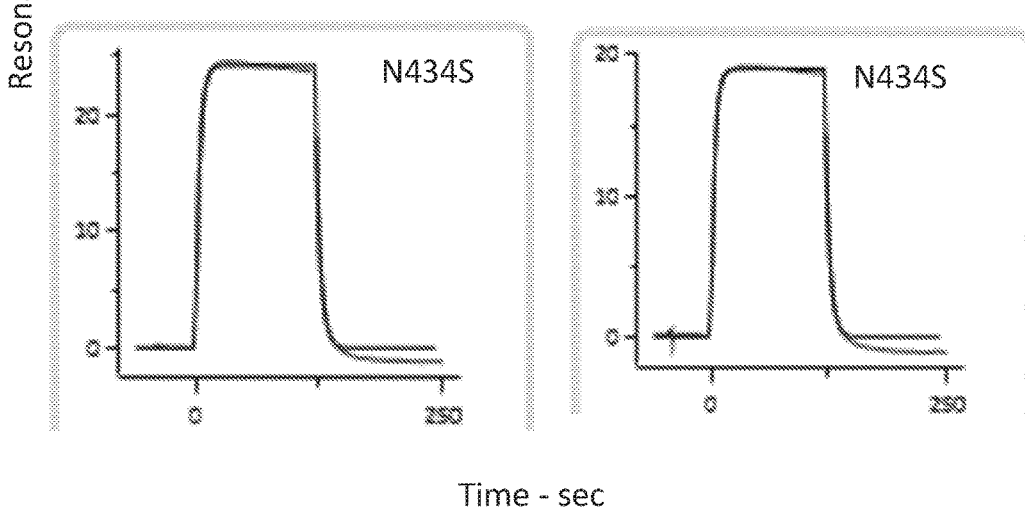
Figure 16A:
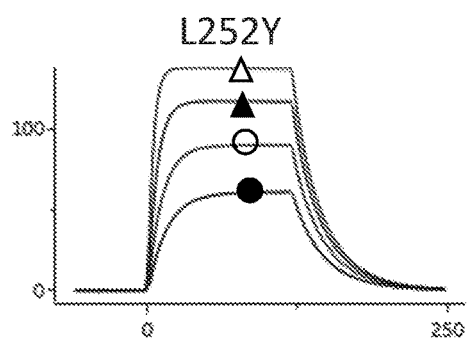
FIGS. 16A-16D depict Biacore sensorgrams for different variants in a concentration series. The concentration of canine FcRn used were 100 nM (white circle), 200 nM (black circle), 400 nM (black triangle), and 800 nM (white triangle). The lighter line on each figure is the measured data and the darker line is the fitted curve using a 1:1 interaction model.
Figure 16B:
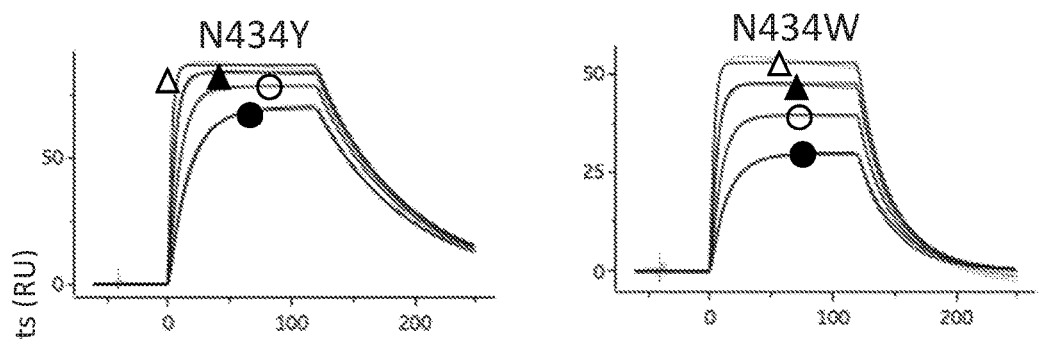
Figure 16C:
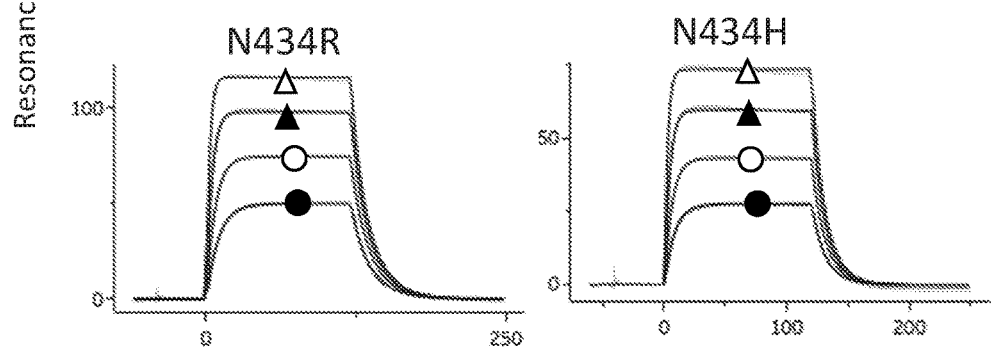
Figure 16D:
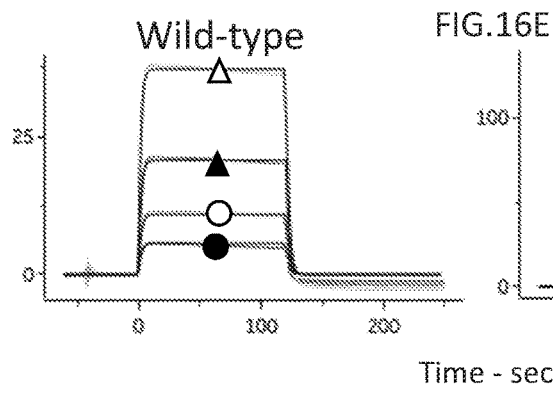
Figure 16E:
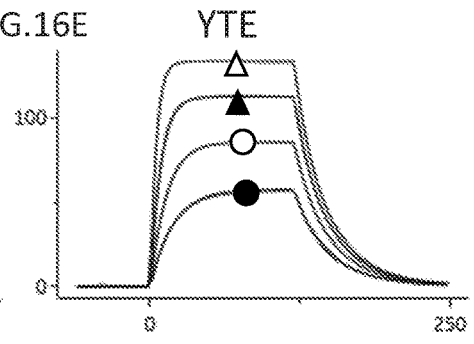

For the SPR analyses using Biacore 8K, bovine serum albumin (BSA) was immobilized to CMS sensor chip. The sensor chip surface of flow cells 1 and 2 were activated by freshly mixed 50 mmol/L N-Hydroxysuccinimide and 200 mmol/L 1-ethyl-3-(3-dimethylaminopropyl) carbodiimide hydrochloride for 420 s (10 μL/min). Afterwards, BSA diluted in 10 mM sodium acetate (pH 4.5) was injected into the flow cell 2 to achieve conjugation, while flow cell 1 was set as blank. After the amine coupling reaction, the remaining active coupling sites on chip surface were blocked with 420 s injection of 1 mM ethanolamine hydrochloride. The running buffer for the binding experiment was HBS-EP (10 mM HEPES, 500 mM NaCl, 3 mM EDTA, 0.05% Tween 20, pH 5.5) and it was run at 25° C. Supernatants from the alanine variants were injected over chip surface and captured via the SASA tag onto the immobilized BSA for 60 sec. Canine FcRn at 400 nM was injected for 120 sec and the dissociation was complete with running buffer for 120 sec. The flow rate for the immobilization phase of BSA was 10 μL/min and the flow rate for the association and dissociation phase was 30 μL/min. All of the data was processed using the Biacore 8K evaluation software version 1.1. The tabulated data is shown in Table 3 with the last column containing the average KD of wild-type divided by the variant KD. The sensorgrams are shown in FIGS. 7A-7U.

TABLE 3

| Variant | ka (1/Ms) | kd (1/s) | KD (M) | Comments | WT KD Avg/ Variant KD |
|---|---|---|---|---|---|
| T250A | 1.86E+07 | 6.24E+00 | 3.35E−07 | | 1.69 |
| T250A | 3.87E+06 | 1.27E+00 | 3.28E−07 | | 1.72 |
| L251A | | | | No Binding | |
| L251A | | | | No Binding | |
| L252A | 3.32E+05 | 9.69E−02 | 2.92E−07 | | 1.94 |
| L252A | 2.36E+06 | 5.67E−01 | 2.40E−07 | | 2.36 |
| A254S | 7.91E+06 | 2.69E+00 | 3.40E−07 | | 1.66 |
| A254S | 2.39E+06 | 7.58E−01 | 3.17E−07 | | 1.78 |
| T256A | 3.71E+05 | 1.66E−01 | 4.47E−07 | | 1.27 |
| T256A | 2.43E+08 | 7.24E+01 | 2.98E−07 | | 1.90 |
| Q285A | 3.28E+05 | 1.12E−01 | 3.41E−07 | | 1.66 |
| Q285A | 1.37E+08 | 3.52E+01 | 2.57E−07 | | 2.20 |
| T286A | 4.22E+05 | 1.96E−01 | 4.64E−07 | | 1.22 |
| T286A | 5.33E+05 | 3.04E−01 | 5.69E−07 | | 0.99 |
| P307A | 2.87E+08 | 9.31E+01 | 3.25E−07 | | 1.74 |

TABLE 3-continued

| Variant | ka (1/Ms) | kd (1/s) | KD (M) | Comments | WT KD Avg/ Variant KD |
|---|---|---|---|---|---|
| P307A | 3.66E+06 | 1.23E+00 | 3.38E-07 | | 1.67 |
| I308A | 3.57E+05 | 1.69E-01 | 4.72E-07 | | 1.20 |
| I308A | 3.45E+05 | 1.94E-01 | 5.63E-07 | | 1.00 |
| G309A | 1.42E+06 | 3.48E-01 | 2.45E-07 | | 2.31 |
| G309A | 2.44E+05 | 7.19E-02 | 2.94E-07 | | 1.92 |
| Q311A | 2.43E+06 | 8.94E-01 | 3.68E-07 | | 1.54 |
| Q311A | 1.34E+06 | 4.96E-01 | 3.70E-07 | | 1.53 |
| K315A | 4.13E+07 | 1.74E+01 | 4.22E-07 | | 1.34 |
| K315A | 2.45E+05 | 1.34E-01 | 5.48E-07 | | 1.03 |
| D378A | 2.72E+05 | 1.83E-01 | 6.73E-07 | | 0.84 |
| D378A | 3.06E+05 | 1.81E-01 | 5.92E-07 | | 0.96 |
| E380A | 2.41E+05 | 1.80E-01 | 7.47E-07 | | 0.76 |
| E380A | 5.98E+05 | 3.69E-01 | 6.18E-07 | | 0.92 |
| M428A | 2.34E+05 | 1.69E-01 | 7.23E-07 | | 0.78 |
| M428A | 3.18E+05 | 5.32E-01 | 1.67E-06 | | 0.34 |
| E430A | | | | No Binding | |
| E430A | | | | No Binding | |
| H433A | 8.62E+05 | 2.29E-01 | 2.66E-07 | | 2.13 |
| H433A | 2.78E+05 | 9.97E-02 | 3.59E-07 | | 1.58 |
| N434A | 5.18E+05 | 2.37E-01 | 4.57E-07 | | 1.24 |
| N434A | 9.66E+05 | 4.77E-01 | 4.94E-07 | | 1.14 |
| H435A | | | | No Binding | |
| H435A | | | | No Binding | |
| Y436A | 1.04E+06 | 4.07E-01 | 3.93E-07 | | 1.44 |
| Y436A | 2.44E+05 | 2.13E-01 | 8.76E-07 | | 0.65 |
| Wild Type | 3.61E+06 | 1.16E+00 | 3.21E-07 | | 1.76 |
| Wild Type | 6.32E+05 | 3.75E-01 | 5.92E-07 | | 0.96 |
| Wild Type | 4.42E+05 | 1.85E-01 | 4.18E-07 | | 1.35 |
| Wild Type | 5.87E+05 | 3.14E-01 | 5.34E-07 | | 1.06 |
| Wild Type | 3.86E+05 | 1.88E-01 | 4.88E-07 | | 1.16 |
| Wild Type | 3.91E+05 | 2.01E-01 | 5.14E-07 | | 1.10 |
| Wild Type | 2.65E+05 | 1.60E-01 | 6.06E-07 | | 0.93 |
| Wild Type | 3.10E+05 | 1.52E-01 | 4.89E-07 | | 1.16 |
| Wild Type | 2.69E+05 | 1.66E-01 | 6.16E-07 | | 0.92 |
| Wild Type | 7.80E+05 | 4.79E-01 | 6.14E-07 | | 0.92 |
| Wild Type | 2.90E+05 | 1.35E-01 | 4.65E-07 | | 1.22 |
| Wild Type | 1.73E+05 | 1.96E-01 | 1.13E-06 | | 0.50 |
| | | | WT KD Avg | 5.66E-07 | |

Example 2: Generation of NNK Saturation Mutagenesis Libraries at Selected Positions and Analysis of Individual Variants The NNK saturation mutagenesis method is an effective strategy to generate all 20 possible amino acids at a desired position (Hogrefe et al., Biotechniques. 33: 1158-1165 (2002)). Individual NNK libraries at positions 250, 252, 254, 309, 311, 378, 380, and 434 (EU numbering) were generated. For this method, NNK (N=A/C/G/T, K=G/T) primers at the specified position were used with the QuikChange Site-Directed Mutagenesis Kit (Agilent). The supernatants from ninety individual transformants from each library were assayed for binding to canine FcRn at pH 5.5 using the Biacore method described in Example 1. The only difference was the concentration of canine FcRn used in the assay was 200 nM not 400 nM. The sensorgrams for all of the NNK library variants are shown in FIGS. 8-15.

For the NNK library at position 250, none of the variants showed increased binding to canine FcRn at pH 5.5. The data from variants T250E and T250Q and wild type Fc are shown in Table 4. In a competitive binding assay, variants T250E and T250Q in human IgG2 have been demonstrated to bind tighter to human FcRn at pH 6.0 compared to wild-type human IgG2 Fc (Hinton et al., J. Biol. Chem. 279: 6213-6216 (2004)).

TABLE 4

| Variant | ka (1/Ms) | kd (1/s) | KD (M) |
|---|---|---|---|
| T250Q | 9.96E+04 | 2.58E-01 | 2.59E-06 |
| T250Q | 9.43E+04 | 2.68E-01 | 2.84E-06 |
| T250E | 1.14E+05 | 2.84E-01 | 2.48E-06 |
| T250E | 1.72E+05 | 2.87E-01 | 1.66E-06 |
| WT | 3.87E+04 | 3.47E-01 | 8.99E-06 |
| WT | 1.14E+05 | 3.54E-01 | 3.11E-06 |

For the NNK library at position 252, only variants L252Y and L252M had an apparent higher affinity for canine FcRn at pH 5.5 (see Table 5 below). In the 90 transformants, there were no L252F variants present so no binding data was obtained with this variant.

TABLE 5

| Variant | ka (1/Ms) | kd (1/s) | KD (M) |
|---|---|---|---|
| L252Y | 4.02E+05 | 3.97E-02 | 9.87E-08 |
| L252Y | 3.58E+05 | 4.10E-02 | 1.14E-07 |
| L252M | 1.93E+05 | 1.68E-01 | 8.69E-07 |
| L252M | 2.18E+05 | 1.69E-01 | 7.74E-07 |
| WT | 1.68E+05 | 2.88E-01 | 1.71E-06 |
| WT | 1.23E+05 | 3.26E-01 | 2.66E-06 |

For the NNK library at position 254, none of the variants tested had an apparent higher affinity for canine FcRn at pH 5.5. Data for the A254T variant is shown in Table 6 and the corresponding variant in human IgG1 has been used in the YTE variant (M252Y/S254T/T256E) which has an increased affinity to human FcRn at pH 6.0 (Dall'Acqua et al., J. Immunol. 169: 5171-5180 (2002)) and been demonstrated to increase the half-life of human IgG in preclinical models as well as in humans (Borrok et al., J. Biol. Chem. 290: 4282-4290 (2015); Robbie et al., Antimicrob. Agents Ch. 57: 6147-6153 (2013)). In the 90 transformants, there were no A254H variants present so no data was obtained with this variant.

TABLE 6

| Variant | ka (1/Ms) | kd (1/s) | KD (M) |
|---|---|---|---|
| A254T | 1.63E+05 | 3.75E-01 | 2.29E-06 |
| A254T | 3.23E+05 | 4.33E-01 | 1.34E-06 |
| WT | 1.51E+05 | 3.10E-01 | 2.05E-06 |
| WT | 1.05E+05 | 3.15E-01 | 2.99E-06 |

For the NNK libraries at positions 309 and 311, none of the variants tested had an apparent higher affinity for canine FcRn at pH 5.5. Data for the variants G309P and Q311V are shown in Tables 7 and 8 and the corresponding human variants (L309P and Q311V) in human IgG1 in several combinations with other variants have been demonstrated to have a higher affinity for human FcRn at pH 6.0 (Dall'Acqua et al., J. Immunol. 169: 5171-5180 (2002); Booth et al., MAbs, 10(7):1098-1110 (2018)). The variants G309D, G309K and Q311D were not identified in the NNK libraries and therefore were not tested for FcRn binding.

TABLE 7

| Variant | ka (1/Ms) | kd (1/s) | KD (M) |
|---|---|---|---|
| G309P | 3.77E+05 | 2.39E-01 | 6.35E-07 |
| G309P | 5.58E+05 | 2.42E-01 | 4.34E-07 |
| G309P | 2.07E+05 | 1.32E-01 | 6.37E-07 |
| G309P | 2.02E+05 | 1.45E-01 | 7.18E-07 |

TABLE 7-continued

| Variant | ka (1/Ms) | kd (1/s) | KD (M) |
|---|---|---|---|
| WT | 2.37E+05 | 2.10E−01 | 8.84E−07 |
| WT | 2.53E+05 | 2.18E−01 | 8.62E−07 |

TABLE 8

| Variant | ka (1/Ms) | kd (1/s) | KD (M) |
|---|---|---|---|
| Q311V | 1.52E+06 | 5.66E−01 | 3.72E−07 |
| Q311V | 1.59E+06 | 6.96E−01 | 4.39E−07 |
| WT | 2.67E+05 | 1.70E−01 | 6.39E−07 |
| WT | 2.47E+05 | 1.71E−01 | 6.92E−07 |

For the NNK libraries at positions 378 and 380, none of the variants tested had an apparent higher affinity for canine FcRn at pH 5.5. The data for variant D378V is shown in Table 9 and the corresponding variant in human IgG1 has been used in combinations with other IgG variants to demonstrate higher affinity to human FcRn at pH 6.0 compared to wild-type Fc and extending the half-life of human IgG in transgenic human FcRn mice (Monnet et al., MABS. 6: 422-436 (2014); Booth et al., 2018). Also, the data for variant E380A is shown in Table 10 and the corresponding variant in human IgG has been shown to have higher binding affinity to human FcRn at pH 6.0 (Shields et al., J. Biol. Chem. 276: 6591-6604 (2001)). Variants D378E, D378I, D378K, and E380F were not present in the NNK libraries and not screened for binding to canine FcRn.

TABLE 9

| Variant | ka (1/Ms) | kd (1/s) | KD (M) |
|---|---|---|---|
| D378V | 2.29E+05 | 1.59E−01 | 6.93E−07 |
| D378V | 1.84E+05 | 1.60E−01 | 8.73E−07 |
| WT | 3.36E+05 | 1.69E−01 | 5.02E−07 |
| WT | 2.64E+05 | 2.07E−01 | 7.84E−07 |

TABLE 10

| Variant | ka (1/Ms) | kd (1/s) | KD (M) |
|---|---|---|---|
| E380A | 1.68E+05 | 2.23E−01 | 1.32E−06 |
| E380A | 1.52E+05 | 2.39E−01 | 1.57E−06 |
| WT | 1.15E+05 | 1.79E−01 | 1.56E−06 |
| WT | 2.42E+05 | 1.82E−01 | 7.54E−07 |

For the NNK library at position 434, variants N434Y, N434W, and N434R had a higher affinity for canine FcRn at pH 5.5 shown in Table 11. Variants N434S and N434A did not have a higher affinity for canine FcRn at a low pH which is unlike the corresponding human IgG1 variants (Petkova et al., Int. Immunol. 18: 1759-1769 (2006); Yeung et al., J. Immunol. 182: 7663-7671 (2009); Zalevsky et al., Nat. Biotechnol. 28: 157-159 (2010); Deng et al., Drug Metab. Dispos. 38: 600-605 (2010)). The NNK library screened at position 434 did not contain the N434F variant so the binding of this variant to canine FcRn was not tested.

TABLE 11

| Variant | ka (1/Ms) | kd (1/s) | KD (M) |
|---|---|---|---|
| N434Y | 6.07E+05 | 9.68E−03 | 1.59E−08 |
| N434W | 6.93E+05 | 2.80E−02 | 4.04E−08 |
| N434W | 4.20E+06 | 3.18E−01 | 7.57E−08 |
| N434R | 4.88E+05 | 5.24E−02 | 1.07E−07 |
| N434R | 3.99E+05 | 6.33E−02 | 1.59E−07 |
| N434S | 2.25E+05 | 2.07E−01 | 9.24E−07 |
| N434S | 1.99E+05 | 2.09E−01 | 1.05E−06 |
| N434A | 2.72E+05 | 1.56E−01 | 5.73E−07 |
| N434A | 2.61E+05 | 1.64E−01 | 6.29E−07 |
| WT | 1.90E+05 | 1.81E−01 | 9.55E−07 |
| WT | 1.59E+05 | 2.09E−01 | 1.31E−06 |

Example 3: Binding Kinetics for L252Y, N434Y, N434W, N434R, N434H and YTE (L252Y/A254T/T256E) Variants and Wild-Type Fc Several canine IgG.B variants that demonstrated higher affinity to canine FcRn at pH 5.5 were further evaluated for binding kinetics to canine FcRn. In this study, the binding of the variants (L252Y, N434Y, N434W, N434R, N434H), YTE variant (L252Y/A254T/T256E) and wild-type canine Fc to canine FcRn at pH 5.5 and pH 7.4 was evaluated. The Biacore method for the pH 5.5 condition was the same as described in Example 1 with the exception that four concentrations of FcRn (100 nM, 200 nM, 400 nM, 800 nM) were tested which yields more precise binding kinetics. For the Biacore conditions at pH 7.4, the running buffer used was 10 mM HEPES, 500 mM NaCl, 3 mM EDTA, 0.05% Tween 20, pH 7.4 and the concentration of canine FcRn tested was 200 nM. All of the variants including YTE and wild type did not bind to canine FcRn at pH 7.4. The binding kinetics at pH 5.5 are shown in Table 12 and the sensorgrams are shown in FIGS. 16A-16E. The variants tested showed increased affinity for canine FcRn at pH 5.5 as compared to wild type Fc.

TABLE 12

| Variant | ka (1/Ms) | kd (1/s) | KD (M) |
|---|---|---|---|
| L252Y | 2.75E+05 | 4.76E−02 | 1.73E−07 |
| N434Y | 5.20E+05 | 1.51E−02 | 2.91E−08 |
| N434W | 4.46E+05 | 4.50E−02 | 1.01E−07 |
| N434R | 4.40E+05 | 8.01E−02 | 1.82E−07 |
| N434H | 4.11E+05 | 1.02E−01 | 2.47E−07 |
| Wild Type | 1.68E+05 | 5.27E−01 | 3.15E−06 |
| YTE | 2.50E+05 | 4.60E−02 | 1.84E−07 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising a canine IgG Fc region variant, or a canine FcRn-binding region thereof, wherein the canine IgG Fc region variant or the canine FcRn-binding region thereof is different from a wild type canine IgG Fc region or a canine FcRn-binding region thereof by no more than one amino acid, wherein the one amino acid difference is Arg at a position that corresponds to amino acid position 434 of the wild type canine IgG Fc region, wherein the amino acid position is based on EU numbering, and wherein the polypeptide has increased binding affinity to canine FcRn when compared to a control polypeptide, wherein the control polypeptide is identical to the polypeptide except for having the wild type canine IgG Fc region or a FcRn-binding region thereof in place of the canine IgG Fc region variant or the canine FcRn-binding region thereof.

2. The polypeptide of claim 1, wherein the polypeptide further comprises a binding domain.

3. The polypeptide of claim 2, wherein the binding domain comprises (i) six complementarity determining regions (CDRs) of an immunoglobulin molecule; (ii) a ligand binding domain of a canine receptor protein, (iii) a nanobody or (iv) an extracellular domain of a canine receptor protein.

4. The polypeptide of claim 2, wherein the binding domain specifically binds to an antigen selected from the group consisting of NGF, TrKA, ADAMTS, IL-1, IL-2, IL-4, IL-4R, Angiotensin type 1 (AT1) receptor, Angiotensin type 2 (AT2) receptor, IL-5, IL-12, IL-13, IL-31, IL-33, CD3, CD20, CD47, CD52, and complement system complex.

5. The polypeptide of claim 1, further comprising a protein selected from the group consisting of EPO, CTLA4, LFA3, VEGFR1/VEGFR3, IL-1 R, IL-4R, GLP-1 receptor agonist, and Thrombopoietin binding peptide.

6. The polypeptide of claim 1, wherein the polypeptide binds to a canine FcRn at a higher level at pH 5.5 than at pH 7.4.

7. A pharmaceutical composition comprising (i) the polypeptide of claim 1, and (ii) a pharmaceutically acceptable excipient.

* * * * *